United States Patent [19]

Yonekura et al.

[11] Patent Number: 4,871,751

[45] Date of Patent: Oct. 3, 1989

[54] 1,2,6-TRIPHENYL-4(1H)-PYRIDINONE DERIVATIVES, AND THEIR USE AS FUNGICIDES

[75] Inventors: Norihisa Yonekura, Shizuoka; Takashi Yumita, Hamamatsu; Yukio Nezu, Fujieda; Yoshiyuki Kojima, Kakegawa; Shin-ichiro Maeno, Shizuoka; Shigeharu Yaguchi, Shizuoka, all of Japan

[73] Assignees: Kumai Chemical Industry Co., Ltd., Tokyo, Japan; Ihara Chemical Industry Co., Ltd., Tokyo, Japan

[21] Appl. No.: 178,421

[22] Filed: Apr. 6, 1988

Related U.S. Application Data

[63] Continuation of Ser. No. 29,944, Mar. 26, 1987, Pat. No. 4,757,081.

[30] Foreign Application Priority Data

Mar. 26, 1986 [JP] Japan .................................. 61-67438
May 19, 1986 [JP] Japan ................................ 61-114030
Aug. 5, 1986 [JP] Japan ................................ 61-183876

[51] Int. Cl.$^4$ .................... A61K 31/44; C07D 213/62; C07D 213/78

[52] U.S. Cl. ...................................... 514/345; 514/338; 514/344; 514/347; 514/348; 514/350; 514/351; 514/346; 546/14; 546/270; 546/290; 546/291; 546/296; 546/298; 546/300; 546/301; 546/302; 546/303

[58] Field of Search ................. 546/14, 270, 291, 296, 546/298, 300, 301, 302, 303, 290; 514/344, 345, 346, 347, 348, 350, 351, 338

[56] References Cited

U.S. PATENT DOCUMENTS 4,757,081  7/1988  Yonekura et al. ................... 546/270

Primary Examiner—Mary C. Lee
Assistant Examiner—J. Richter
Attorney, Agent, or Firm—Oblon, Spivak, McClelland, Maier & Neustadt

[57] ABSTRACT

New substituted derivatives of 1,2,6-triphenyl-4(1H)-pyridone are now provided, which are useful as fungicidal agent having practically valuable and improved fungicidal activities against a variety of phyto-pathogenic microorganisms, especially fungi and which show low toxicity to animals, including humans. These new compounds may be produced by different processes.

15 Claims, No Drawings

1,2,6-TRIPHENYL-4(1H)-PYRIDINONE DERIVATIVES, AND THEIR USE AS FUNGICIDES

This application is a continuation of Ser. No. 029,944, filed Mar. 26, 1987, now U.S. Pat. No. 4,757,081.

SUMMARY OF THE INVENTION:

This invention relates to new 4(1H)-pyridinone derivatives, and more particularly, new 1,2,6-triphenyl-substituted 4(1H)-pyridinone derivatives which are useful as new compounds or agents having improved fungicidal activities. This invention also relates to a fungicidal composition containing said new 4(1H)-pyridinone derivatives as active ingredient. This invention further relates to processes for the production of said new 4(1H)-pyridinone derivatives.

An article of the "Synthetic Communications" 13(5), 411-417 (1983) describes a process for the production of 1,2,6-triphenyl-substituted 4(1H)-pyridinone derivatives by reactions between ketimines and ethyl phenylpropionate, and this article discloses some examples of the 1,2,6-triphenyl-substituted 4(1H)-pyridinone derivatives produced, which are merely described there to be interesting as intermediate compounds for synthetic production of other, final products. On the other hand, Japanese patent application first publication "Kokai" No. 65871/81 discloses 1-phenyl-2,6-dimethyl-4(1H)-pyridinone derivatives. It also contains a disclosure to the effect that these derivatives are not only effective for cucumber powdery mildew (*Sphaerotheca fuliginea*) but also useful as slime control agents. Similarly, Japanese patent application first publication "Kokai" No. 102504/80 discloses 2,6-diphenyl-4(1H)-pyridinone and contains a description to the effect that this compound is effective for rice blast (*Pyricularia oryzae*) and cucumber anthracnose (*Colletotrichum lagenarium*). 3-Substituted phenyl- or 3,5-disubstituted phenyl-4 -pyridinone derivatives are also disclosed in Japanese patent application second publication "Kokoku" No. 350/85 and No. 351/85, and these compounds have activities as herbicides but no description is given there as to their fungicidal effects.

The above article in the "Synthetic Communication" does not describe anything about the biological activities of the compounds disclosed there. In order to provide a novel, agricultural and horticultural fungicide more useful than the known compounds described in the above-mentioned publications, we, the present inventors, have paid our attention on the 1,2,6-triphenyl-substituted 4(1H)-pyridinone derivatives and its skeleton structure and have carried out extensive investigations to provide their new 3-substituted derivatives. As a result, we have now succeeded to synthesize new compounds of this invention. It has also been found that the new compounds of this invention have improved and excellent activities as agricultural and horticultural fungicides, leading to completion of this invention.

DETAILED DESCRIPTION OF THE INVENTION

According to a first and broadest aspect of this invention, there is provided as new compounds 4(1H)-pyridinone derivatives represented by the general formula:

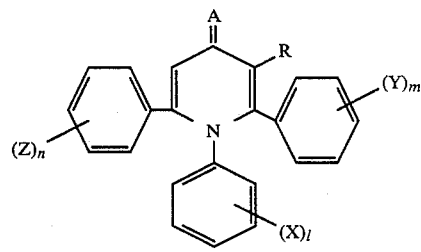

wherein X, Y and Z are the same or different and are independently a halogen atom, a nitro group, a cyano group, a hydroxy group, aldehyde group (—CHO), an alkyl group, a halogen-substituted alkyl group, a cyanoalkyl group, a hydroxyalkyl group, an alkoxyalkyl group, an alkoxy group, a halogen-substituted alkoxy group, an alkoxyalkoxy group, an alkenyl group, an alkenyloxy group, an alkynyl group, an alkynyloxy group, an alkanoyl group, preferably formyl or acetyl, an alkanoyloxy group, preferably acetyloxy, a phenyl group, a phenoxy group, a carbamoyl group, an alkylcarbamoyloxy group, a carboxyl or carboxylate group of the formula —COOR$^1$ where R$^1$ is a hydrogen atom or an alkyl group, or a substituted or unsubstituted amino group of the formula

where R$^2$ and R$^3$ are the same or different and are each a hydrogen atom, a lower alkyl group, preferably methyl, or an alkanoyl group; or X, Y and Z are independently a group of the formula —(O)$_p$—S—R$^4$ where R$^4$ is an alkyl group and p is an integer of 0 to 3; or X, Y and Z are independently a trimethylene group or a methylene-dioxo group bonded to and bridging between the adjacent two carbon atoms of the benzene ring to which X, Y or Z is linking so that X, y or Z taken together with said two adjacent two carbon atoms of the benzene ring forms a 5-membered ring.

l, m and n are independently an integer of 0 to 5, R is a halogen atom, a cyano group, an alkyl group, a halogen-substituted alkyl group, an alkoxy group, an alkenyl group, an alkynyl group, a phenyl group, a benzyl group, a trimethylsilylethynyl group, a carboxyl or carboxylate group of the formula —COOR$^1$ where R$^1$ is as defined above, or a substituted methyl group of the formula —CH$_2$OR$^5$ wherein R$^5$ is a hydrogen atom, an alkyl group or a benzoyl group, A is an oxygen atom or a sulfur atom, provided that when R is methyl and A is an oxygen atom, l, m and n do not denote zero simultaneously; and provided that when R and X are each a methyl group, A is an oxygen atom and l is 1, m and n do not denote zero simultaneously, and a salt of the compound of the formula (I) above.

The compound of the formula (I) according to this invention may also be converted into their salts with an acid or a cation.

Further, the compounds of this invention may be in the form of such a tautomer as indicated below.

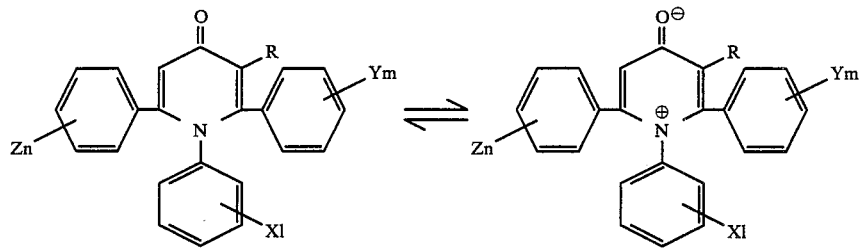

In the compounds of formula (I) according to this invention, R may preferably be an alkyl group, particularly a ($C_1$–$C_6$) alkyl group, or a halogen atom, a cyano group or a carboxyl or carboxylate group of the formula —COOR$^1$ where R$^1$ is a hydrogen atom or an alkyl group. More preferably, R is a ($C_1$–$C_4$) alkyl group, a chlorine atom or a bromine atom.

In the compounds of formula (I), X, Y and Z may preferably be the same or different and are independently an alkyl group, an alkoxy group, a halogen-substituted alkyl group, an alkoxy group, a halogen-substituted alkoxy group, a halogen group, nitro group, cyano group, an alkenyl group, an alkenyloxy group, an alkynyl group or an alkynyloxy group, or X, Y and Z are independently a trimethylene group or a methylene-dioxo group bonded to and bridging between the adjacent two carbon atoms of the benzene ring to which X, Y or Z is linking so that, X, Y or Z taken together with said two carbon atoms of the benzene ring forms a 5-membered ring; l, m and n are independently an integer of 0 to 5; and A is an oxygen atom or a sulfur atom.

In the compounds of formula (I), it is preferred that the sum of l, m and n is equal to 2 or greater than 2.

In the compounds of formula (I), two or more groups may be present for each of the groups X, Y and X and they are the same or different from each other in their nature.

In the compounds of formula (I), it is preferred that X is a halogen atom or an alkoxy group or a combination of halogen atom(s) and alkoxy group(s); Y is a halogen atom or an alkoxy group or a combination of halogen atom(s) and alkoxy group(s); and Z is a halogen atom or an alkoxy group or a combination of halogen atom(s) and alkoxy group(s).

In the compounds of formula (I), one, two or three groups for X may be present therein and may preferably be positioned at the 2-position, the 3-position, the 2- and 4-positions, the 2- and 5-positions, the 3- and 5-positions or the 2-, 3- and 5-positions of the benzene ring to which the group(s) X is or are linking.

In the compound of the general formula (I) according to this invention, an alkyl group as represented by the substitutents X, Y, Z, R, R$^1$, R$^4$ and R$^5$, as well as a cycloalkyl group occasionally present in theses substituents X, Y, Z and others may be an alkyl group containing 1 to 6 carbon atoms, preferably an alkyl group containing 1 to 4 carbon atoms. The alkyl group may include a cycloalkyl group such as cyclopentyl. Suitable examples of an alkyl group includes methyl, ethyl, n-propyl, isopropyl, n-butyl, isobutyl, tert-butyl, pentyl and hexyl. The halogen group includes bromine, chlorine, flourine and iodine.

According to particular embodiments of the first aspect of this invention, there are provided the following four types of the compounds:

(A) A compound represented by the general formula (Ia):

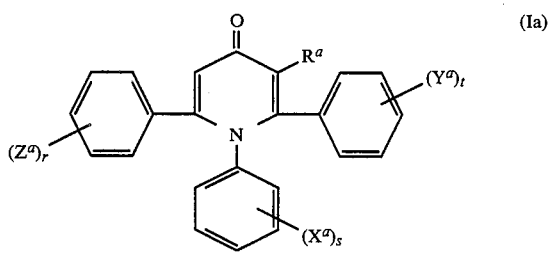

wherein
X$^a$ is a halogen atom, a nitro group, a cyano group, a hydroxy group, an alkyl group, a halogen-substituted alkyl group, a cyanoalkyl group, a hydroxyalkyl group, an alkoxyalkyl group, an alkoxy group, a halogen-substituted alkoxy group, an alkoxyalkoxy group, an alkenyl group, an alkenyloxy group, an alkynyl group, an alkynyloxy group, an alkanoyl group, an alkanoyloxy group, a phenyl group a phenoxy group, a carbamoyl group, an alkylcarbamoyloxy group, a carboxyl or carbooxylate group of the formula —COOR$^1$ where R$^1$ is a hydrogen atom or an alkyl group, or a substituted or unsubstituted amino group of the formula

where R$^2$ and R$^3$ are the same or different and are each a hydrogen atom, a lower alkyl group, or an alkanoyl group; or X$^a$ is a group of the formula —(O)$_p$—S—R$^4$ where R$^4$ is an alkyl group an p is an integer of 0 to 3; or X$^a$ is a trimethylene group or a methylene-dioxo group bonded to and bridging between the adjacent two carbon atoms of the benzene ring to which X$^a$ is linking so that X$^a$ taken together with said two adjacent two carbon atoms of the benzene ring forms a 5-membered ring;

Y$^a$ is a halogen atom, a nitro group, a cyano group, a hydroxy group, an alkyl group, a halogen-substituted alkyl group, a hydroxyalkyl group, an alkoxyalkyl group, an alkoxy group, a halogen-substituted alkoxy group, an alkoxyalkoxy group, an alkenyl group, an alkenyloxy group, an alkynyl group, an alkynyloxy group, an alkanoyl group, an alkanoyloxy group, a carbamoyl group, an alkylcarbamoyloxy group, a carboxyl or carboxylate group of the formula —COOR$^1$ where R$^1$ is a hydrogen atom or an alkyl group, or Y$^a$ is a group of the formula —(O)$_p$—S—R$^4$ where R$^4$ is an alkyl group and p is an integer of 0 to 3; or Y$^a$ is a trimethylene group or a methylene-dioxo group bonded to and bridging between the adjacent two carbon atoms of the benzene ring to which Y$^a$ is linking so that Y$^a$ taken together with said two adjacent two carbon atoms of the benzene ring forms a 5-membered ring, Z$^a$ is a halogen atom, a nitro group, a cyano group, a hydroxy group, aldehyde group (—CHO), an alkyl group, a halogen-substituted alkyl group, a hydroxyalkyl group, an alkoxyalkyl group, an alkoxy group, a halogen-substituted alkoxy group, an alkoxyalkoxy group, an alkenyl group, an alkenyloxy group, an alkynyl group, an alkynyloxy group, an alkanoyl group, an alkanoyloxy group, preferably acetyloxy, a carbamoyl group, an alkylcarbamoyloxy group, a carboxyl or carboxylate group of the formula —COOR$^1$ where R$^1$ is a hydrogen atom or an alkyl group, or Z$^a$ is a group of the formula —(O)$_p$—S—R$^4$ is an alkyl group and p is an integer of 0 to 3; or Z$^a$ is a trimethylene group or a methylene-dioxo group bonded to and bridging between the adjacent two carbon atoms of the benzene ring to which Z$^a$ is linking so that Z$^a$ taken together with said two adjacent two carbon atoms of the benzene ring forms a 5-membered ring, s is an integer of zero, 1, 2 or 3; t is an integer of zero, 1 or 2; and r is zero, 1 or 2.

R$^a$ is a halogen atom, a cyano group, an alkyl group, a halogen-substituted alkyl group, an alkoxy group, an alkenyl group, an alkynyl group, a phenyl group, a benzyl group, a trimethylsilylethynyl group, a carboxyl or carboxylate group of the formula —COOR$^1$ where R$^1$ is as defined above, or a substituted methyl group of the formula —CH$_2$OR$^5$ wherein R$^5$ is a hydrogen atom, an alkyl group or a benzoyl group, provided that when R$^a$ is methyl, s, t and r do not denote zero simultaneously.

(B) A compound represented by the general formula

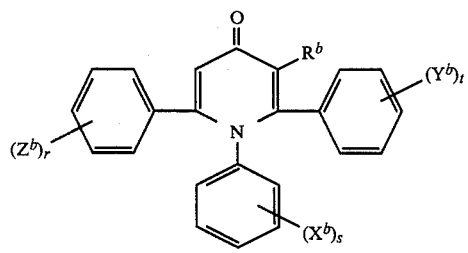

wherein

X$^b$ is a halogen atom or an alkoxy group or a combination of halogen atom(s) and alkoxy group(s); Y$^b$ is a halogen atom, especially chlorine or flourine, or an alkoxy group and Z$^b$ is a halogen atom, especially flourine, s is an integer of zero, 1, 2 or 3; t is an integer of zero, 1 or 2; and r is an integer of zero, 1 or 2.

R$^b$ is an alkyl group or a halogen atom, especially chlorine or flourine, provided that when R$^b$ is methyl, s, t, and r do not denote zero simultaneously.

(C) A compound represented by the general formula

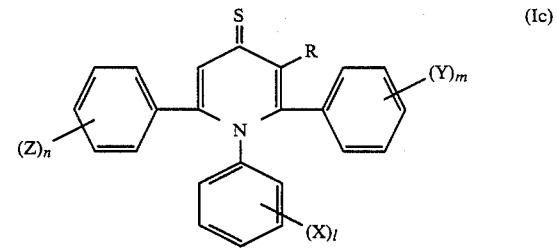

wherein

X, Y and Z are the same or different and are independently a halogen atom, an alkoxy group, an alkenyl group, an alkenyloxy group, an alkynyl group or an alkynyloxy group, l, m and n are independently an integer of 0 to 5, R is an alkyl group or a halogen-substituted alkyl group.

(D) A compound represented by the general formula

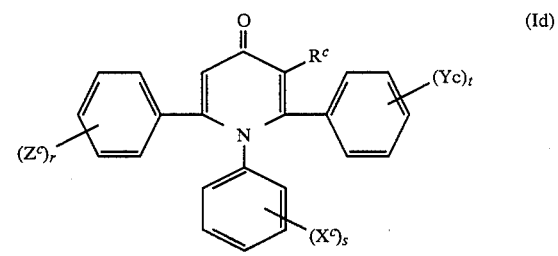

wherein

X$^c$ is an alkyl group; Y$^c$ is a halogen atom, especially chlorine or flourine, an alkyl group, or an alkoxy group; and Z$^c$ is a halogen atom, especially flourine, s in an integer of zero, 1, 2 or 3; t is an integer of zero, 1 or 2; and r is an integer of zero, 1 or 2.

R$^c$ is an alkyl group or a halogen atom, especially chlorine or flourine, provided that when R$^c$ is methyl, s, t, and r do not denote zero simultaneously, and provided that t and r do not denote zero simultaneously.

Particular examples of the compounds of this invention represented by the general formula (I) will next be shown in Table 1a–Table 1d below. Compound numbers given in these Tables will be referred to in the subsequent descriptions.

TABLE 1a

| Compound No. | Xl | Ym | Zn | A | R | Melting point(°C.) |
|---|---|---|---|---|---|---|
| 1 | 2-Cl | H | H | O | CH₃ | 228–231 |
| 2 | 2-Cl | " | " | " | " | 229–231 |
| 3 | 3-Cl | " | " | " | " | 219–221 |
| 4 | 4-Cl | " | " | " | " | 268–270 |
| 5 | 2-F | " | " | " | " | 221–225 |
| 6 | 3-F | " | " | " | " | 243–246 |
| 7 | 4-F | " | " | " | " | 256–259 |
| 8 | 2-Br | " | " | " | " | 201–203 |
| 9 | 2-I | " | " | " | " | 219–222 |
| 10 | 2-C₂H₅ | " | " | " | " | 230–234 |
| 11 | 2-C₃H₇—i | " | " | " | " | 233–236 |
| 12 | 4-C₃H₇—i | " | " | " | " | 282–284 |
| 13 | 4-C₄H₉—n | " | " | " | " | 150–151 |
| 14 | 4-C₄H₉—t | " | " | " | " | 255–257 |
| 15 | 2-OCH₃ | " | " | " | " | 179–181 |
| 16 | 3-OCH₃ | " | " | " | " | 183–185 |
| 17 | 4-OCH₃ | H | H | O | CH₃ | 237–239 |
| 18 | 2-OC₂H₅ | " | " | " | " | 179–182 |
| 19 | 3-OC₂H₅ | " | " | " | " | 206–209 |
| 20 | 4-OC₂H₅ | " | " | " | " | 205–208 |
| 21 | 2-OC₃H₇—i | " | " | " | " | 177–180 |
| 22 | 3-OC₃H₇—i | " | " | " | " | 152–154 |
| 23 | 4-OC₃H₇—i | " | " | " | " | 222–225 |
| 24 | 2-COOCH₃ | " | " | " | " | 227–229 |
| 25 | 2-COOC₂H₅ | " | " | " | " | 208–211 |
| 26 | 3-COOC₂H₅ | " | " | " | " | 196–198 |
| 27 | 4-COOC₂H₅ | " | " | " | " | 202–204 |
| 28 | 2-OH | " | " | " | " | >300 |
| 29 | 3-OH | " | " | " | " | >300 |
| 30 | 4-OH | " | " | " | " | >300 |
| 31 | 2-OCOCH₃ | " | " | " | " | 199–203 |
| 32 | 2-NO₂ | " | " | " | " | 223–225 |
| 33 | 3-NO₂ | " | " | " | " | 260–262 |
| 34 | 4-NO₂ | " | " | " | " | 271–273 |
| 35 | 2-CN | " | " | " | " | 218–222 |
| 36 | 3-CN | " | " | " | " | 257–259 |
| 37 | 4-CN | " | " | " | " | 285–291 |
| 38 | 2-NH₂ | " | " | " | " | >300 |
| 39 | 3-NH₂ | " | " | " | " | 273–277 |
| 40 | 4-NH₂ | " | " | " | " | >300 |
| 41 | 2-NHCH₃ | H | H | O | CH₃ | 291–293 |
| 42 | 4-N(CH₃)₂ | " | " | " | " | 228–233 |
| 43 | 2-SCH₃ | " | " | " | " | 228–231 |
| 44 | 3-SCH₃ | " | " | " | " | 198–201 |
| 45 | 4-SCH₃ | " | " | " | " | 237–238 |
| 46 | 2-S(O)CH₃ | " | " | " | " | 250–253 |

TABLE 1a-continued

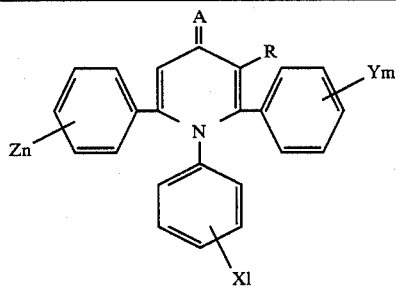

| Compound No. | Xl | Ym | Zn | A | R | Melting point(°C.) |
|---|---|---|---|---|---|---|
| 47 | 3-SCH₃ (O↑) | " | " | " | " | No measurable |
| 48 | 4-SCH₃ (O↑) | " | " | " | " | 242–244 |
| 49 | 2-SO₂CH₃ | " | " | " | " | 279–281 |
| 50 | 3-SO₂CH₃ | " | " | " | " | 246–248 |
| 51 | 4-SO₂CH₃ | " | " | " | " | 222–225 |
| 52 | 2-CH₂CH=CH₂ | " | " | " | " | 201–204 |
| 53 | 2-CF₃ | " | " | " | " | 259–261 |
| 54 | 3-CF₃ | " | " | " | " | 235–237 |
| 55 | 4-CF₃ | " | " | " | " | 234–237 |
| 56 | 3-CH₂OCH₃ | " | " | " | " | 155–156 |
| 57 | 2-COCH₃ | " | " | " | " | {225–228, 233–224} |
| 58 | 3-COCH₃ | " | " | " | " | 201–203 |
| 59 | 2-OCH₂CH=CH₂ | " | " | " | " | 152–155 |
| 60 | 3-OCH₂CH=CH₂ | " | " | " | " | 170–171 |
| 61 | 4-OCH₂CH=CH₂ | " | " | " | " | 197–198 |
| 62 | 2-C≡CH | H | H | O | CH₃ | 187–190 |
| 63 | 3-C≡CH | " | " | " | " | 241–245 |
| 64 | 4-C≡CH | " | " | " | " | >300 |
| 65 | 2-OCHF₂ | " | " | " | " | 196–200 |
| 66 | 3-OCHF₂ | " | " | " | " | 167–169 |
| 67 | 2-OC₄H₉—n | " | " | " | " | 141–144 |
| 68 | 3-OC₄H₉—n | " | " | " | " | 121–123 |
| 69 | 4-OC₄H₉—n | " | " | " | " | 130–134 |
| 70 | 2-CH₂CN | " | " | " | " | >300 |
| 71 | 4-OCF₃ | " | " | " | " | 235–237 |
| 72 | 4-OCF₂CF₂H | " | " | " | " | 151–154 |
| 73 | 3,4 —O—CH₂—O— | " | " | " | " | 236.5–237 |
| 74 | 3,4 —CH₂—CH₂—CH₂— | " | " | " | " | 234–235 |
| 75 | 3-OCH₂C≡CH | " | " | " | " | 166–169 |
| 76 | 2,3-Cl₂ | " | " | " | " | {210–213, 233–235} |
| 77 | 2,4-Cl₂ | " | " | " | " | 257–260 |
| 78 | 2,5-Cl₂ | " | " | " | " | 269–271 |
| 79 | 2,6-Cl₂ | " | " | " | " | 232–235 |
| 80 | 3,4-Cl₂ | " | " | " | " | 233–235 |
| 81 | 3,5-Cl₂ | " | " | " | " | 253–255 |

TABLE 1a-continued

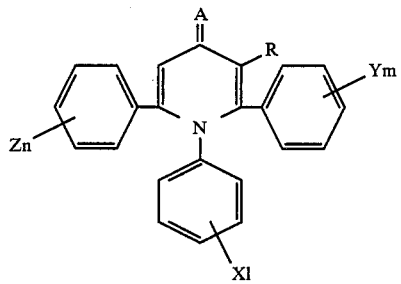

| Compound No. | Xl | Ym | Zn | A | R | Melting point(°C.) |
|---|---|---|---|---|---|---|
| 82 | 2,3-(CH$_3$)$_2$ | " | " | " | " | 212–214 |
| 83 | 2,4-(CH$_3$)$_2$ | " | " | " | " | 217–220 |
| 84 | 2,5-(CH$_3$)$_2$ | " | " | " | " | 268–269 |
| 85 | 2,6-(CH$_3$)$_2$ | " | " | " | " | 197–200 |
| 86 | 3,4-(CH$_3$)$_2$ | H | H | O | CH$_3$ | 222–225 |
| 87 | 3,5-(CH$_3$)$_2$ | " | " | " | " | 268–271 |
| 88 | 2,3-(OCH$_3$)$_2$ | " | " | " | " | 198–199 |
| 89 | 2,4-(OCH$_3$)$_2$ | " | " | " | " | 222–225 |
| 90 | 2,5-(OCH$_3$)$_2$ | " | " | " | " | 197–199 |
| 91 | 2,6-(OCH$_3$)$_2$ | " | " | " | " | 185–187 |
| 92 | 3,4-(OCH$_3$)$_2$ | " | " | " | " | 230–232 |
| 93 | 3,5-(OCH$_3$)$_2$ | " | " | " | " | 232–236 |
| 94 | 2,3-F$_2$ | " | " | " | " | 210–212 |
| 95 | 2,4-F$_2$ | " | " | " | " | 260–261 |
| 96 | 2,5-F$_2$ | " | " | " | " | 216–218 |
| 97 | 2,6-F$_2$ | " | " | " | " | 219–221 |
| 98 | 3,4-F$_2$ | " | " | " | " | 228–229 |
| 99 | 3,5-F$_2$ | " | " | " | " | 268–269 |
| 100 | 2,3-Br$_2$ | " | " | " | " | — |
| 101 | 2,4-Br$_2$ | " | " | " | " | 256–259 |
| 102 | 2,5-Br$_2$ | " | " | " | " | 285–287 |
| 103 | 2,6-Br$_2$ | " | " | " | " | — |
| 104 | 2-Cl,6-CH$_3$ | " | " | " | " | 189–191 |
| 105 | 2-Cl,4-NO$_2$ | " | " | " | " | 212–214 |
| 106 | 2-Cl,5-NO$_2$ | " | " | " | " | 277–279 |
| 107 | 2-Cl,4-Br | " | " | " | " | 252–255 |
| 108 | 2-Cl,5-CF$_3$ | " | " | " | " | 256–258 |
| 109 | 2-Cl,5-CH$_3$ | " | " | " | " | 240–240.5 |
| 110 | 2-CH$_3$,3-Cl | " | " | " | " | 244–246 |
| 111 | 2-CH$_3$,4-Cl | H | H | O | CH$_3$ | 240–242 |
| 112 | 2-CH$_3$,5-Cl | " | " | " | " | >300 |
| 113 | 2-CH$_3$,4-Br | " | " | " | " | 235–237 |
| 114 | 2-CH$_3$,5-F | " | " | " | " | 277.5–278 |
| 115 | 2-NO$_2$,4-Cl | " | " | " | " | 220–223 |
| 116 | 2-Br,4-CH$_3$ | " | " | " | " | 226–229 |
| 117 | 2-F,5-NO$_2$ | " | " | " | " | 220–222 |
| 118 | 2-OCH$_3$,5-Cl | " | " | " | " | 229–232 |
| 119 | 2-OCH$_3$,5-CH$_3$ | " | " | " | " | 215–216 |
| 120 | 2-CF$_3$,4-Cl | " | " | " | " | 241–243 |
| 121 | 2-CN,4-Cl | " | " | " | " | 195–198 / 220–220 |
| 122 | 3-Cl,4-CH$_3$ | " | " | " | " | 226–228 |
| 123 | 3-Cl,4-F | " | " | " | " | 224–225 |
| 124 | 3-NO$_2$,4-F | " | " | " | " | 225–227 |
| 125 | 3-NO$_2$,4-Cl | " | " | " | " | 247–248 |
| 126 | 3-CF$_3$,4-Cl | " | " | " | " | 231–232 |
| 127 | 3-CF$_3$,4-OCH$_3$ | " | " | " | " | 205–208 |
| 128 | 3-CH$_3$,4-Br | " | " | " | " | 225–227 |
| 129 | 2-CH$_3$,5-OCH$_3$ | " | " | " | " | 228–229 |
| 130 | 2-CH$_3$,3-OCH$_3$ | " | " | " | " | 231–233 |
| 131 | 2-CH$_3$,4-NO$_2$ | " | " | " | " | 248–249 |
| 132 | 2-OCH$_3$,4-NO$_2$ | " | " | " | " | 229–231 |
| 133 | 2-OCH$_3$,5-NO$_2$ | " | " | " | " | 224–225 |
| 134 | 2-NO$_2$,4-OCH$_3$ | " | " | " | " | 209–210 |
| 135 | 2-Cl,5-OCH$_3$ | " | " | " | " | 224–225 |
| 136 | 2-OCH$_3$,6-CH$_3$ | H | H | O | CH$_3$ | 163–165 |
| 137 | 2-CH$_3$,3-F | " | " | " | " | 267–268 |
| 138 | 2-NO$_2$,4-CH$_3$ | " | " | " | " | 253–255 |
| 139 | 2-NO$_2$,5-Cl | " | " | " | " | 212–214 |
| 140 | 2-CH$_3$,5-NO$_2$ | " | " | " | " | >300 |
| 141 | 3,5-(OH)$_2$ | " | " | " | " | >300 |

TABLE 1a-continued

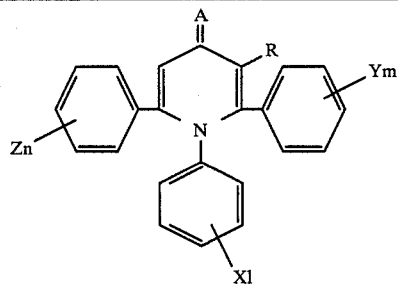

| Compound No. | Xl | Ym | Zn | A | R | Melting point(°C.) |
|---|---|---|---|---|---|---|
| 142 | 3,5-(OCHF$_2$)$_2$ | " | " | " | " | 179–181 |
| 143 | 3,5-(OC$_2$H$_5$)$_2$ | " | " | " | " | 156–158 |
| 144 | 3,5-(O—n-C$_3$H$_7$)$_2$ | " | " | " | " | 156–158 |
| 145 | 2-CH$_3$,4-OCH$_3$ | " | " | " | " | 195–197 |
| 146 | 2-OCH$_3$,4-CH$_3$ | " | " | " | " | 217–219 |
| 147 | 2-Cl,4-CH$_3$ | " | " | " | " | 222–224 |
| 148 | 2-Cl,3-OCH$_3$ | " | " | " | " | 226–227 |
| 149 | 2,4-Cl$_2$,3-CH$_3$ | " | " | " | " | 237–238 |
| 150 | 3,4,5-(OCH$_3$)$_3$ | " | " | " | " | 254–255 |
| 151 | 2,4-Cl$_2$,5-OC$_3$H$_7$—i | " | " | " | " | 205–206 |
| 152 | 2,3,4-Cl$_3$ | " | " | " | " | 257–258 |
| 153 | 2,4-F$_2$,3,5-Cl$_2$ | " | " | " | " | 243–245 |
| 154 | 2-Cl,3,5-(OCH$_3$)$_2$ | " | " | " | " | 262–263 |
| 155 | 2,3,4,5,6-F$_5$ | " | " | " | " | 192–194 |
| 156 | 2,3,4,5-Cl$_4$ | " | " | " | " | 294–296 |
| 157 | 2,3,4,6-Cl$_4$ | " | " | " | " | — |
| 158 | 2,3,5,6-F$_4$ | " | " | " | " | 220–222 |
| 159 | 2-Cl | " | " | " | C$_2$H$_5$ | 163–166 |
| 160 | " | " | " | " | Cl | 230–233 |
| 161 | 2-Br | H | H | O | " | 238–241 |
| 162 | 3-Cl | " | " | " | " | 276–279 |
| 163 | 4-Cl | " | " | " | " | >300 |
| 164 | 2-F | " | " | " | " | 227–229 |
| 165 | 2-I | " | " | " | " | 238–239 |
| 166 | 2-CH$_3$ | " | " | " | " | 266–268 |
| 167 | 3-CH$_3$ | " | " | " | " | 271–273 |
| 168 | 4-CH$_3$ | " | " | " | " | 292–296 |
| 169 | 2-OCH$_3$ | " | " | " | " | 208–209 |
| 170 | 3-OCH$_3$ | " | " | " | " | 250–251 |
| 171 | 4-OCH$_3$ | " | " | " | " | 266–267 |
| 172 | 2-NO$_2$ | " | " | " | " | 250–252 |
| 173 | 3,5-(OCH$_3$)$_2$ | " | " | " | " | 275–276 |
| 174 | " | " | " | " | C$_2$H$_5$ | 166–167 |
| 175 | 2-Cl,5-OCH$_3$ | " | " | " | " | 175–176 |
| 176 | H | 2-Cl | " | " | CH$_3$ | 221–225 |
| 177 | " | 3-Cl | " | " | " | 225–227 |
| 178 | " | 4-Cl | " | " | " | 209–212 |
| 179 | " | 2-F | " | " | " | 177–180 |
| 180 | " | 3-F | " | " | " | 226–228 |
| 181 | " | 4-F | " | " | " | 239–244 |
| 182 | " | 2-Br | " | " | " | 240–241 |
| 183 | " | 2-Br | " | " | " | 236–238 (hydrochloride) |
| 184 | " | 3-Br | " | " | " | 237–239 |
| 185 | " | 4-Br | " | " | " | 203–206 |
| 186 | H | 2-I | H | O | CH$_3$ | 239–241 |
| 187 | " | 2-CH$_3$ | " | " | " | 194–196 |
| 188 | " | 3-CH$_3$ | " | " | " | 209–211 |
| 189 | " | 4-CH$_3$ | " | " | " | 243–246 |
| 190 | " | 2-C$_3$H$_7$—i | " | " | " | 206–209 |
| 191 | " | 4-C$_3$H$_7$—i | " | " | " | 194–197 |
| 192 | " | 2-OCH$_3$ | " | " | " | 200–202 |
| 193 | " | 3-OCH$_3$ | " | " | " | 201–204 |
| 194 | " | 4-OCH$_3$ | " | " | " | 183–185 |
| 195 | " | 3-OC$_2$H$_5$ | " | " | " | 146–149 |
| 196 | " | 4-OC$_2$H$_5$ | " | " | " | 189–193 |
| 197 | " | 3-OC$_3$H$_7$—n | " | " | " | 137–139 |
| 198 | " | 4-OC$_3$H$_7$—n | " | " | " | 165–168 |
| 199 | " | 2-OC$_3$H$_7$—i | " | " | " | 212–214 |
| 200 | " | 3-OC$_3$H$_7$—i | " | " | " | 161–163 |
| 201 | " | 4-OC$_3$H$_7$—i | " | " | " | 198–201 |
| 202 | " | 3-COOC$_2$H$_5$ | " | " | " | 141–144 |
| 203 | " | 4-COOC$_2$H$_5$ | " | " | " | 99–103 |
| 204 | " | 2-OH | " | " | " | >300 |

TABLE 1a-continued

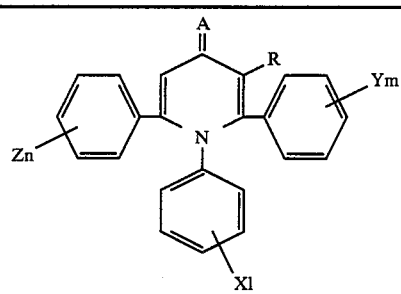

| Compound No. | Xl | Ym | Zn | A | R | Melting point(°C.) |
|---|---|---|---|---|---|---|
| 205 | " | 3-OH | " | " | " | >300 |
| 206 | " | 4-OH | " | " | " | >300 |
| 207 | " | 2-OCOCH₃ | " | " | " | 182–184 |
| 208 | " | 4-OCOCH₃ | " | " | " | 213–216 |
| 209 | " | 3-CN | " | " | " | 262–265 |
| 210 | H | 4-CN | H | O | CH₃ | 240–243 |
| 211 | " | 2-SCH₃ | " | " | " | 199–202 |
| 212 | " | 4-SCH₃ | " | " | " | 200–203 |
| 213 | " | 2-CF₃ | " | " | " | 238–241 |
| 214 | " | 3-CF₃ | " | " | " | 221–223 |
| 215 | " | 4-CF₃ | " | " | " | 209–211 |
| 216 | " | 2-OCH₂CH=CH₂ | " | " | " | 145–148 |
| 217 | " | 4-OCH₂CH=CH₂ | " | " | " | 196–199 |
| 218 | " | 2-OCH₂C≡CH | " | " | " | 211–213 |
| 219 | " | 4-OCH₂C≡CH | " | " | " | 168–170 |
| 220 | " | 2-OCHF₂ | " | " | " | 162–164 |
| 221 | " | 3-COOH | " | " | " | 291–294 |
| 222 | " | 2-C₂H₅ | " | " | " | — |
| 223 | " | 2-C₃H₇—n | " | " | " | — |
| 224 | " | 4-OCH₂OCH₃ | " | " | " | 188–190 |
| 225 | " | 2,3-Cl₂ | " | " | " | 274–278 |
| 226 | " | 2,4-Cl₂ | " | " | " | 183–185 |
| 227 | " | 2,5-Cl₂ | " | " | " | 264–267 |
| 228 | " | 2,6-Cl₂ | " | " | " | — |
| 229 | " | 3,4-Cl₂ | " | " | " | 188–191 |
| 230 | " | 3,5-Cl₂ | " | " | " | 274–277 |
| 231 | " | 2,3-(CH₃)₂ | " | " | " | 250–254 |
| 232 | " | 2,4-(CH₃)₂ | " | " | " | 134–136 |
| 233 | " | 2,5-(CH₃)₂ | " | " | " | 215–217 |
| 234 | " | 2,6-(CH₃)₂ | " | " | " | — |
| 235 | H | 3,4-(CH₃)₂ | H | O | CH₃ | 165–166 |
| 236 | " | 3,5-(CH₃)₂ | " | " | " | 237–239 |
| 237 | " | 2,3-(OCH₃)₂ | " | " | " | 230–235 |
| 238 | " | 2,4-(OCH₃)₂ | " | " | " | 192–194 |
| 239 | " | 2,5-(OCH₃)₂ | " | " | " | 242–244 |
| 240 | " | 2,6-(OCH₃)₂ | " | " | " | — |
| 241 | " | 3,4-(OCH₃)₂ | " | " | " | 210–214 |
| 242 | " | 3,5-(OCH₃)₂ | " | " | " | 212–214 |
| 243 | " | 2,3-F₂ | " | " | " | 165–167 |
| 244 | " | 2,4-F₂ | " | " | " | 213–214 |
| 245 | " | 2,5-F₂ | " | " | " | 222–224 |
| 246 | " | 2,6-F₂ | " | " | " | 221–222 |
| 247 | " | 3,4-F₂ | " | " | " | 202–203 |
| 248 | " | 3,5-F₂ | " | " | " | 205–206 |
| 249 | " | 4-OCHF₂ | " | " | " | 165–166 |
| 250 | " | 3,4-OCH₂O- | " | " | " | 232–235 |
| 251 | " | 2-Cl,4-OCH₃ | " | " | " | 205–206 |
| 252 | " | H | 2-Cl | " | " | 201–204 |
| 253 | " | " | 3-Cl | " | " | 234–236 |
| 254 | " | " | 4-Cl | " | " | 173–175 |
| 255 | " | " | 2-F | " | " | 219–222 |
| 256 | " | " | 3-F | " | " | 204–206 |

TABLE 1a-continued

| Compound No. | Xl | Ym | Zn | A | R | Melting point(°C.) |
|---|---|---|---|---|---|---|
| 257 | " | " | 4-F | " | " | 184–186 |
| 258 | " | " | 2-Br | " | " | 206–209 |
| 259 | H | H | 2-I | O | CH$_3$ | 226–229 |
| 260 | " | " | 2-CH$_3$ | " | " | 188–191 |
| 261 | " | " | 3-CH$_3$ | " | " | 236–238 |
| 262 | " | " | 4-CH$_3$ | " | " | 212–215 |
| 263 | " | " | 2-C$_2$H$_5$ | " | " | — |
| 264 | " | " | 2-C$_3$H$_7$—i | " | " | 224–228 |
| 265 | " | " | 2-C$_4$H$_9$—n | " | " | — |
| 266 | " | " | 2-OCH$_3$ | " | " | 192–194 |
| 267 | " | " | 3-OCH$_3$ | " | " | 201–204 |
| 268 | " | " | 4-OCH$_3$ | " | " | 185–188 |
| 269 | " | " | 2-OC$_2$H$_5$ | " | " | 175–179 |
| 270 | " | " | 2-OC$_3$H$_7$—n | " | " | 166–171 |
| 271 | " | " | 2-OC$_3$H$_7$—i | " | " | 165–168 |
| 272 | " | " | 3-COOC$_2$H$_5$ | " | " | no measurable |
| 273 | " | " | 4-COOC$_2$H$_5$ | " | " | 161–165 |
| 274 | " | " | 2-OH | " | " | >300 |
| 275 | " | " | 3-OH | " | " | >300 |
| 276 | " | " | 4-OH | " | " | 262–268 |
| 277 | " | " | 2-OC(=O)CH$_3$ | " | " | 115–122 |
| 278 | " | " | 3-NO$_2$ | " | " | 210–211 |
| 279 | " | " | 4-NO$_2$ | " | " | 213–216 |
| 280 | " | " | 2-CN | " | " | 261–266 |
| 281 | " | " | 3-CN | " | " | 211–214 |
| 282 | " | " | 4-CN | " | " | 229–233 |
| 283 | H | H | 2-SCH$_3$ | O | CH$_3$ | 189–195 |
| 284 | " | " | 2-CH$_2$Cl | " | " | 167–170 |
| 285 | " | " | 2-CF$_3$ | " | " | 200–205 |
| 286 | " | " | 3-CF$_3$ | " | " | 212–215 |
| 287 | " | " | 2-CH$_2$OCH$_3$ | " | " | 172–176 |
| 288 | " | " | 2-CH$_2$OC$_2$H$_5$ | " | " | 121–124 |
| 289 | " | " | 2-OCH$_2$CF$_3$ | " | " | 191–194 |
| 290 | " | " | 2-COCH$_3$ | " | " | — |
| 291 | " | " | 2-OCH$_2$CH=CH$_2$ | " | " | 171–174 |
| 292 | " | " | 2-OCH$_2$C≡CH | " | " | 182–185 |
| 293 | " | " | 2-OCHF$_2$ | " | " | 163–165 |
| 294 | " | " | 2-COOH | " | " | — |
| 295 | " | " | 3-COOH | " | " | >300 |
| 296 | " | " | 4-COOH | " | " | >293 |
| 297 | " | " | 2-CH$_2$OH | " | " | 254–257 |
| 298 | " | " | 2-CHO | " | " | 169–173 |
| 299 | " | " | 2-SO$_2$CH$_3$ | " | " | >300 |
| 300 | " | " | 3,4-OCH$_2$O- | " | " | 272–275 |
| 301 | " | " | 2-OSO$_2$CH$_3$ | " | " | 209–214 |
| 302 | " | " | 2-O$_2$CNHCH$_3$ | " | " | >300 |
| 303 | " | " | 2-OCH$_2$OCH$_3$ | " | " | 178–181 |
| 304 | " | " | 2,3-Cl$_2$ | " | " | 183–191 |
| 305 | " | " | 2,4-Cl$_2$ | " | " | 218–221 |
| 306 | " | " | 2,5-Cl$_2$ | " | " | >300 |
| 307 | " | " | 2,6-Cl$_2$ | " | " | 151–154 |
| 308 | H | H | 3,4-Cl$_2$ | O | CH$_3$ | 234–236 |
| 309 | " | " | 2,3-(CH$_3$)$_2$ | " | " | 206–208 |
| 310 | " | " | 2,4-(CH$_3$)$_2$ | " | " | 175–178 |

TABLE 1a-continued

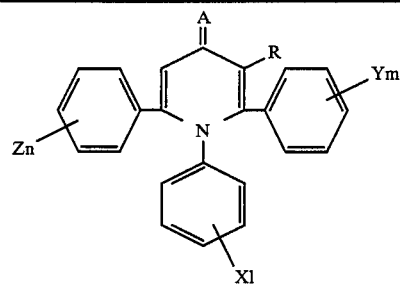

| Compound No. | Xl | Ym | Zn | A | R | Melting point(°C.) |
|---|---|---|---|---|---|---|
| 311 | " | " | 2,5-(CH$_3$)$_2$ | " | " | 231–235 |
| 312 | " | " | 2,6-(CH$_3$)$_2$ | " | " | — |
| 313 | " | " | 3,4-(CH$_3$)$_2$ | " | " | 212–215 |
| 314 | " | " | 3,5-(CH$_3$)$_2$ | " | " | 283–286 |
| 315 | " | " | 2,3-F$_2$ | " | " | 196–197 |
| 316 | " | " | 2,4-F$_2$ | " | " | 206–207 |
| 317 | " | " | 2,5-F$_2$ | " | " | 244–247 |
| 318 | " | " | 2,6-F$_2$ | " | " | 235–238 |
| 319 | " | " | 3,4-F$_2$ | " | " | 188–189 |
| 320 | " | " | 3,5-F$_2$ | " | " | 234–236 |
| 321 | " | " | 3,5-(OCH$_3$)$_2$ | " | " | 205–206 |
| 322 | " | " | 2,4-(OCH$_3$)$_2$ | " | " | 253–257 |
| 323 | " | " | 3,4-(OCH$_3$)$_2$ | " | " | 212–215 |
| 324 | " | " | 2-OC$_2$H$_5$,4-F | " | " | 236–237 |
| 325 | " | " | 2-OCH$_3$,5-Cl | " | " | 192–197 |
| 326 | " | " | 3,5-Cl$_2$ | " | " | >300 |
| 327 | " | " | 2-F,3-OCH$_3$ | " | " | 169–172 |
| 328 | " | " | 2-OCH$_3$,5-F | " | " | 185–186 |
| 329 | " | " | 2,6-(OCH$_3$)$_2$ | " | " | 206–210 |
| 330 | " | " | 2,3-(OCH$_3$)$_2$ | " | " | 239–243 |
| 331 | " | " | 3,4-(OH)$_2$ | " | " | >300 |
| 332 | " | " | 3,5-(OH)$_2$ | " | " | >300 |
| 333 | H | H | 3,4-(OCHF$_2$)$_2$ | O | CH$_3$ | 178–180 |
| 334 | " | " | 2,5-(OCH$_3$)$_2$ | " | " | 242–245 |
| 335 | 2-Cl | 2-Cl | H | " | " | 205–207 |
| 336 | " | " | " | " | " | 232–234 |
| 337 | 2-CH$_3$ | " | " | " | " | 197–200 |
| 338 | " | " | " | " | " | 227–229 |
| 339 | " | " | " | " | " | 222–225 |
| 340 | 2-Cl | 4-OCH$_3$ | " | " | " | 184–188 |
| 341 | 2-CH$_3$ | 3-OCH$_3$ | " | " | " | 212–213 |
| 342 | 3-CH$_3$ | " | " | " | " | 195–196 |
| 343 | 4-CH$_3$ | " | " | " | " | 182–183 |
| 344 | 2-OCH$_3$ | " | " | " | " | 167–169 |
| 345 | 3-OCH$_3$ | " | " | " | " | 153–155 |
| 346 | 4-OCH$_3$ | " | " | " | " | 184–186 |
| 347 | 2-CH$_3$ | 3-Cl | " | " | " | 274–275 |
| 348 | 3-CH$_3$ | " | " | " | " | 219–221 |
| 349 | 4-CH$_3$ | " | " | " | " | 206–208 |
| 350 | 2-OCH$_3$ | " | " | " | " | 231–233 |
| 351 | 3-OCH$_3$ | " | " | " | " | 197–198 |
| 352 | 4-OCH$_3$ | " | " | " | " | 206–207 |
| 353 | 2-Cl | 3-OCH$_3$ | " | " | " | 212–213 |
| 354 | 3-Cl | " | " | " | " | 187–188 |
| 355 | 4-Cl | " | " | " | " | 189–191 |
| 356 | 3-Cl | 2-Cl | " | " | " | 196–198 |
| 357 | 4-Cl | " | " | " | " | 233–236 |
| 358 | 3-CH$_3$ | 2-Cl | H | O | CH$_3$ | 206–209 |
| 359 | 4-CH$_3$ | " | " | " | " | 210–211 |
| 360 | 2-OCH$_3$ | " | " | " | " | 173–176 |
| 361 | 3-OCH$_3$ | " | " | " | " | 166–170 |
| 362 | 4-OCH$_3$ | " | " | " | " | 186–188 |
| 363 | 2-COOCH$_3$ | " | " | " | " | 180–182 |
| 364 | 2-F | " | " | " | " | 207–208 |
| 365 | " | " | " | " | " | 201–203 |
| 366 | 2-Br | " | " | " | " | 117–120 |
| 367 | " | " | " | " | " | 192–195 |
| 368 | 2-NO$_2$ | " | " | " | " | 241–242 |
| 369 | " | " | " | " | " | 233–235 |
| 370 | 3-Cl | 4-OCH$_3$ | " | " | " | 199–203 |
| 371 | 4-Cl | " | " | " | " | 232–234 |
| 372 | 2-CH$_3$ | " | " | " | " | 191–193 |
| 373 | 3-CH$_3$ | " | " | " | " | 187–189 |
| 374 | 4-CH$_3$ | " | " | " | " | 184–186 |

TABLE 1a-continued

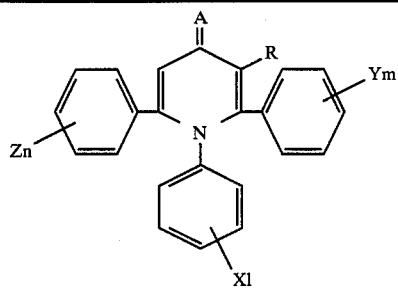

| Compound No. | Xl | Ym | Zn | A | R | Melting point(°C.) |
|---|---|---|---|---|---|---|
| 375 | 2-OCH₃ | " | " | " | " | 248–260 |
| 376 | 3-OCH₃ | " | " | " | " | 207–209 |
| 377 | 4-OCH₃ | " | " | " | " | 212–214 |
| 378 | 2-NO₂ | " | " | " | " | 235–237 |
| 379 | 4-NO₂ | 2-Cl | " | " | " | >300 |
| 380 | 3-NO₂ | " | " | " | " | 193–195 |
| 381 | 3-OCH₃ | 2-CH₃ | " | " | " | 145–148 |
| 382 | 2-Cl | " | " | " | " | 193–195 |
| 383 | 4-CH₃ | 2-CH₃ | H | O | CH₃ | 203–204 |
| 384 | 2-NO₂ | " | " | " | " | 246–248 |
| 385 | 2,5-F₂ | 2-Cl | " | " | " | 189–191 |
| 386 | 2,3-Cl₂ | " | " | " | " | 237–239 |
| 387 | 3,5-Cl₂ | " | " | " | " | 221–223 |
| 388 | 3,5-(OCH₃)₂ | " | " | " | " | 226–229 |
| 389 | 3,5-(OC₂H₅)₂ | " | " | " | " | 195–198 |
| 390 | 3,5-(OCHF₂)₂ | " | " | " | " | 129–130 |
| 391 | 3,5-(OH)₂ | " | " | " | " | >300 |
| 392 | 3,5-(OCH₃)₂ | 4-OCH₃ | " | " | " | 181–183 |
| 393 | " | 3-Cl | " | " | " | 209–211 |
| 394 | 2,5-F₂ | 2-CH₃ | " | " | " | 182–184 |
| 395 | 2-CH₃,3-Cl | " | " | " | " | 230–231 |
| 396 | 2,3-Cl₂ | " | " | " | " | 139–141 |
| 397 | 3,5-(OCH₃)₂ | " | " | " | " | 202–203 |
| 398 | " | 3-OCH₃ | " | " | " | 207–209 |
| 399 | 2-NO₂ | " | " | " | " | 204–208 |
| 400 | 3,5-(OCH₃)₂ | 2-OCH₃ | " | " | " | 196–198 |
| 401 | 3-OCH₃ | " | " | " | " | 170–172 |
| 402 | 4-OCH₃ | " | " | " | " | 225–227 |
| 403 | 4-CH₃ | " | " | " | " | 225–227 |
| 404 | 2-Cl | " | " | " | " | 223–226 |
| 405 | 3-NO₂ | " | " | " | " | 180–184 |
| 406 | " | 3-OCH₃ | " | " | " | 240–244 |
| 407 | " | 4-OCH₃ | " | " | " | 255–260 |
| 408 | 2,5-F₂ | 4-OCH₃ | H | O | CH₃ | 220–222 |
| 409 | 2-Cl,5-OCH₃ | " | " | " | " | 225–236 |
| 410 | 3-Cl | 3-Cl | " | " | " | 243–244 |
| 411 | 4-Cl | " | " | " | " | 299–300 |
| 412 | 2,5-F₂ | " | " | " | " | 230–233 |
| 413 | 2-NO₂ | " | " | " | " | 273–275 |
| 414 | 3-NO₂ | " | " | " | " | >300 |
| 415 | 2-Cl | 2-Br | " | " | " | 218–220 |
| 416 | " | " | " | " | " | 225–227 |
| 417 | 3-Cl | " | " | " | " | 214–216 |
| 418 | 4-CH₃ | " | " | " | " | 226–229 |
| 419 | 3-CH₃ | " | " | " | " | 227–228 |
| 420 | 2-CH₃ | " | " | " | " | 197–199 |
| 421 | 4-Cl | " | " | " | " | 224–226 |
| 422 | 2-OCH₃ | " | " | " | " | 153–156 |
| 423 | 3-OCH₃ | " | " | " | " | 147–150 |
| 424 | 4-OCH₃ | " | " | " | " | 216–218 |
| 425 | 3,5-(OCH₃)₂ | " | " | " | " | 224–226 |
| 426 | 2,5-F₂ | " | " | " | " | 211–214 |
| 427 | " | " | " | " | " | 211–213 |
| 428 | 2-NO₂ | " | " | " | " | 220–224 |
| 429 | " | " | " | " | " | 201–204 |
| 430 | 3-NO₂ | " | " | " | " | 192–196 |
| 431 | 2-Cl | 2,4-F₂ | " | " | " | 120–121 |
| 432 | " | " | " | " | " | 198–199 |
| 433 | 3,5-(OCH₃)₂ | 2,4-F₂ | H | O | CH₃ | 180–182 |
| 434 | " | 3,4-F₂ | " | " | " | 217–218 |
| 435 | 2-Cl | 4-CH₃ | " | " | " | 230–233 |
| 436 | 3-OCH₃ | " | " | " | " | 230–231 |
| 437 | 3,5-(OCH₃)₂ | " | " | " | " | 223–225 |
| 438 | 2-CH₃ | 2-OCH₃ | " | " | " | 188–191 |

TABLE 1a-continued

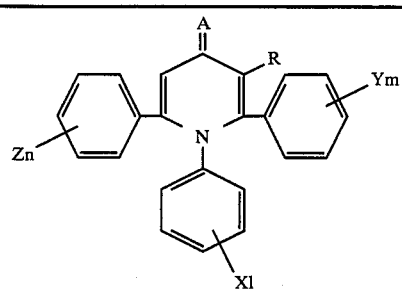

| Compound No. | Xl | Ym | Zn | A | R | Melting point(°C.) |
|---|---|---|---|---|---|---|
| 439 | 3-CH$_3$ | " | " | " | " | 183–185 |
| 440 | 2-OCH$_3$ | " | " | " | " | 194–197 |
| 441 | 2-NO$_2$ | " | " | " | " | 243–245 |
| 442 | 3-Cl | " | " | " | " | 213–215 |
| 443 | 4-Cl | " | " | " | " | 245–248 |
| 444 | 2-Cl | 4-Cl | " | " | " | 218–220 |
| 445 | 2-Cl,3-OCH$_3$ | 4-OCH$_3$ | " | " | " | 222–223 |
| 446 | 3,5-(OCH$_3$)$_2$ | " | " | " | " | 202–204 |
| 447 | 2-F | 2-Br | " | " | " | 220–223 |
| 448 | " | " | " | " | " | 177–179 |
| 449 | 2,3-Cl$_2$ | " | " | " | " | 249–251 |
| 450 | 2-Cl,5-OCH$_3$ | " | " | " | " | 232–235 |
| 451 | 2-Cl | 2-F | " | " | " | 199–200 |
| 452 | " | " | " | " | " | 203–204 |
| 453 | 2-F | " | " | " | " | 190–191 |
| 454 | " | " | " | " | " | 188–189 |
| 455 | 3,5-(OCH$_3$)$_2$ | " | " | " | " | 218–219 |
| 456 | 3-Cl | 4-Cl | " | " | " | 239–241 |
| 457 | 4-Cl | " | " | " | " | 238–240 |
| 458 | 2-CH$_3$ | 4-Cl | H | O | CH$_3$ | 254–256 |
| 459 | 3-CH$_3$ | " | " | " | " | 189–190 |
| 460 | 4-CH$_3$ | " | " | " | " | 194–195 |
| 461 | 2-OCH$_3$ | " | " | " | " | 226–228 |
| 462 | 3-OCH$_3$ | " | " | " | " | 257–259 |
| 463 | 4-OCH$_3$ | " | " | " | " | 261–266 |
| 464 | 2-NO$_2$ | " | " | " | " | 238–239 |
| 465 | 3-NO$_2$ | " | " | " | " | 228–229 |
| 466 | 3,5-(OCH$_3$)$_2$ | 2-Cl,4-OCH$_3$ | " | " | " | 223–224 |
| 467 | 2-CH$_3$,5-OCH$_3$ | 4-OCH$_3$ | " | " | " | 229–231 |
| 468 | 2-CH$_3$,3-OCH$_3$ | " | " | " | " | 216–218 |
| 469 | 3,5-(OCH$_3$)$_2$ | " | " | " | C$_2$H$_5$ | 170–171 |
| 470 | 2-Cl,5-OCH$_3$ | " | " | " | " | 185–187 |
| 471 | 2-Cl | H | 2-Cl | " | CH$_3$ | 164–167 |
| 472 | " | " | 2-F | " | " | 228–231 |
| 473 | " | " | 2-OCH$_3$ | " | " | 208–210 |
| 474 | 2,6-F$_2$ | " | 2-Cl | " | " | 213–215 |
| 475 | 3-Cl | " | " | " | " | 234–237 |
| 476 | 4-Cl | " | " | " | " | 229–230 |
| 477 | 2-CH$_3$ | " | " | " | " | 187–190 |
| 478 | 3-CH$_3$ | " | " | " | " | 215–217 |
| 479 | 4-CH$_3$ | " | " | " | " | 204–205 |
| 480 | 2-OCH$_3$ | " | " | " | " | 184–189 |
| 481 | 3-OCH$_3$ | " | " | " | " | 182–186 |
| 482 | 4-OCH$_3$ | " | " | " | " | 197–200 |
| 483 | 2-F | H | 2-Cl | O | CH$_3$ | 188–190 |
| 484 | 2-CN | " | " | " | " | 217–219 |
| 485 | 2-Cl | " | 3-NO$_2$ | " | " | 291–293 |
| 486 | 2-NO$_2$ | " | 2-Cl | " | " | 217–219 |
| 487 | 3-NO$_2$ | " | " | " | " | 195–196 |
| 488 | 4-NO$_2$ | " | " | " | " | 290–295 |
| 489 | 2,5-F$_2$ | " | " | " | " | 231–233 |
| 490 | 3,5-(OCH$_3$)$_2$ | " | " | " | " | 239–241 |
| 491 | 3-Cl | " | 2-F | " | " | 224–226 |
| 492 | 4-Cl | " | " | " | " | 255–257 |
| 493 | 2-CH$_3$ | " | " | " | " | 183–185 |
| 494 | 3-CH$_3$ | " | " | " | " | 213–214 |
| 495 | 4-CH$_3$ | " | " | " | " | 204–205 |
| 496 | 2-OCH$_3$ | " | " | " | " | 201–202 |
| 497 | 3-OCH$_3$ | " | " | " | " | 206–207 |
| 498 | 4-OCH$_3$ | " | " | " | " | 225–226 |
| 499 | 3,5-(OCH$_3$)$_2$ | " | " | " | " | 226–227 |
| 500 | 2-Cl | " | 4-CH$_3$ | " | " | 232–233 |
| 501 | 3-OCH$_3$ | " | " | " | " | 199–201 |
| 502 | 2,5-F$_2$ | " | 2-F | " | " | 211–212 |

TABLE 1a-continued

| Compound No. | Xl | Ym | Zn | A | R | Melting point(°C.) |
|---|---|---|---|---|---|---|
| 503 | 2-Cl,5-OCH$_3$ | " | " | " | " | 191–192 |
| 504 | 2-Br | " | " | " | " | 218–219 |
| 505 | 2-F | " | " | " | " | 212–213 |
| 506 | 2-Cl | " | 3-CH$_3$ | " | " | 213–215 |
| 507 | 3,5-(OCH$_3$)$_2$ | " | " | " | " | 201–203 |
| 508 | 2-F | H | 3-CH$_3$ | O | CH$_3$ | 211–214 |
| 509 | 2,3-Cl$_2$ | " | 2-F | " | " | 217–218 |
| 510 | 2-NO$_2$ | " | " | " | " | 213–214 |
| 511 | H | 2-Cl | 2-Cl | " | " | 215–218 |
| 512 | " | 4-OCH$_3$ | " | " | " | 244–246 |
| 513 | " | " | 2-F | " | " | 228–231 |
| 514 | 2-Cl | 2-Cl | 2-Cl | " | " | 205–207 |
| 515 | 2-NO$_2$ | " | " | " | " | 189–193 |
| 516 | " | " | " | " | " | 237–245 |
| 517 | 2-Cl | 4-OCH$_3$ | " | " | " | 216–217 |
| 518 | 3,5-(OCH$_3$)$_2$ | " | " | " | " | 185–186 |
| 519 | 2,5-F$_2$ | " | " | " | " | 206–209 |
| 520 | 2-Cl | " | 2-F | " | " | 204–207 |
| 521 | 3,5-(OCH$_3$)$_2$ | " | " | " | " | 176–178 |
| 522 | H | H | H | " | Cl | 285–287 |
| 523 | " | " | " | " | Br | 274–277 |
| 524 | " | " | " | " | I | 275–277 |
| 525 | " | " | " | " | C$_2$H$_5$ | 173–176 |
| 526 | " | " | " | " | C$_3$H—n | 158–160 |
| 527 | " | " | " | " | C$_4$H$_9$—n | 101–103 |
| 528 | " | " | " | " | C$_3$H$_7$—i | 181–184 |
| 529 | " | " | " | " | CH$_2$Cl | 214–216 |
| 530 | " | " | " | " | CH$_2$Br | no measurable |
| 531 | " | " | " | " | CH$_2$OCH$_3$ | 176–180 |
| 532 | " | " | " | " | CH$_2$OH | 196–199 |
| 533 | H | H | H | O | COOH | 257–259 |
| 534 | " | " | " | " | CN | >300 |
| 535 | " | " | " | " | OCH$_3$ | 188–191 |
| 536 | " | " | " | " | CF$_3$ | 222–225 |
| 537 | " | " | " | " | COOC$_2$H$_5$ | 184–187 |
| 538 | " | " | " | " | CH$_2$CH=CH$_2$ | 157–159 |
| 539 | " | " | " | " | —CH$_2$—C$_6$H$_5$ | 161–164 |
| 540 | " | " | " | " | —C$_6$H$_5$ | 210–213 |
| 541 | " | " | " | " | —CH$_2$OC(O)C$_6$H$_5$ | 194–196 |
| 542 | 2-Cl | " | " | S | CH$_3$ | 271–275 |
| 543 | H | " | " | " | " | 264–266 |

TABLE 1b

| Compound No. | Xl | Ym | Zn | A | R | Melting point (°C.) |
|---|---|---|---|---|---|---|
| 544 | 2-Cl,5-OCH₃ | H | 3-CH₃ | O | CH₃ | 202–205 |
| 545 | 2-Cl | 4-F | H | " | " | 235–242 |
| 546 | 2-F | " | " | " | " | 247–249 |
| 547 | 3,5-(OCH₃)₂ | " | " | " | " | 202–204 |
| 548 | 2-Cl, 5-OCH₃ | " | " | " | " | 203–206 |
| 549 | " | 2,4-F₂ | " | " | " | 184–186 |
| 550 | 2-CH₃, 4-OCH₃ | 4-OCH₃ | " | " | " | 179–182 |
| 551 | 2-Cl, 3,5-(OCH₃)₂ | " | " | " | " | 230–232 |
| 552 | 2-Cl | 3,4 —O\CH₂/—O | " | " | " | 237–239 |
| 553 | 3,5-(OCH₃)₂ | " | " | " | " | 247–248 |
| 554 | H | H | 2-CH₂OCH₂CH₂CH₃ | " | " | 118–122 |
| 555 | 2-Cl, 5-OCH₃ | " | 2-CH₂OCH₂CH₃ | " | " | 183–184 |
| 556 | " | 2-F | H | " | " | 223–224 |
| 557 | 2-Cl, 3,5-(OCH₃)₂ | H | 2-F | " | " | 237–238 |
| 558 | 3,5-(OCH₃)₂ | 2-F | " | " | " | 193–194 |
| 559 | 2-Cl, 5-OCH₃ | 3-CH₃ | H | " | " | 212–215 |
| 560 | " | 2-Cl, 4-OCH₃ | " | " | " | 209–211 |
| 561 | " | " | " | " | " | 205–206 |
| 562 | " | 4-CH₃ | " | " | " | 238–239 |
| 563 | 2,5-F₂ | " | " | " | " | 240–243 |
| 564 | 2,3-Cl₂ | 2,4-F₂ | " | " | " | 165–167 |
| 565 | 2,3-Cl₂ | 2,4-F₂ | H | O | CH₃ | 225–227 |
| 566 | 2,5-F₂ | " | " | " | " | 216–218 |
| 567 | " | " | " | " | " | 212–215 |
| 568 | 2-Cl | 3-Cl | " | " | " | 256–260 |
| 569 | 2,3-Cl₂ | " | " | " | " | 253–255 |
| 570 | 2-F | " | " | " | " | 246–248 |
| 571 | 3,5-(OCH₂C≡CH)₂ | H | " | " | " | 157–159 |
| 572 | 2-F | 4-Cl | " | " | " | 235–238 |
| 573 | 3,5-(OCH₃)₂ | " | " | " | " | 208–210 / 212–214 |
| 574 | 2-Cl, 5-OCH₃ | 2-Cl | " | " | " | 220–222 / 238–239 |
| 575 | " | " | " | " | " | 229–230 |
| 576 | 2-Cl, 3,5-(OCH₃)₂ | " | " | " | " | 256–258 |
| 577 | " | " | " | " | " | 256–258 |
| 578 | 2-CH₃, 3-OCH₃ | " | " | " | " | 217–219 |
| 579 | 2-CH₃, 5-OCH₃ | " | " | " | " | 218–221 |
| 580 | 4-Br, 3,5-(OCH₃)₂ | H | " | " | " | >300 |

TABLE 1c

| Compound No. | Xl | Ym | Zn | A | R | Melting point (°C.) |
|---|---|---|---|---|---|---|
| 581 | H | 2-F,4-OCH₃ | H | O | CH₃ | 210–212 |
| 582 | " | 2-CH₃,4-OCH₃ | " | " | " | 180–182 |
| 583 | " | 2-Cl | 2-F | " | " | 177–179 |
| 584 | " | 4-F | " | " | " | 229–232 |
| 585 | " | 2-Cl,4-OCH₃ | " | " | " | 206–209 |
| 586 | 2-Cl,4-OCH₃ | H | H | " | " | 213–215 |
| 587 | 2-F,5-OCH₃ | " | " | " | " | 191–193 |
| 588 | 2-Br,3,5-(OCH₃)₂ | " | " | " | " | 264–265 |
| 589 | 2,3,4-F₃ | " | " | " | " | 209–210 |
| 590 | 2-Cl,3,5-(OCH₃)₂ | " | " | " | C₂H₅ | 168–170 |
| 591 | 2-F,5-OCH₃ | " | 2-F | " | CH₃ | 173–176 |
| 592 | 2-Br,3,5-(OCH₃)₂ | " | " | " | " | 206–210 / 234–237 |
| 593 | 2-Cl,5-OCH₃ | " | 2-Cl | " | " | 186–188 |
| 594 | 2-Cl,3-OCH₃ | " | H | " | " | 270.5–271.5 |
| 595 | " | " | " | " | " | 238–240 |
| 596 | 2-Br,3,5-(OCH₃)₂ | " | " | " | " | 243.5–245.5 |
| 597 | " | " | " | " | " | 227–230 |
| 598 | 3-O—C₃H₇-i | " | " | " | " | 162–164 |
| 599 | 2-F,5-OCH₃ | " | " | " | " | 185–188 |
| 600 | " | " | " | " | " | 169–174 |
| 601 | 2-Cl,5-OCH₃ | " | 2-Br | " | " | 185–194 |
| 602 | 2-Cl,3-OCH₃ | 4-Cl | H | O | CH₃ | 212–215 |
| 603 | 2-Cl,5-OCH₃ | " | " | " | " | 243–245 |
| 604 | 2-Cl,3,5-(OCH₃)₂ | " | " | " | " | 245–247 |

TABLE 1c-continued

| Compound No. | Xl | Ym | Zn | A | R | Melting point(°C.) |
|---|---|---|---|---|---|---|
| 605 | " | 2-F | " | " | " | 240–243 / 247–250 |
| 606 | " | " | " | " | " | 242–243 |
| 607 | " | 4-F | " | " | " | 242–246 / 250–253 |
| 608 | 2-F | 4-OC$_2$H$_5$ | " | " | " | 186–188 |
| 609 | 3-OCH$_3$ | " | " | " | " | 180–184 |
| 610 | 2-Cl | " | " | " | " | 168–170 |
| 611 | 3,5-(OCH$_3$)$_2$ | " | " | " | " | 168–171 |
| 612 | 2-Cl,5-OCH$_3$ | " | " | " | " | 179–182 |
| 613 | 2-Br,3,5-(OCH$_3$)$_2$ | 4-OCH$_3$ | " | " | " | 248–250 |
| 614 | 2-F | 4-OCH$_2$C≡CH | " | " | " | 158–161 |
| 615 | 3-OCH$_3$ | " | " | " | " | 173–175 |
| 616 | 3,5-(OCH$_3$)$_2$ | " | " | " | " | 170–171 |
| 617 | 2-Cl,3,5-(OCH$_3$)$_2$ | 2,4-F$_2$ | " | " | " | 226–230 |
| 618 | " | " | " | " | " | 216–218 |
| 619 | " | 2-Cl,4-OCH$_3$ | " | " | " | 240–243 |
| 620 | " | " | " | " | " | 233–235 |
| 621 | 2-CH$_3$,3-OCH$_3$ | " | " | " | " | 266–269 |
| 622 | " | " | " | " | " | 205–207 |
| 623 | 3,5-(OCH$_3$)$_2$ | 2-CH$_3$,4-OCH$_3$ | " | " | " | 215–217 |
| 624 | " | 2-F,4-OCH$_3$ | " | " | " | 162–163 |
| 625 | 2-Cl,3,5-(OCH$_3$)$_2$ | 4-OCH$_3$ | 2-F | " | " | 232–235 |
| 626 | 2-Cl,5-OCH$_3$ | 4-OCH$_3$ | 2-F | O | CH$_3$ | 243–247 |
| 627 | 2-Cl,3,5-(OCH$_3$)$_2$ | 2-Cl | " | " | " | 256–257 |
| 628 | " | " | " | " | " | 213–215 / 235–236 |
| 629 | 2-Cl,5-OCH$_3$ | " | " | " | " | 200–201 |
| 630 | " | " | " | " | " | 207–208 |
| 631 | 2-Br,3,5-(OCH$_3$)$_2$ | " | " | " | " | 237–239 |
| 632 | " | " | " | " | " | 245–247 |
| 633 | 3,5-(OCH$_3$)$_2$ | " | " | " | " | 184–185 |
| 634 | 2-Cl,3,5-(OCH$_3$)$_2$ | 2-F | " | " | " | 252–254 |
| 635 | " | " | " | " | " | 251–253 |
| 636 | 2-Cl,5-OCH$_3$ | " | " | " | " | 200–201 |
| 637 | " | " | " | " | " | 184–186 |
| 638 | " | 4-F | " | " | " | 194–198 |
| 639 | 3,5-(OCH$_3$)$_2$ | " | " | " | " | 195–200 |
| 640 | 2-Cl,5-OCH$_3$ | 2,4-F$_2$ | " | " | " | 183–185 |
| 641 | " | " | " | " | " | 169–174 |
| 642 | 3,5-(OCH$_3$)$_2$ | " | " | " | " | 170–171 |
| 643 | 2-Cl,5-OCH$_3$ | 2-Cl,4-OCH$_3$ | " | " | " | 252–256 |
| 644 | " | " | " | " | " | 210–212 |
| 645 | 3,5-(OCH$_3$)$_2$ | " | " | " | " | 210–214 |
| 646 | 2-Cl,3,5-(OCH$_3$)$_2$ | 2,4-F$_2$ | " | " | " | 238–240 |
| 647 | " | " | " | " | " | 229–232 |

TABLE 1d

| Compound No. | Xl | Ym | Zn | A | R | Melting point (°C.) |
|---|---|---|---|---|---|---|
| 648 | H | 2-Cl | H | O | C$_2$H$_5$ | 191–194 |
| 649 | " | 4-OCHF$_2$ | " | " | CH$_3$ | 165–166 |
| 650 | 2-Cl, 5-OCH$_3$ | 2,4-F$_2$ | " | " | " | 184–186 |
| 651 | 2-Cl, 3,5-(OCH$_3$)$_2$ | 4-OCH$_3$ | " | " | " | 230–232 |
| 652 | 3,5-(OCH$_3$)$_2$ | H | 2-CH$_2$OC$_2$H$_5$ | " | " | 159–160 |
| 653 | 2-Cl | 3-CH$_3$ | " | " | " | 247–251 |
| 654 | 2-F | " | " | " | " | 228–231 |
| 655 | 3,5-(OCH$_3$)$_2$ | " | " | " | " | 210–211 |
| 656 | H | H | 4-CH$_2$OCH$_3$ | " | " | 145–146 |
| 657 | 3-NHCCH$_3$ (O=) | " | H | " | " | >300 |
| 658 | 2-F | 4-OCH$_2$C≡CH | " | " | " | 158–161 |
| 659 | 3,5-(OCH$_3$)$_2$ | 2-F, 4-OCH$_3$ | 2-F | " | " | 103–105 |
| 660 | H | 2-F | " | " | " | 180–183 |
| 661 | 3-C$_3$H$_7$—i | H | H | " | " | 189–191 |
| 662 |  | " | " | " | " | 177–179 |

TABLE 1d-continued

| Compound No. | Xl | Ym | Zn | A | R | Melting point (°C.) |
|---|---|---|---|---|---|---|
| 663 | 3,5-(OCH$_3$)$_2$ | 2,3-F$_2$ | " | " | " | 227–229 |
| 664 | " | 3,5-(CH$_3$)$_2$ | " | " | " | 242–244 |
| 665 | " | 2-F | 2-F | S | " | 226–228 |
| 666 | " | 4-OC$_3$H$_7$ | H | O | " | 149–150 |
| 667 | 2-Cl, 5-OCH$_3$ | " | " | " | " | 189–190 |
| 668 | " | H | 3-F | " | " | 236–239 |
| 669 | " | " | H | " | Cl | 255–256 |
| 670 | " | " | 2-F | S | CH$_3$ | 243–245 |
| 671 | 2-O-C$_6$H$_5$ | " | H | O | " | {198–200, 201–203} |
| 672 | 4-O-C$_6$H$_5$ | " | " | " | " | 233–237 |
| 673 | 2-Cl, 5-OCH$_3$ | H | H | S | CH$_3$ | 251–253 |
| 674 | H | 4-C(=CH$_2$)CH$_3$ | " | O | " | 253–254 |
| 675 | 3,5-(OCH$_3$)$_2$ | " | " | " | " | 195–196 |
| 676 | 2-Cl,3,5-(OCH$_3$)$_2$ | " | " | " | " | 208–209 |
| 677 | " | H | 2-F | S | " | 209–211 |
| 678 | 3,5-(OCH$_3$)$_2$ | " | " | " | " | 241–243 |
| 679 | " | 2,4-F$_2$ | " | " | " | 216–217 |
| 680 | " | H | H | " | " | 259–261 |
| 681 | 2-Cl,5-OCH$_3$ | 4-OCH$_2$C≡CH | " | O | " | 192–193 |
| 682 | H | 4-OC$_4$H$_9$ | " | O | " | 150–151 |
| 683 | 2-Cl, 5-OCH$_3$ | " | " | " | " | 179–183 |
| 684 | 3,5-(OCH$_3$)$_2$ | " | " | " | " | 118–119 |
| 685 | 2-CH$_3$, 3-OCH$_3$ | 2,4-F$_2$ | " | " | " | 208–209 |
| 686 | H | 2,4-F$_2$ | 2-F | " | " | 213–214 |
| 687 | " | 2-F | 2-Cl | " | " | 196–200 |
| 688 | 2-F, 4-Cl | H | H | " | " | 216–218 |
| 689 | 2-Cl, 4-F | " | " | " | " | 268–269 |
| 690 | 3,5-(OCH$_3$)$_2$ | " | 2,3-F$_2$ | " | " | 218–219 |
| 691 | H | " | H | " | C≡CH | 250–253 |
| 692 | " | " | " | " | C≡C—Si—(CH$_3$)$_3$ | 202–203 |
| 693 | 3,5-(OCH$_3$)$_2$ | 2-F | 2-F | " | Cl | 236–238 |
| 694 | 3-O-C$_6$H$_5$ | H | H | " | CH$_3$ | 157–159 |
| 695 | 2-NO$_2$, 3,5-(OCH$_3$)$_2$ | " | " | " | " | {255–258, 264–266} |
| 696 | 2-Cl, 5-OCH$_3$ | 2-Cl | " | S | " | 269–271 |
| 697 | 2-Cl, 5-OCH$_3$ | 2-Cl | H | S | CH$_3$ | 251–253 |
| 698 | 2-Cl, 3,5-(OCH$_3$)$_2$ | H | " | " | " | 255–258 |
| 699 | 4-NHC(O)CH$_3$ | " | " | O | " | >300 |
| 700 | H | 2,4-F$_2$ | 2-Cl | " | " | 193–194 |
| 701 | " | H | 2-F, 3-Cl | " | " | 199–200 |
| 702 | " | 2-F | 2,4-F$_2$ | " | " | 182–183 |
| 703 | 2-NHC(O)CH$_3$ | H | H | " | " | 283–284 |
| 704 | 2-N(CH$_3$)COCH$_3$ | " | " | " | " | {239–241, 248–249} |

TABLE 1d-continued

| Compound No. | Xl | Ym | Zn | A | R | Melting point (°C.) |
|---|---|---|---|---|---|---|
| 705 | 3-N(CH₃)—COCH₃ | " | " | " | " | 188–189 |
| 706 | 4-N(CH₃)—COCH₃ | " | " | " | " | >300 |
| 707 | 3-NHCH₃ | " | " | " | " | 282–283 |
| 708 | 4-NHCH₃ | " | " | " | " | 248–249 |
| 709 | H | 4-O-C₆H₅ | | " | " | 262–265 |
| 710 | 3,5-(OCH₃)₂ | 4-O-C₆H₅ | | " | " | 211–212 |
| 711 | H | H | 4-O-C₆H₅ | " | " | 209–210 |
| 712 | " | 2-Cl | 2-F | S | " | 196–199 |
| 713 | 3,5-(OCH₃)₂ | 4-OCH₃ | H | " | " | 227–232 |
| 714 | " | 2-Cl | " | " | " | 245–249 |
| 715 | H | 4-C(O)NH₂ | " | O | " | >300 |
| 716 | H | 2-F, 3-Cl | H | O | CH₃ | 216–217 |
| 717 | " | 3,5-F₂ | " | " | " | 205–206 |
| 718 | " | 2-F | 2-F | " | Cl | 219.5–220 |
| 719 | 3,5-F₂ | H | H | " | CH₃ | 268–269 |
| 720 | 2-OCH₂C≡CH | " | " | " | " | 165–167 |
| 721 | 2-Cl, 5-NH₂ | " | " | " | " | >300 |
| 722 | 2-Cl, 5-NHC(O)CH₃ | " | " | " | " | >300 |
| 723 | 2-Cl, 5-N(CH₃)C(O)CH₃ | " | " | " | " | 239–240 |
| 724 | 2-Cl, 5-NH—CH₃ | " | " | " | " | 235–237 |
| 725 | 2,3-OCH₂O (methylenedioxy) | " | " | " | " | 203–205 |
| 726 | H | " | 2,3-OCH₂O | " | " | 181–183 |
| 727 | 2-Cl, 5-OCH₃ | " | " | " | " | 183–185 |
| 728 | 3,5-(OCH₃)₂ | " | " | " | " | 228–229 |
| 729 | H | 2,3-(CH₃)₂ | H | " | " | 250–254 |
| 730 | 2-Cl | H | 2-CH₃ | " | " | 194–197 |
| 731 | 2-Cl, 5-OCH₃ | " | " | " | " | 194–197 |
| 732 | 3,5-(OCH₃)₂ | " | " | " | " | 215–217 |
| 733 | 3-OCH₃ | 2-F | H | " | " | 161–163 |
| 734 | " | " | 2-F | " | " | 194–195 |
| 735 | 3,5-(OCH₃)₂ | " | 2,4-F₂ | " | " | 210–212 |
| 736 | H | 4-CH₂OCH₃ | H | " | " | 174–175 |
| 737 | " | 4-I | " | " | " | 253–255 |
| 738 | 3-OCH₃ | 2-F | 2,4-F₂ | O | CH₃ | 169–171 |
| 739 | " | 2-Cl | 2-F | " | " | 173–174 |
| 740 | 2-Cl | H | 4-CH₂OCH₃ | " | " | 177–179 |

TABLE 1d-continued

| Compound No. | Xl | Ym | Zn | A | R | Melting point (°C.) |
|---|---|---|---|---|---|---|
| 741 | 2-Cl, 5-OCH₃ | " | " | " | " | 184–185 |
| 742 | 3,5-(OCH₃)₂ | " | " | " | " | 160–162.5 |
| 743 | H | 2-Cl | 2-F | " | " | 223–224 |
| 744 | 2-Cl, 5-N(CH₃)₂ | H | H | " | " | 219–221 |
| 745 | 2-Cl | " | 2,3-(—O—CH₂—O—) | " | " | 237–240 |
| 746 | H | " | 3-F, 4-OCH₃ | " | " | 180–181 |
| 747 | " | 2,6-F₂, 4-Br | H | " | " | 189–190 |
| 748 | H | 2-Cl | 2,4-F₂ | " | " | 165–168 |
| 749 | 3,5-(OCH₃)₂ | " | " | " | " | 205–206 |
| 750 | H | H | 3,5-F₂ | " | " | 234–236 |
| 751 | " | " | 2,6-F₂, 4-Br | " | " | 210–215 |
| 752 | 2, Cl, 4-NO₂ | 4-F | H | " | " | 114–120 |
| 753 | 3-N(CH₃)₂ | H | " | " | " | 197–199 |
| 754 | 2-F, 5-N(CH₃)₂ | " | " | " | " | 193–195 |
| 755 | 2-Cl, 5-OCH₃ | 3,4-(—O—CH₂—O—) | " | " | " | 244–246 |
| 756 | 4-OCH₂C≡CH | H | " | " | " | 263–265 |
| 757 | 4-OC₃H₇ | " | " | " | " | 189–190 |
| 758 | 2,3-(—CH₂—O—) | " | " | " | " | 265–268 |
| 759 | H | " | 3,4-F₂ | " | " | 188–189 |
| 760 | H | 2-F | 2,3-F₂ | O | CH₃ | 151–153 |
| 761 | " | 2-Cl | " | " | " | 206–207 |
| 762 | 2-F, 5-NH₂ | H | H | " | " | 290–292 |
| 763 | 2-CH₃, 3-NO₂, 5-OCH₃ | " | " | " | " | 241–242 |
| 764 | H | 2,3-(—O—CH₂—O—) | " | " | " | 162–164 |
| 765 | 2-Cl | " | " | " | " | 156–160 |
| 766 | 3,5-(OCH₃)₂ | " | " | " | " | 164–165 |
| 767 | H | H | 2-Cl, 3,5-(OCH₃)₂ | " | " | 235–236 |
| 768 | 2-Cl | " | " | " | " | 276–277 / 287–288 |
| 769 | 2-Cl, 5-OCH₃ | " | " | " | " | 239–240 / 244–245 |
| 770 | 3,5-(OCH₃)₂ | " | " | " | " | 222–223 |
| 771 | | | | | | |
| 772 | H | 2-NO₂ | H | " | " | 242–243 |
| 773 | " | 3-NO₂ | " | " | " | 244–246 |

TABLE 1d-continued

| Compound No. | Xl | Ym | Zn | A | R | Melting point (°C.) |
|---|---|---|---|---|---|---|
| 774 | " | 4-NO$_2$ | " | " | " | 206–207 |
| 775 | " | H | 2-NO$_2$ | " | " | 161–164 |
| 776 | 2-Cl | " | " | " | " | 184–187 / 199–202 |
| 777 | 3,5-(OCH$_3$)$_2$ | " | " | " | " | 256–258 |
| 778 | H | 2-Cl | " | " | " |  |
| 779 | " | 2-F | " | " | " |  |
| 780 | 2-Cl | 2-NO$_2$ | H | " | " |  |
| 781 | 3,5-(OCH$_3$)$_2$ | 2-NO$_2$ | H | O | CH$_3$ |  |
| 782 | 2-Cl | 3-NO$_2$ | " | " | " |  |
| 783 | 3,5-(OCH$_3$)$_2$ | " | " | " | " |  |
| 784 | 2-Cl | 4-NO$_2$ | " | " | " |  |
| 785 | 3,5-(OCH$_3$)$_2$ | " | " | " | " |  |
| 786 | H | 2-NO$_2$ | 2-Cl | " | " |  |
| 787 | " | " | 2-F | " | " |  |
| 788 | 3-OCH$_3$ | 2-Cl | 2,4-F$_2$ | " | " | 159–160 |
| 789 | 3-OCH$_3$ | 2,4-F$_2$ | H | " | " | 168–169 |
| 790 | " | " | 2-F | " | " | 136.5–138 |
| 791 | " | " | 2,4-F$_2$ | " | " | 137–138 |
| 792 | 2,5-Cl$_2$ 3-CF$_3$ | H | H | " | " | 245–255 |
| 793 | 3,5-(OCH$_3$)$_2$ | 2-F | 2-F | " | CH$_2$OC$_2$H$_5$ | 189–191 |
| 794 | 3,5-(OCH$_3$)$_2$ | " | " | " | 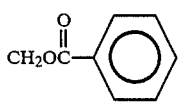 | 88–91 |
| 795 | " | " | " | " | CH$_2$OH | 162–164 |
| 796 | 3-O— 4— | H | H | " | CH$_3$ | 252–253 |
| 797 | H | H | H | " | CH$_2$F | 180–181 |

In Table 1a–Table 1d, when "H" is given in the columns of "X$_l$", "Y$_m$" and/or "Z$_n$", this means that the value of l, m and/or n is or are zero, respectively.

In Table 1a, Compound 2 is a salt with ⅓ HCl, Compound 308 a salt with ½ HCl, and Compound 446 a salt with

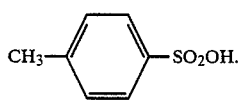

CH$_3$—⟨⟩—SO$_2$OH.

Further, pairs of Compound 335 and Compound 336; Compound 338 and Compound 339; Compound 365 and Compound 364; Compound 366 and Compound 367; Compound 368 and Compound 369; Compound 415 and Compound 416; Compound 426 and Compound 427; Compound 428 and Compound 429; Compound 431 and Compound 432; Compound 451 and Compound 452; Compound 453 and Compound 454; and Compound 515 and Compound 516 are respectively in the relationship of atrop-isomers. Compound 337 is a mixture of isomers.

In Table 1b, pairs of Compound 560 and Compound 561; Compound 564 and Compound 565; Compound 566 and Compound 567; Compound 574 and Compound 575; and Compound 576 and Compound 577 are respectively in the relationship of atrop-isomers. Compound 580 showed the following spectrum peaks:-

IR spectrum (KBr, cm$^{-1}$): 1620, 1230, 1020,

NMR spectrum (CDCl$_3$, δ ppm): 6.00 (2H, s), 6.58(1H, s), 7.00–7.40(10H, m).

In Table 1c, Compound 610 is a hydrate with ½ H$_2$O.

Further, pairs of Compound 594 and Compound 595; Compound 596 and Compound 597; Compound 599 and Compound 600; Compound 605 and Compound 606; Compound 617 and Compound 618; Compound 619 and Compound 620; Compound 621 and Compound 622; Compound 627 and Compound 628; Compound 629 and Compound 630; Compound 631 and Compound 632; Compound 634 and Compound 635; Compound 636 and Compound 637; Compound 640 and Compound 641; Compound 643 and Compound 644; and Compound 646 and Compound 647 are respectively in the relationship of atrop-isomers.

In Table 1d, a pair of Compound 696 and compound 697 is in the relationship of atrop-isomers. Further, Compound 695, Compound 704 and Compound 776 include different crystalline forms, respectively.

Amongst the compounds of formula (I) according to this invention, the compounds of the formulae listed below are most preferred:

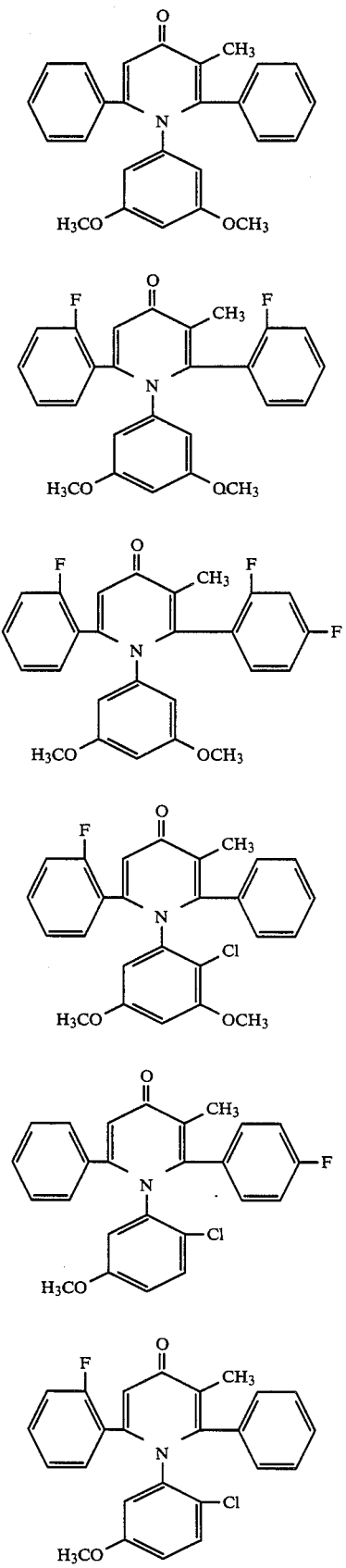

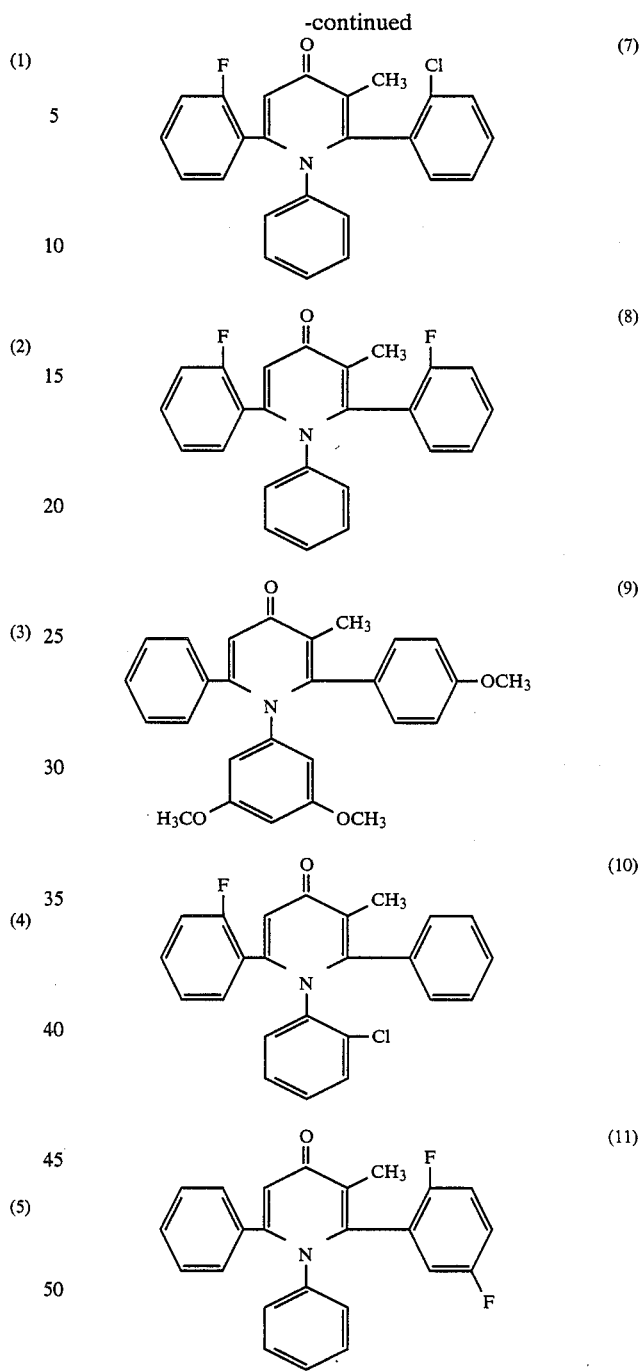

Next, some examples of the compounds of formula (I) of this invention were examined by certain analytical instruments to investigate their characteristic absorptions of the infrared absorption spectrum (IR spectrum) and nuclear magnetic resonance absorption spectrum (NMR spectrum). The results obtained are summarized in Table 2 below.

TABLE 2

| Compound No. | Analytical method | Characteristics |
|---|---|---|
| 28 | IR-spectrum (KBr, cm$^{-1}$) | 2900–2300, 1615 |
| | NMR-spectrum | Not measurable due to |

TABLE 2-continued

| Compound No. | Analytical method | Characteristics |
|---|---|---|
| 29 | IR-spectrum (KBr, cm$^{-1}$) | insolubility in solvents 2800–2300, 1610 |
|  | NMR-spectrum (DMSO—d$_6$, δ ppm) | 1.73(3H,s), 6.30–6.85(6H,m), 7.67(10H,s) |
|  | IR-spectrum (KBr, cm$^{-1}$) | 1615, 1275, 1240 |
| 30 | NMR-spectrum | Not measurable due to insolubility in volvents |
|  | Mass-spectrum (m/z) | 353 (M$^+$) |
|  | IR-spectrum (KBr, cm$^{-1}$) | 1620 |
| 38 | NMR-spectrum (DMSO—d$_6$, δ ppm) | 1.63(3H,s), 5.20(2H.bs) 5.90–6.90(5H,m), 7.00–7.63(10H,m) |
|  | Mass-spectrum (m/z) | 352 (M$^+$) |
|  | IR-spectrum (KBr, cm$^{-1}$) | 3420, 3300, 1620, 1275 |
| 40 | NMR-spectrum | Not measurable due to insolubility in solvents |
|  | IR-spectrum (KBr, cm$^{-1}$) | 1610, 1050 |
| 47 | NMR-spectrum (CDCl$_3$, δ ppm) | 1.93(3H,s), 2.27(3H,s), 6.57(1H,s), 6.90–7.30(14H,m) |
|  | IR-spectrum (KBr, cm$^{-1}$) | 3200, 1620 |
| 64 | NMR-spectrum (CDCl$_3$, δ ppm) | 1.87(3H,s), 2.98(1H,s), 6.49(1H,s), 6.60–7.20(14H,m) |
|  | IR-spectrum (KBr, cm$^{-1}$) | 1625 |
| 112 | NMR-spectrum | Not measurable due to insolubility in solvents |
|  | Mass-spectrum (m/z) | 385 (M$^+$) |
|  | IR-spectrum (KBr, cm$^{-1}$) | 1625, 1520, 1350, 850 |
| 140 | NMR-spectrum | Not measurable due to insolubility in solvents |
|  | Mass-spectrum (m/z) | 396 (M$^+$) |
|  | IR-spectrum (KBr, cm$^{-1}$) | 3150, 1605, 1600–1440, 1160, 765, 700 |
| 141 | NMR-spectrum | Not measurable due to insolubility in solvents |
|  | IR-spectrum (KBr, cm$^{-1}$) | 1620 |
| 163 | NMR-spectrum (CDCl$_3$, δ ppm) | 6.70(1H,s), 6.80–7.47 (14H,m) |
|  | IR-spectrum (KBr, cm$^{-1}$) | 3500–3200, 1620 |
| 204 | NMR-spectrum (CDCl$_3$/DMSO-d$_6$, δ ppm) | 1.77(3H,s), 6.23(1H,s), 6.50–7.40(14H,m) |
|  | IR-spectrum (KBr, cm$^{-1}$) | 3050, 1600, 1585–1480, 1290, 770, 700 |
| 205 | NMR-spectrum (CDCl$_3$/DMSO-d$_6$, δ ppm) | 1.90(3H,s), 6.50–7.50(16H,m) |
|  | IR-spectrum (KBr, cm$^{-1}$) | 3400, 1605 |
| 206 | NMR-spectrum (DMSO-d$_6$, δ ppm) | 1.76(3H,s), 6.24(1H,s), 6.40–7.50(14H,m) |
|  | IR-spectrum (KBr, cm$^{-1}$) | 3120, 2980, 1720, 1615, 1270, 750 |
| 272 | NMR-spectrum (CDCl$_3$, δ ppm) | 1.33(3H,t), 2.00(3H,s), 4.33 (2H,q), 7.00–7.95(15H,m) |
|  | IR-spectrum | 3050, 1600, 1590–1440, |
| 274 | (KBr, cm$^{-1}$) | 1280, 750, 690 |
|  | NMR-spectrum (CDCl$_3$, δ ppm) | 1.80(3H,s), 6.30–7.30(16H,m) |
|  | IR-spectrum (KBr, cm$^{-1}$) | 3800–2200, 1620, 1295, 760 |
| 275 | NMR-spectrum (DMSO-d$_6$, δ ppm) | 1.66(3H,s), 6.30(1H,s), 6.50–7.40(15H,m) |
|  | IR-spectrum (KBr, cm$^{-1}$) | 3050, 3000–2200, 1700, 1610, 770 |
| 295 | NMR-spectrum (DMSO-d$_6$, δ ppm) | 1.90(3H,s), 6.90–7.90(16H,m) |
|  | IR-spectrum (KBr, cm$^{-1}$) | 3400, 3200–1800, 1705, 1610, 1230 |
| 296 | NMR-spectrum (CDCl$_3$/DMSO-d$_6$, δ ppm) | 1.75(3H,s), 6.33(1H,s), 7.00–8.20(15H,m) |
|  | IR-spectrum (KBr, cm$^{-1}$) | 1620, 1305, 1150 |
| 299 | NMR-spectrum (CDCl$_3$, δ ppm) | 1.90(3H,s), 3.10(3H,s), 6.80–8.00(14H,m), 8.40(1H,s) |
|  | IR-spectrum (KBr, cm$^{-1}$) | 1615 |
| 306 | NMR-spectrum (CDCl$_3$, δ ppm) | 1.89(3H,s), 6.42(1H,s), 6.67–7.33(13H,m) |
|  | IR-spectrumrm (KBr, cm$^{-1}$) | 1627 |
| 326 | NMR-spectrum (CDCl$_3$, δ ppm) | 1.87(3H,s), 6.45(1H,s), 6.65–7.33(13H,m) |
|  | IR-spectrum (KBr, cm$^{-1}$) | 3450, 1610 |
| 331 | NMR-spectrum (DMSO-d$_6$, δ ppm) | 1.76(3H,s), 6.25(1H,s), 6.40–7.50(13H,m) |
|  | IR-spectrum (KBr, cm$^{-1}$) | 3300, 1600 |
| 332 | NMR-spectrum (CD$_3$OD/DMSO-d$_6$ δ ppm) | 1.76(3H,s), 6.00(1H, bs), 6.25(1H,s), 6.80–7.20(10H,m) |
|  | IR-spectrum (KBr, cm$^{-1}$) | 1620, 1550, 1350 |
| 379 | NMR-spectrum (CDCl$_3$, δ ppm) | 1.80(3H,s), 6.50(1H,s) 6.80–7.80(13H,m) |
|  | IR-spectrumn (KBr, cm$^{-1}$) | 3050, 1605, 1580–1430, 1150, 760, 700 |
| 391 | NMR-spectrum | Not measurable due to insolubility in solvents |
|  | IR-spectrum (KBr, cm$^{-1}$) | 1625, 1530, 1350, 855 |
| 414 | NMR-spectrum | Not measurable due to insolubility in solvents |
|  | Mass-spectrum (m/z) | 416 (M$^+$) |
|  | IR-spectrum (KBr, cm$^{-1}$) | 1620 |
| 530 | NMR-spectrum (CDCl$_3$, δ ppm) | 4.03(2H,s), 6.30(1H,s), 6.60–7.90(15H,m) |
|  | Mass-spectrum (m/z) | 415 (M$^+$) |
|  | IR-spectrum (KBr, cm$^{-1}$) | 2230, 1630 |
| 534 | Mass-spectrum (m/z) | 348 (M$^+$), 320 |

Descriptions will next be made of the production of the compounds of formula (I) according to this invention.

PROCESS (a)

The compounds of this invention may each be produced by reacting a 1,5-diphenylpentanetrions derivative represented by the general formula (II):

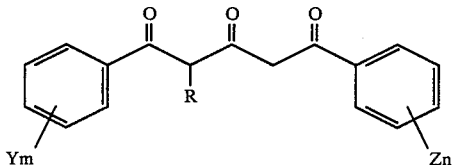

wherein Y, Z, R, m and n have the same meanings as defined above, or a tautomer thereof, with an aniline derivative represented by the general formula (III):

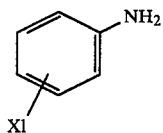

wherein X and l have the same meanings as defined above.

The tautomers of the above compound (II) are represented by the following formulae:

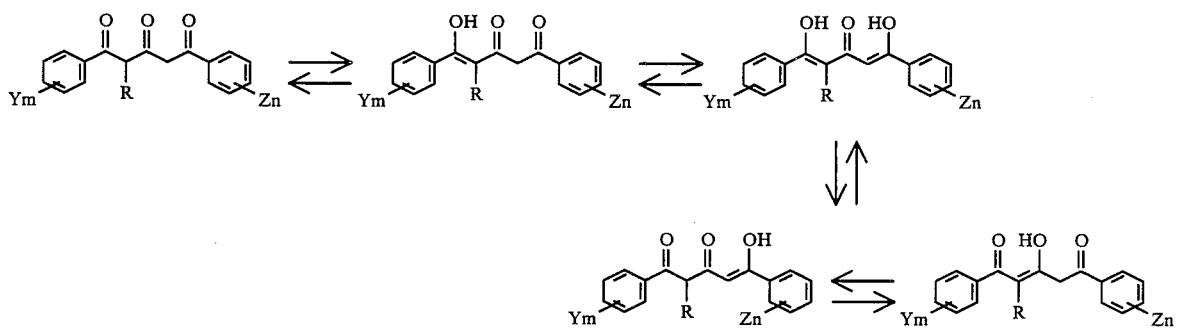

The trione derivative of the formula (II) above can usually be prepared by condensing a 1-benzoyl-1-methylacetone derivative with a benzoic ester derivative in a suitable solvent, for example, tetrahydrofuran, diethyl ether or dimethoxyethane in the presence of a base such as sodium hydride or sodium methylate added thereto.

For example, 1,5-diphenyl-2-methylpentane-1,3,5-trione can be prepared from 1-benzoyl-1-methylacetone and methyl benzoate. It is also possible to prepare 1-(2-chlorophenyl)-2-methyl-5-phenylpentane-1,3,5-trione from 1-(2-chlorobenzoyl)-1-methylacetone and methyl benzoate; 5-(2-chlorophenyl)-1-(4-methoxyphenyl)-3-methylpentane-1,3,5-trione from 1-(4-methoxybenzoyl)-1-methylacetone and methyl 2-chlorobenzoate; and 2-benzyl-1,5-diphenylpentane-1,3,5-trione from 1-benzoyl-1-benzylacetone and methyl benzoate.

In the Process (a), the reaction between the pentanetrione of the formula (II) or its tautomer and the aniline derivative of the formula (III) may be conducted generally by dissolving or suspending both the reactants in a suitable solvent, for example, a hydrocarbon such as benzene, toluene or xylene, a halogenated hydrocarbon such as chlorobenzene, methylene chloride or chloroform, an ether such as diisopropyl ether, tetrahydrofuran or dioxane, a ketone such as acetone, methyl ethyl ketone or cyclohexanone, an ester such as ethyl acetate, a nitrile such as acetonitrile, an amide such as N,N-dimethylformamide, N,N-dimethylacetamide or N-methylpyrrolidone, dimethylsulfoxide, acetic acid, or the like. As an alternative, the reaction may also be conducted without any solvent. It is however preferable to carry out the reaction by dissolving the reactants in xylene or chlorobenzene. Here, the reaction may be allowed to proceed with or without addition of one or more suitable reaction aids. As usable reaction aids, may be mentioned suitable acids, for example, mineral acids such as sulfuric acid and hydrochloric acid, organic acids such as p-toluene-sulfonic acid and triflouromethanesulfonic acid, and Lewis acids such as boron triflouride, aluminum chloride and titanium tetrachloride. In addition, the reaction may also be allowed to proceed while collecting the resultant water in a Dean-Stark trap.

Depending on the kinds of an acid and a solvent to be employed, the reaction may also be conducted in the presence of a dehydrating agent such as molecular sieve. When p-toluenesulfonic acid is used in dimethylsulfoxide, for instance, Molecular Sieves 5-A may be used. The molecular sieve can be used generally in an amount of 2–200 g, preferably, 50–200 g per 0.1 mole of the 1,5-diphenylpentanetrione derivative (II). The reaction may be carried out at a desired temperature between the solidifying point of the solvent and its boiling point, preferably, at a temperature in a range of from 10° C. to the boiling point of the solvent.

After completion of the reaction, the acid or molecular sieve is removed respectively by washing it with water and an alkali solution or by filtration or the like. Upon removal of the solvent by distillation subsequent to extraction of the reaction product with chloroform, the compound of this invention can be obtained. The compound of this invention may be purified by recrystallizing same from acetone, methanol, ethanol, benzene, toluene, diisopropyl ether, ethyl acetate, chloroform, hexane or the like, or subjecting same to chromatography on a silica gel column if necessary.

PROCESS (b)

The compounds of this invention may also be produced by cyclizing a 5-anilino-1,5-diphenyl-4-pentene-1,3-dione derivative represented by the general formula (IV) or (V):

The tautomers of the above compound (IV) are represented by the geneal formulae:

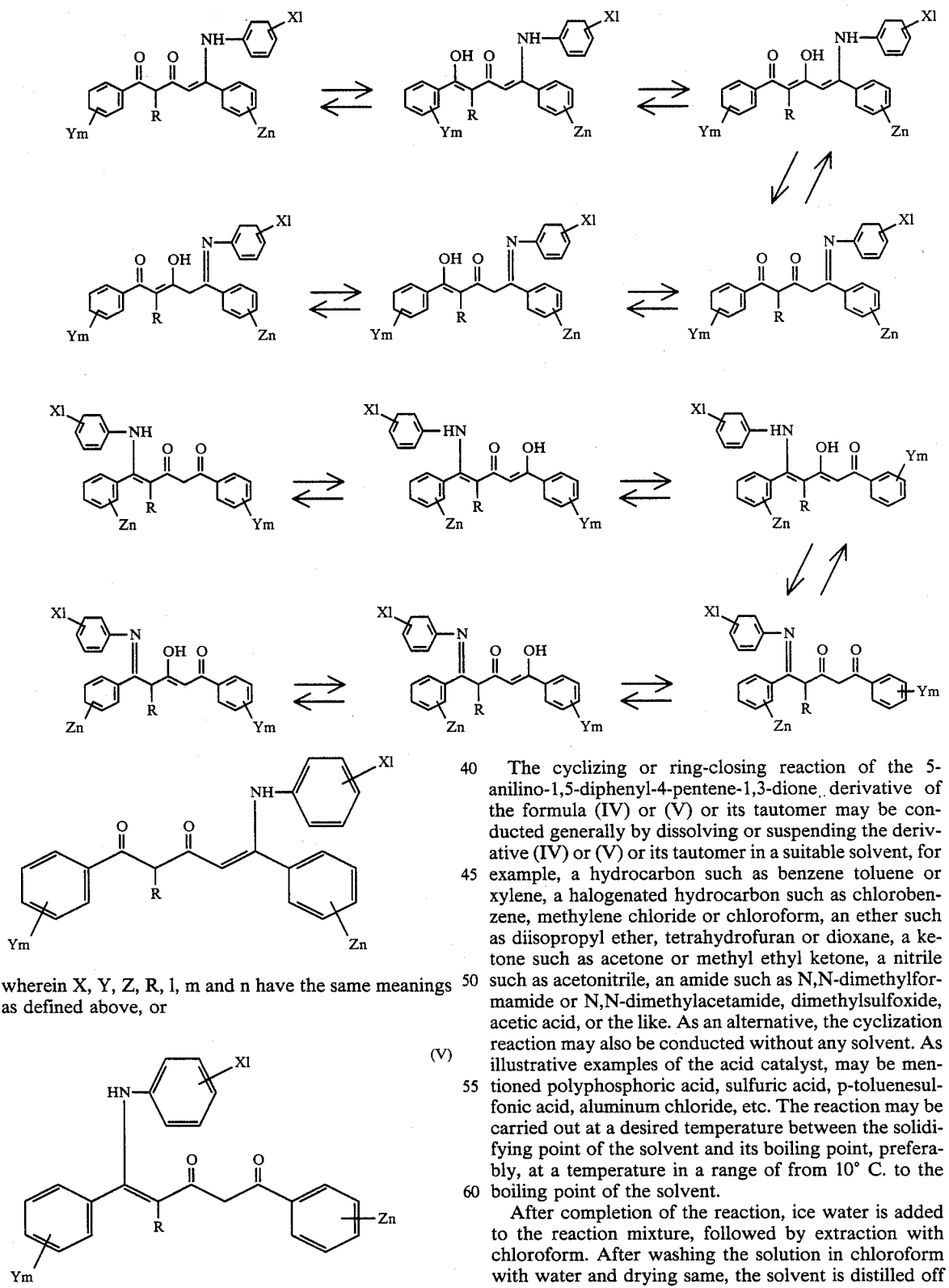

wherein X, Y, Z, R, l, m and n have the same meanings as defined above, or wherein X, Y, Z, R, l, m and n have the same meanings as defined above, or a tautomer thereof in the presence of an acid catalyst.

The cyclizing or ring-closing reaction of the 5-anilino-1,5-diphenyl-4-pentene-1,3-dione derivative of the formula (IV) or (V) or its tautomer may be conducted generally by dissolving or suspending the derivative (IV) or (V) or its tautomer in a suitable solvent, for example, a hydrocarbon such as benzene toluene or xylene, a halogenated hydrocarbon such as chlorobenzene, methylene chloride or chloroform, an ether such as diisopropyl ether, tetrahydrofuran or dioxane, a ketone such as acetone or methyl ethyl ketone, a nitrile such as acetonitrile, an amide such as N,N-dimethylformamide or N,N-dimethylacetamide, dimethylsulfoxide, acetic acid, or the like. As an alternative, the cyclization reaction may also be conducted without any solvent. As illustrative examples of the acid catalyst, may be mentioned polyphosphoric acid, sulfuric acid, p-toluenesulfonic acid, aluminum chloride, etc. The reaction may be carried out at a desired temperature between the solidifying point of the solvent and its boiling point, preferably, at a temperature in a range of from 10° C. to the boiling point of the solvent.

After completion of the reaction, ice water is added to the reaction mixture, followed by extraction with chloroform. After washing the solution in chloroform with water and drying same, the solvent is distilled off to afford the compound (I) of this invention. The compound of this invention may be purified by its recrystallization from acetone, methanol, ethanol, benzene, toluene, diisopropyl ether, ethyl acetate, chloroform, hexane or the like or its chromatography on a silica gel column if necessary.

PROCESS (c)

The compound of this invention can also be produced by reacting a phenylpropiolic ester derivative represented by the general formula (VI):

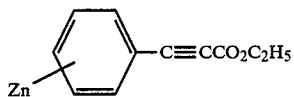

(VI)

wherein Z and n have the same meanings as defined above, with an N-phenyl-1-phenylethaneimine derivative represented by the general formula (VII):

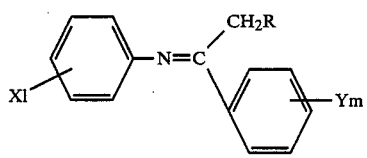

(VII)

wherein X, Y, Z, R, l and m have the same meanings as defined above, in the presence of a Lewis acid such as aluminum chloride or titanium tetrachloride.

Upon conducting the reaction in accordance with the Process (c), the phenylpropiolic ester derivative of the formula (VI) and the N-phenyl-1-phenylethaneimine derivative of the formula (VII) are dissolved or suspended in a suitable solvent, for example, benzene, toluene, xylene, chlorobenzene, dimethylsulfoxide or the like. The reaction may also be carried out without any solvent. It is however preferable to dissolve both the reactants in toluene and then to add 0.5–5 equivalents of a Lewis acid as a reaction aid. As the Lewis acid, may be used aluminum chloride, titanium tetrachloride, boron triflouride, boron trichloride or the like. It is preferable to add 1 equivalent of aluminum chloride.

After completion of the reaction, the reaction mixture is washed successively with an aqueous solution of hydrochloric acid, water and an alkali solution. After extraction with chloroform, the resultant chloroform solution is dried and the solvent is then distilled off to obtain the compound of this invention. If necessary, the compound of this invention can be purified by subjecting it to chromatography on a silica gel column for its crystallization and then recrystallizing same from acetone, methanol, benzene, ethyl acetate, chloroform or the like. When the reaction mixture is washed only with dilute hydrochloric acid and water and is not washed with an aqueous alkali solution subsequent to the completion of the reaction, the compound of the present invention is obtained in the form of its hydrochloric acid salt. For instance, in the case of 2-(2-bromophenyl)-3-methyl-1,6-diphenyl-4(1H)-pyridinone as obtained without washing the reaction mixture with an aqueous alkali solution, this product showed it NMR spectrum, of which the peak corresponding to the C-5 proton shifted to a lower magnetic field as compared with usual pyridinone derivatives, and the elemental analysis indicated the inclusion of ½ HCl. From this, it was confirmed that the product was the hydrochloride salt.

PROCESS (d)

Using as starting compound such a 4(1H)-pyridinone derivatives which have been prepared in the above-described procedures, other 4-(1H)-pyridinone derivatives can also be produced therefrom.

For example, when 2-(4-methoxyphenyl)-3-methyl-1,6-diphenyl-4(1H)-pyridinone is either dissolved or suspended in a suitable solvent, e.g., methylene chloride, benzene or chloroform, and a Lewis acid such as boron tribromide, boron trichloride or the like is then added to the resulting solution to conduct a reaction, 2-(4-hydroxyphenyl)-3-methyl-1,6-diphenyl-4(1H)-pyridinone is produced.

Further, upon dissolution of the 2-(4-hydroxyphenyl)-3-methyl-1,6-diphenyl-4-(1H)-pyridinone as above in a suitable solvent, for example, dimethylsulfoxide, dimethylacetamide, dimethylformamide or acetone, followed by reaction with an alkyl halide, alkoxyalkyl halide, an alkenyl halide or the like, the correspondingly substituted 4(1H)-pyridinone derivative is produced.

For example, the reaction with ethyl iodine gives 2-(4-ethoxyphenyl)-3-methyl-1,6-diphenyl-4-(1H)-pyridinone, and the reaction with methoxymethyl chloride provides the 2-(4-methoxymethoxyphenyl)-3-methyl-1,6-diphenyl-4-(1H)-pyridinone.

Furthermore when 1-(2-nitrophenyl)-3-methyl-2,6-diphenyl-4(1H)-pyridinone is reduced with hydrogen, ammonium formate or the like in the presence of a palladium black catalyst, 1-(2-aminophenyl)-3-methyl-2,6-diphenyl-4-(1H)-pyridinone can be prepared.

Moreover, by reacting 3-methyl-1-(4methylthiophenyl)-2,6-diphenyl-4(1H)-pyridinone with a suitable oxidizing agent, for example, m-chloroperbenzoic acid or Oxone in a suitable solvent such as methylene chloride or an aqueous solution of chloroform-methanol, 1-(4-methanesulfinylphenyl)-3-methyl-2,6-diphenyl-4(1H)-pyridinone or 1-(4-methanesulfonylphenyl)-3-methyl-2,6-diphenyl-4(1H)-pyridinone can be produced correspondingly.

PROCESS (e)

The 4(1H)-pyridinone derivatives of formula (I) where A is the sulfur atom can be produced by dissolving or suspending the corresponding 4(1H)-pyridinone derivative of formula (I) where A is the oxygen atom, in a suitable solvent, for example, pyridinone, xylene or toluene, and then reacting it with phosphorus pentasulfide, silicon disulfide, boron sulfide or the like under the refluxing temperature conditions.

According to a further aspect of this invention, therefore, there is provided a process for the production of a compound of the general formula (I) as described hereinbefore, which process comprises the step of:

either (i) reacting a 1,5-diphenylpentanetrione derivative represented by the general formula (II):

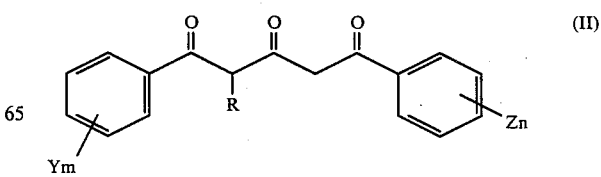

(II)

wherein Y, Z, R, m and n have the same meaning as defined above, or a tautomer thereof, with an aniline derivative represented by the general formula (III):

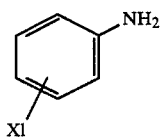 (III)

wherein X and l have the same meanings as defined above, in an inert organic solvent, or (ii) cyclizing a 5-anilino-1,5-diphenyl-4-pentene-1,3-dione derivative represented by the general formula (IV) or (V):

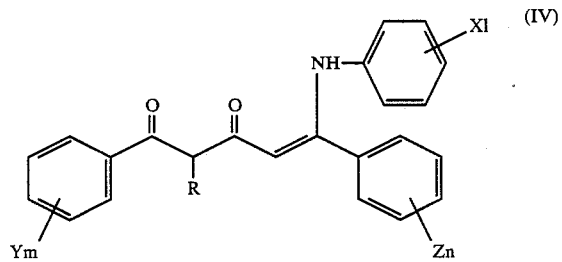 (IV)

wherein X, Y, Z, R, l, m and n have the same meanings as defined above, or

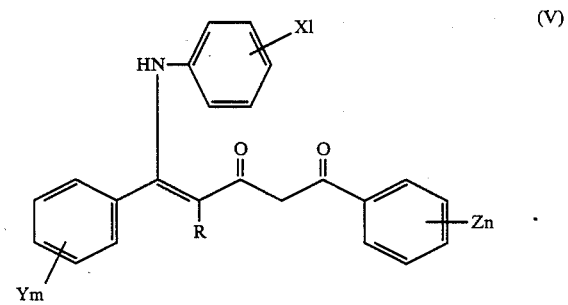 (V)

wherein X, Y, Z, R, l, m and n have the same meanings as defined above, or a tautomer thereof in or without an inert organic solvent in the presence of an acid catalyst, or (iii) reacting a phenylpropionic ester derivative represented by the general formula (VI):

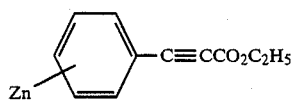 (VI)

wherein X and n have the same meanings as defined above, with an N-phenyl-1-phenylethaneimine derivative represented by the general formula (VII):

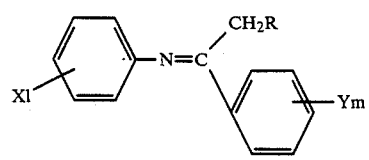 (VII)

wherein X, Y, R, l and m have the same meaning as defined above, in or without an inert organic solvent, in the presence of a Lewis acid such as aluminum chloride or titanium tetrachloride, or (iv) reacting a 4(1H)-pyridinone derivative represented by the general formula

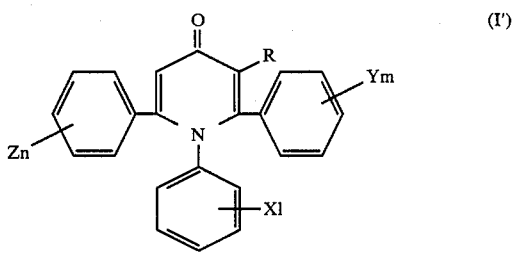 (I')

wherein X, Y, Z, R, m, n and l are defined above, with phosphorus pentasulfide, silicon disulfide, boron sulfide or other equivalent sulfurizing agent in an inert organic solvent under the refluxing temperature to convert the oxygen atom at the 4-position of the compound of the formula (I') into a sulfur atom which is a value of the group A in the compound of the formula (I).

Incidentally, when at least one phenyl group among the three phenyl groups at the 1-, 2-, and 6-positions of the compounds of this invention as produced in the above-described processes is containing at least one substituent at each of the ortho- or meta-positions thereof, the atrop-isomers exist. The atrop-isomers can be isolated from each other by chromatography on a silica gel column except for enantiomers.

Production of the compounds of this invention will now be illustrated with reference to the following Examples 1-33. Examples 1-10 and 30-32 are illustrative of the Process (a), Examples 11 illustrative of the Process (b), Examples 12-21 and 33 illustrative of the Process (c), Examples 22-26 and 28-29 illustrative of the Process (d), and Example 27 is illustrative of the Process (e).

EXAMPLE 1

Synthesis of 1-(3,5-dimethoxyphenyl)-3-methyl-2,6-diphenyl-4(1H)-pyridinone to 170 ml of chlorobenzene were added 4.2 g (0.015 mole) of 2-methyl-1,5-diphenyl-1,3,5-pentanetrione, 11.5 g (0.075 mole) of 3,5-dimethoxyaniline, 5.2 g (0.027 mole) of para-toluenesulfonic acid and 35.0 g of Molecular Sieves 5A, followed by refluxing the resulting mixture for 2 hours. After cooling the reaction mixture, solid matter was removed from the reaction mixture, followed by addition of 200 ml of chloroform thereto. The organic layer was washed first with 200 ml of 10% hydrochloric acid and then with 200 ml of a 10% aqueous solution of sodium hydroxide. The organic layer was washed further with water and was then dried over anhydrous sodium sulfate. Subsequent to removal of the sodium sulfate by filtration, the solvent was distilled off and the residue was subjected to chromatography on a silica gel column (eluent: ethyl acetate). Upon recrystallization of the resultant crystals from a 2:1 mixed solvent of acetone and hexane, 2.0 g of 1-(3,5-dimethoxyphenyl)-3-methyl-2,6-diphenyl-4(1H)-pyridinone having a melting point of 232°-236° C. was obtained.

EXAMPLE 2

Synthesis of 1-(2,6-diflourophenyl)-b 3-methyl-2,6-diphenyl-4(1H)-pyridinone

To 150 ml of xylene were added 2.8 g (0.010 mole) of 2-methyl-1,5-diphenyl-1,3,5-pentanetrione, 12.9 g (0.010 mole) of 2,6-diflouroaniline, 3.0 g (0.016 mole) of para-toluenesulfonic acid and 30.0 g of Molecular Sieves 5A, followed by refluxing the resulting mixture for 3 hours. After cooling the reaction mixture, solid matter was filtered off and the filtrate was washed successively with 50 ml of 10% hydrochloric acid, 50 ml of 10% aqueous solution of sodium hydroxide and water. The filtrate was then dried over anhydrous sodium sulfate. Subsequent to removal of the sodium sulfate by filtration, the solvent was distilled off and the residue was crystallized from a 2:1 mixed solvent of acetone and hexane to give 0.7 g of 1-(2,6-diflourophenyl)-3-methyl-2,6-diphenyl-4(1H)-pyridinone having a melting point of 219°–221° C.

EXAMPLE 3

Synthesis of 1-(2-chloro-5-nitrophenyl)-3-methyl-2,6-diphenyl-4(1H)-pyridinone

To 170ml of chlorobenzene were added 3.4 g (0.012 mole) of 2-methyl-1,5-diphenyl-1,3,5-pentanetrione, 10.4 g (0.060 mole) of 2-chloro-5-nitroaniline, 4.1 g (0.022 mole) of para-toluenesulfonic acid and 35.0 g of Molecular Sieves 5A, followed by refluxing for 2 hours. After cooling the reaction mixture, solid matter was removed from the reaction mixture, followed by addition of 200 ml of chloroform. The resultant mixture was washed first with 100 ml of 10% hydrochloric acid and then with 100 ml of a 10% aqueous solution of sodium hydroxide. The mixture was washed further with water and was then dried over anhydrous sodium sulfate. Subsequent to removal of the sodium sulfate, the solvent was distilled off and the residue was purified by chromatography on a silica gel column (eluent: ethyl acetate). Upon recrystallization of the resultant crystals from a 2:1 mixed solvent of acetone and hexane, 1.9 g of 1-(2-chloro-5-nitrophenyl)-3-methyl-2,6-diphenyl-4(1H)-pyridinone having a melting point of 277°–279° C. was obtained.

EXAMPLE 4

Synthesis of 1-2(2,4-dichloro-3-methylphenyl-3-methyl-2,6-diphenyl-4(1H)-pyridinone In 170 ml of chlorobenzene were dissolved 3.4 g (0.012 mole) of 2-methyl-1,5-diphenyl-1,3,5-pentanetrione and 10.6 g (0.06 mole) of 2,4-dichloro-3-methylaniline, followed by further addition of 4.1 g (0.022 mole) of para-toluenesulfonic acid and 35.0 g of Molecular Sieves 5A to the solution. After heating the reaction mixture under reflux for 2 hours, solid matter was removed from the reaction mixture, followed by an addition of 200 ml of chloroform. The resultant mixture was washed first with 100 ml of 10% hydrochloric acid and then with 100 ml of a 10% aqueous solution of sodium hydroxide. The mixture was washed further with water and was then dried over anhydrous sodium sulfate. Subsequent to removal of the sodium sulfate, the solvent was distilled off and the residue was purified by chromatography on a silica gel column (eluent: ethyl acetate). Upon recrystallization of the resultant crystals from a 2:1 mixed solvent of acetone and hexane, 0.7 g of 1-(2,4-dichloro-3-methylphenyl)-3-methyl-2,6-diphenyl-4(1H)-pyridinone having a melting point of 237°–238° C. was obtained.

EXAMPLE 5

Synthesis of 2-(3-ethoxyphenyl)-3-methyl-1,6-diphenyl-4(1H)-pyridinone

In 500 ml of xylene were dissolved 15.0 g (0.046 mole) of 1-(3-ethoxyphenyl)-2-methyl-5-phenyl-1,3,5-pentanetrione, 43.0 g (0.47 mole) of aniline and 8.8 g (0.092 mole) of methanesulfonic acid. The reaction mixture was heated under reflux for 30 minutes in a reactor fitted with a Dean-Stark apparatus. After cooling, the reaction mixture was filtered to remove solid matter, followed by removal of the solvent by distillation. The residue was extracted with chloroform and the resultant solution in chloroform (the extract) was washed first with 100 ml of 10% hydrochloric acid and then with 100 ml of a 10% aqueous solution of sodium hydroxide. The chloroform solution was washed further with water and was then dried over anhydrous sodium sulfate. Subsequent to removal of the sodium sulfate, the solvent was distilled off and the residue was subjected to chromatography on a silica gel column (eluent: ethyl acetate). Upon recrystallization of the resultant crystals from acetone, 5.3 g of 2-(3-ethoxyphenyl)-3-methyl-1,6-diphenyl-4-(1H)-pyridinone having a melting point of 146°–149° C. was obtained.

EXAMPLE 6

Synthesis of 6-(4-cyanophenyl)-3-methyl-1,2-diphenyl-4(1H)-pyridinone

In 400 ml of xylene were dissolved 10.0 g (0.033 mole) of 5-(4-cyanophenyl)-2-methyl-1-phenyl-1,3,5-pentanetrione, 25.0 g (0.26 mole) of aniline and 7.0 g (0.073 mole) of methanesulfonic acid. The solution obtained was heated under reflux for 30 minutes in a reactor fitted with a Dean-Stark apparatus. After cooling, 6.5 g (0.043 mole) of trifluoromethanesulfonic acid was added further to the reaction mixture and the resultant mixture was similarly heated under reflux for 30 minutes. After cooling, solid matter was removed from the reaction mixture, followed by concentration under pressure. The concentrate was extracted with dichloromethane. The organic layer was washed successively with 100 ml of 10% hydrochloric acid, 100 ml of a 10% aqueous solution of sodium hydroxide and water. The organic layer was then dried over anhydrous sodium sulfate. Subsequent to removal of the sodium sulfate, the solvent was distilled off and the residue was subjected to chromatography on a silica gel column (eluent: ethyl acetate). The resultant crystals were washed with acetone to afford 2.4 g of 6-(4-cyanophenyl)-3-methyl-1,2-diphenyl-4(1H)-pyridinone having a melting point of 229°–233° C.

EXAMPLE 7

Synthesis of 2-(2-chlorophenyl)-3-methyl-1-(2-methylphenyl)-phenyl-4(1H)-pyridinone In 500 ml of xylene were dissolved 37.7 g (0.012 mole) of 1-(2-chlorophenyl)-2-methyl-5-phenyl-1,3,5-pentanetrione, 38.6 g (0.36 mole) of 2-methylaniline, 22.8 g (0.12 mole) of para-toluenesulfonic acid and 30 g of Molecular Sieves 5A, followed by refluxing the resulting mixture for 8 hours. After cooling, solid matter was filtered off and the organic layer was washed first with 100 ml of 10% hydrochloric acid and then with 100 ml of a 10% aqueous solution of sodium hydroxide. After washing the organic layer further with water, it was dried over anhydrous sodium sulfate. Subsequent to removal of the sodium sulfate, the solvent was distilled off and the residue was subjected to chromatography on a silica gel column (eluent: ethyl acetate). As result, two atrop-isomers of 2-(2-chlorophenyl)-3-methyl-1-(2-methylphenyl)-6-phenyl-4(1H)-pyridinone, namely, Compound 338 and Compound 339 were obtained in yields of 1.2 g and 0.8 g, respectively. Their melting points were 227°–229° C. and 222°–225° C., respectively.

EXAMPLE 8

Synthesis of 1,2,6-tris(2-chlorophenyl)-3-methyl-4(1H)-pyridinone

To 200 ml of xylene were added 6.9 g (0.020 mole) of 1,5-bis(2-chlorophenyl)-2-methyl-1,3,5-pentanetrione, 25.5 g (0.20 mole) of 2-chloroaniline and 20.0 g of Molecular Sieves 5A. After heating the reaction mixture under reflux for 2 hours, the reaction mixture was poured into ice water, followed by addition of 200 ml of chloroform thereto and vigorous stirring of the resultant mixture. One hour later, the reaction mixture was filtered to remove solid matter. The organic layer was washed first with 50 ml of 10% hydrochloric acid and then with 50 ml of a 10% aqueous solution of sodium hydroxide. The mixture was washed further with water and was then dried over anhydrous sodium sulfate. Subsequent to removal of the sodium sulfate, the solvent was distilled off. The residue was purified by chromatography on a silica gel column (eluent: ethyl acetate) and then recrystallization from acetone to give 1.4 g of 1,2,6-tris(2-chlorophenyl)-3-methyl-4(1H)-pyridinone having a melting point of 205°–207° C.

EXAMPLE 9

Synthesis of 6-(2-chlorophenyl)-1-(2,6-difluorophenyl)-3-methyl-2-phenyl-4(1H)-pyridinone In 200 ml of xylene were dissolved 6.3 g (0.020 mole) of 5-(2-chlorophenyl)-2-methyl-1-phenyl-1,3,5-pentanetrione, 20.0 g (0.155 mole) of 2,6-difluoroaniline, 4,6 g (0.024 mole) of para-toluenesulfonic acid and 50.0 g of Molecular Sieves 5A, followed by reflux for 8 hours. Solid matter was filtered off from the reaction mixture and 300 ml of chloroform was added to the filtrate. The mixture obtained was washed first with 50 ml of 10% aqueous solution of sodium hydroxide. After washing the chloroform layer further with water, it was dried over anhydrous sodium sulfate. Subsequent to removal of the sodium sulfate, the solvent was distilled off and the residue was subjected to column chromatography (eluent: ethyl acetate) to afford crystals. The crystals were recrystallized from a 2:1 mixed solvent of acetone and hexane, thereby yielding 2.0 g of 6-(2-chlorophenyl)-1-(2,6-difluorophenyl)-3-methyl-2-phenyl-4(1H)-pyridinone having a melting point of 213°–215° C.

EXAMPLE 10

Synthesis of 3-methyl-1-(2,3,4,5,6-pentafluorophenyl)-2,6-diphenyl-4(1H)-pyridinone In 110 ml of xylene were dissolved 3.1 g (0.011 mole) of 2-methyl-1,5-diphenyl-1,3,5-pentanetrione, 20.0 g (0.11 mole) of 2,3,4,5,6-pentafluoroaniline, 3.1 g (0.016 mole) of paratoluenesulfonic acid and 22.0 g of Molecular Sieves 5A, followed by reflux for 1 hours. After cooling the reaction mixture, solid matter was removed by filtration and the filtrate was then concentrated. After 200 ml of chloroform was added, the resultant solution in chloroform was washed first with 50 ml of 10% hydrochloric acid and then with 50 ml of a 10% aqueous solution of sodium hydroxide. After washing the solution in chloroform further with water, it was dried over anhydrous sodium sulfate. Subsequent to removal of the sodium sulfate, the solvent was distilled off and the residue was subjected to column chromatography (eluent: 50.1 mixed solvent of chloroform and methanol). The resulting crystals were recrystallized from a 1:1 mixed solvent of acetone and hexane, thereby affording 1.3 g of 3-methyl-1-(2,3,4,5,6-pentafluorophenyl)-2,6-diphenyl-4(1H)-pyridinone having a melting point of 192°–194° C.

EXAMPLE 11

Synthesis of 1-(2-chlorophenyl)-3-methyl-2,6-diphenyl-4(1H)-pyridinone

To 17.8 g (0.050 mole) of 5-(2-chloroanilino)-2-methyl-1,5-diphenyl-4-pentene-1,3-dione, 200 ml of xylene and 100 g of polyphosphoric acid were added. The resultant mixture was heated under reflux for 30 minutes. After cooling the reaction mixture, the solvent was removed by decantation and the remaining solid matter was added with 200 ml of chloroform and 200 ml of water. The resultant mixture was then stirred vigorously for 2 hours. Thereafter, the organic layer was washed with water and then dried over anhydrous sodium sulfate. After removal of the sodium sulfate, the solvent was distilled off and the residue was recrystallized from acetone, thereby affording 2.8 g of 1-(2-chlorophenyl)-3-methyl-2,6-diphenyl-4(1H)-pyridinone having a melting point of 228°–231° C.

EXAMPLE 12

Synthesis of 1-(4-fluorophenyl)-3-methyl-2,6-diphenyl-4(1H)-pyridinone

To 300 ml of toluene were added 9.1 g (0.040 mole) of N-(4fluorophenyl)-1-phenylpropaneimine, 4.7 g (0.035 mole) of aluminum chloride and 5.2 g (0.030 mole) of ethyl phenylpropiolate, followed by refluxing the resultant mixture for 5 hours. Thereafter, the reaction mixture was poured into 500 ml of 2N sulfuric acid which had been ice-cooled, followed by extraction with chloroform. After washing the organic layer with water, the organic layer wad dried over anhydrous sodium sulfate. Subsequent to removal of the sodium sulfate, the solvent was distilled off and the residue was purified by chromatography on a silica gel column (eluent: 1:50 mixed solvent of methanol and chloroform). The resultant crystals were recrystallized from 1:1 mixed solvent of acetone and hexane to give 1.0 g of 1-(4-fluorophenyl)-3-methyl-2,6-diphenyl-4(1H)-pyridinone having a melting point of 256°-259° C.

EXAMPLE 13

Synthesis of 1-(3-methoxyphenyl)-3-methyl-2,6-diphenyl-4(1H)-pyridinone

Added to 300 ml of benzene were 8.0 g (0.033 mole) of N-(3-methoxyphenyl)-1-phenylpropaneimine and 4.7 g (0.035 mole) of aluminum chloride, followed by dropwise addition of 5.2 g (0.030 mole) of ethyl phenylpropiolate at room temperature.

After heating the reaction mixture under reflux for 30 hours under a nitrogen atmosphere, the reaction mixture was poured into 500 ml of 2N sulfuric acid which had been ice-cooled, followed by extraction with chloroform. After washing the organic layer with water, it was dried over anhydrous sodium sulfate. Subsequent to removal of the sodium sulfate, the solvent was distilled off and the residue was purified by chromatography on a silica gel column (eluent: ethyl acetate). The crystals obtained were recrystallized from a 2:1 mixed solvent of ethyl acetate and hexane to obtain 0.8 g of 1-(3-methoxyphenyl)-3-methyl-2,6-diphenyl-4(1H)-pyridinone having a melting point of 183°-185° C.

EXAMPLE 14

Synthesis of 2-(3,4-dichlorophenyl)-3-methyl-1,6-diphenyl-4(1H)-pyridinone

To 500 ml of toluene were added 6.2 g (0.022 mole) of 1-(3,4-dichlorophenyl)-N-phenylpropaneimine and 3.9 g (0.022 mole) of ethyl phenylpropiolate, followed by addition of 3.6 g (0.023 mole) of aluminum chloride. After heating the reaction mixture with stirring at 60°-70° C. for 4 days under a nitrogen atmosphere, the reaction mixture was poured into 400 ml of 2N sulfuric acid which had been ice-cooled, followed by extraction with dichloromethane. After washing the organic layer with water, it was dried over anhydrous sodium sulfate. Subsequent to removal of the sodium sulfate, the solvent was distilled off and the residue was purified by chromatography on a silica gel column (eluent: ethyl acetate). The resulting crystals were recrystallized from a 2:1 mixed solvent of acetone and hexane to afford 1.9 g of 2-(3,4-dichlorophenyl)-3-methyl-1,6-diphenyl-4(1H)-pyridinone having a melting point of 188°-191° C.

EXAMPLE 15

Synthesis of 6-(2-methylphenyl)-3-methyl-1,2-diphenyl-4(1H)-pyridinone

To 300 ml of toluene were added 7.5 g (0.036 mole) of N-phenyl-1-phenylpropaneimine, 5.8 g (0.031 mole) of ethyl 2-methylphenylpropiolate and 6.0 g (0.045 mole) of aluminum chloride. The reaction mixture was stirred with heating at 60° C. for 3 days in a nitrogen atmosphere. After cooling, the reaction mixture was poured into 500 ml of 2N sulfuric acid, followed by extraction with chloroform. After washing the organic layer with water, it was dried over anhydrous sodium sulfate. Subsequent to removal of the sodium sulfate, the solvent was distilled off and the residue was purified by chromatography on a silica gel column (eluent: ethyl acetate). The resultant crystals were washed with a 2:1 mixed solvent of acetone and hexane to obtain 0.4 g of 6-(2-methyl-phenyl)-3-methyl-1,2-diphenyl-4(1H)-pyridinone having a melting point of 188°-191° C.

EXAMPLE 16

Synthesis of 1,2-bis(2-chlorophenyl)-3-methyl-6-phenyl-4(1H)-pyridinone

To 300 ml of toluene were added 6.2 g (0.022 mole) of N,1-bis(2-chlorophenyl)propaneimine, 3.9 g (0.022 mole) of ethyl phenylpropiolate and 3.6 g (0.027 mole) of aluminum chloride. After heating the reaction mixture with stirring at 60° C. for 4 days, the reaction mixture was poured into 500 ml of 2N sulfuric acid, followed by extraction with dichloromethane. After washing the organic layer with water, it was dried over anhydrous sodium sulfate. Subsequent to removal of the sodium sulfate, the solvent was distilled off and the residue was subjected to column chromatography (eluent: ethyl acetate) to obtain two types of atrop-isomers of 1,2-bis(2-chlorophenyl)-3-methyl-6-phenyl-4(1H)-pyridinone, namely, 0.6 g of Compound 335 and 0.2 g of Compound 336, of which the melting points were 205°-207° C. and 232°-234° C., respectively.

EXAMPLE 17

Synthesis of 1-(2-chlorophenyl)-2-(4-methyoxyphenyl)-3-methyl-6-phenyl-4(1H)-pyridinone To 300 ml of toluene were added 6.3 g (0.023 mole) of N-(2-chlorophenyl)1-(4-methoxyphenyl)propaneimine, 4.0 g (0.023 mole) of ethyl phenylpropiolate and 3.7 g of aluminum chloride. The reaction mixture was heated with stirring at 60° C. for 4 days. After cooling, the reaction mixture was poured into 500 ml of 2N sulfuric acid, followed by extraction with dichloromethane. After washing the organic layer with water, it was dried over anhydrous sodium sulfate. Subsequent to removal of the sodium sulfate, the solvent was distilled off and the residue was subjected to chromatography on a silica gel column (eluent: ethyl acetate). The crystals thus-obtained were recrystallized from a 2:1 mixed solvent of acetone and hexane to give 1.0 g of 1-(2-chlorophenyl)-2-(4-methoxyphenyl)-3-methyl-6-phenyl-4(1H)-pyridinone.

EXAMPLE 18

Synthesis of 1-(2-chlorophenyl)-3-ethyl-2,6-diphenyl-4(1H)-pyridinone

To 300 of toluene were added 10.3 g (0.040 mole) of N-(2-chlorophenyl)-1-phenylbutaneimine, 5.2 g (0.030 mole) of ethyl phenylpropiolate and 5.3 g (0.040 mole) of aluminum chloride. After heating the reaction mixture under reflux for 20 hours under a nitrogen atmosphere, the reaction mixture was poured into 500 ml of 2N sulfuric acid which had been ice-cooled, followed by extraction with chloroform. After washing the organic layer with 50 ml of a 10% aqueous solution of sodium hydroxide and then with water, it was dried over anhydrous sodium sulfate. Subsequent to removal of the sodium sulfate, the solvent was distilled off and the residue was purified by chromatography on a silica gel column (eluent: ethyl acetate) so that 2.0 g of 1-(2-chlorophenyl)-3-ethyl-2,6-diphenyl-4(1H)-pyridinone having a melting point of 165°-166° C. was obtained.

EXAMPLE 19

Synthesis of 3-chloro-1-(2-chlorophenyl)-2,6-diphenyl-4(1H)-pyridinone

To 300 ml of toluene were added 7.4 g (0.030 mole) of 2-chloro-N-(2-chlorophenyl)-1-phenylethaneimine, 5.2 g (0.030 mole) of ethyl phenylpropiolate and 6.7 g (0.050 mole) of aluminum chloride. The reaction mixture was then heated under reflux for 20 hours under nitrogen atmosphere. After cooling, the reaction mixture was poured into 500 ml of 2N sulfuric acid, followed by extraction with chloroform. After washing the organic layer with 50 ml of a 10% aqueous solution of sodium hydroxide and then with water, it was dried with anhydrous sodium sulfate. Subsequent to removal of the sodium sulfate, the solvent was distilled off and the residue was purified by chromatography on a silica gel column (eluent: ethyl acetate) to yield 3-chloro-1-(2-chlorophenyl)-2,6-diphenyl-4(1H)-pyridinone having a melting point of 230°–233° C.

EXAMPLE 20

Synthesis of 2-(2-bromophenyl)-3-methyl-1,6-diphenyl-4(1H)-pyridinone hydrochloride to 300 ml of toluene were added 6.4 g (0.022 mole) of 1-(2-bromophenyl)-N-phenylpropaneimine, 3.9 g (0.022 mole) of ethyl phenylpropiolate and 3.6 g (0.027 mole) of aluminum chloride. The reaction mixture was then heated at 60° C. hours. After cooling, the reaction mixture was poured into 500 ml of 2N sulfuric acid, followed by extraction with methylene chloride. After washing the organic layer (the extract) with water, the organic layer was dried over anhydrous sodium sulfate. The solvent was distilled off and the residue was subjected to chromatography on a silica gel column (eluent: ethyl acetate). The resultant crystals were then recrystallized from a 2:1 mixed solvent of acetone and hexane to obtain 1.3 g of 2-(2-bromophenyl)-3-methyl-1,6-diphenyl-4(1H)-pyridinone hemihydrochloride having a melting point of 236°–238° C.

Elemental analysis: Calculated for $C_{24}H_{18}BrNO \cdot \frac{1}{2}HCl$: C, 66.34; H, 4.29; N, 3.19%. Found: C, 66.64; H, 4.52; N, 3.22%.

EXAMPLE 21

Synthesis of 1-(2-chlorophenyl)-3-methyl-2,6-diphenyl-4(1H)-pyridinone hydrochloride Added to 700 ml of toluene were 73.1 g (0.30 mole) of N-(2-chlorophenyl)-1-phenylpropaneimine, 34.8 g (0.20 mole) of ethyl phenylpropiolate and 40.0 g (0.30 mole) of aluminum chloride. The reaction mixture was then heated with stirring as 60° C. for 3 days. After cooling, the reaction mixture was poured into 1000 ml of 2N sulfuric acid, followed by extraction with chloroform. After washing the organic layer with water, the organic layer was dried over anhydrous magnesium sulfate. The solvent was distilled off and the residue was purified by chromatography on a silica gel column (eluent: ethyl acetate). The crystals obtained were then recrystallized from a 1:2 mixed solvent of chloroform and hexane to give 17.0 g of 1-(2-chlorophenyl)-3-methyl-2,6-diphenyl-4(1H)-pyridinone. 1/5HCl having a melting point of 229°–231° C.

Elemental analysis: Calculated for $C_{24}H_{18}ClNO \cdot 1/5HCl$: C, 76.03; H, 4.83; N, 3.69%. Found: C, 75.56; H, 4.91; n, 3.72%.

EXAMPLE 22

Synthesis of 2-(4-hydroxyphenyl)-3-methyl-1,6-diphenyl-4(1H)-pyridinone

To 300 ml of a solution of 18.7 g (0.051 mole) of 2-(4-methoxyphenyl)-3-methyl-1,6-diphenyl-4(1H)-pyridinone in methylene chloride, 25.0 g (0.010 mole) of boron tribromide was added dropwise. After stirring the resultant mixture at room temperature for 15 hours, the reaction mixture was poured into water, followed by neutralization with sodium hydrogen carbonate. Deposited crystals were collected by filtration and washed with aceton, thereby affording 16.9 g of 2-(4-hydroxyphenyl)-3-methyl-1,6-diphenyl-4(1H)-pyridinone having a melting point of not lower than 300° C.

EXAMPLE 23

Synthesis of 3-methyl-1,6-diphenyl-2-(4-propoxyphenyl)-4(1H)-pyridinone

To 50 ml of a suspension of 0.36 g (0.018 mole) of sodium hydride in DMSO, 1.7 g (0.0048 mole) of 2-(4-hydroxyphenyl)-3-methyl-1,6-diphenyl-4(1H)-pyridinone was added, followed by further dropwise addition of 1.0 g (0.0058 mole) of propyl iodide. The reaction mixture was then stirred at room temperature for 6 hours. The reaction mixture was thereafter poured into ice water, followed by extraction with chloroform. After washing the organic layer with water, it was dried over anhydrous magnesium sulfate. The solvent was distilled off, followed by recrystallization from a 2:1 mixed solvent of acetone and hexane to obtain 1.6 g of 3-methyl-1,6-diphenyl-2-(4-propoxyphenyl)-4(1H)-pyridinone having a melting point of 165°–168° C.

EXAMPLE 24

Synthesis of 1-(2-aminophenyl)-3-methyl-2,6-diphenyl-4(1H)-pyridinone

To 50 ml of a suspension of 1.8 g (0.0050 mole) of 3-methyl-1-(2-nitrophenyl)-2,6-diphenyl-4(1H)-pyridinone and 0.2 g of 10% Pd-C in methanol, 1.5 g (0.023 mole) of ammonium formate (as a reducing agent) was added. After heating the resultant mixture under reflux for 3 hours under a nitrogen gas stream, solid matter was filtered off from the reaction mixture and the solvent was distilled off. The residue was then extracted with chloroform and the organic layer (the extract) was washed with 50 ml of a 10% aqueous solution of sodium hydroxide. After washing the organic layer with water, it was dried with anhydrous sodium sulfate and the solvent was then distilled off. The crystals thus-obtained were washed with acetone to give 0.9 g of 1-(2-aminophenyl)-3-methyl-2,6-diphenyl-4(1H)-pyridinone having a melting point of not lower than 300° C.

EXAMPLE 25

Synthesis of 1-(4-methanesulfinylphenyl)-3-methyl-2,6-diphenyl-4(1H)-pyridinone

Dissolved in 30 ml of methylene chloride was 1.1 g (0.0029 mole) of 3-methyl-1-(4-methylthiophenyl)-2,6- diphenyl-4(1H)-pyridinone, followed by addition of 0.6 g (0.0034 mole) of m-chloroperbenzoic acid (as oxidizing agent). After stirring the reaction mixture for 15 minutes, it was poured into water, followed by extraction with methylene chloride. The organic layer (the extract) was washed with 20 ml of a saturated aqueous solution of sodium hydrogen carbonate and then with water. The organic layer was thereafter dried over anhydrous sodium sulfate. The solvent was distilled off and the resulting crystals were recrystallized form a 2:1 mixed solvent of acetone and hexane, affording 1.1 g of 1-(4-methanesulfinylphenyl)-3-methyl-2,6-diphenyl-4(1H)-pyridinone having a melting point of 242°–244° C.

EXAMPLE 26

Synthesis of 1-(3-methanesulfonylphenyl)-3-methyl-2,6-diphenyl-4(1H)-pyridinone

In 5 ml of water was dissolved 1.2 g (0.0019 mole) of Oxone. The resulting solution was then added dropwise to 5 ml of a methanol solution of 0.5 g (0.0013 mole) of 1-(3-methanesulfinylphenyl)-3-methyl-2,6-diphenyl-4(1H)-pyridinone. After stirring the reaction mixture for 2 hours, it was poured into water, followed by extraction with chloroform. The organic layer was washed with water and was thereafter dried over anhydrous sodium sulfate. The solvent was distilled off and the residue was crystallized form a 2:1 mixed solvent of acetone and hexane, affording 0.4 g of 1-(3-methanesulfonylphenyl)-3-methyl-2,6-diphenyl-4(1H)-pyridinone having a melting point of 246°–248° C.

EXAMPLE 27

Synthesis of 1-(2-chlorophenyl)-3-methyl-2,6-diphenyl-4(1H)-pyridinethione

To 40 ml of pyridine were added 1.3 g (0.0035 mole) of 1-(2-chlorophenyl)-3-methyl-2,6-diphenyl-4(1H)-pyridinone and 0.9 g (0.0042 mole) of phosphorus pentasulfide, followed by refluxing the resultant mixture for 3 hours. After cooling, the reaction mixture was poured into water and the resulting crystals were collected by filtration. The crystals were dissolved in 100 ml of chloroform, and washed first with 30 ml of 2N hydrochloric acid and then with 30 ml of a saturated aqueous solution of sodium hydrogencarbonate. After washing the chloroform solution further with water, it was dried over anhydrous sodium sulfate. After removal of sodium sulfate, the solvent was distilled off to obtain crystals. The crystals were recrystallized from a 1:1 mixture of acetone and hexane, thereby obtaining 1.1 g of 1-(2-chlorophenyl)-3-methyl-2,6-diphenyl-4(1H)-pyridinethione having a melting point of 271°–275° C.

EXAMPLE 28

Synthesis of 1,2,6-triphenyl-3-trifluoromethyl-4(1H)-pyridinone

To 40 ml of 1-methyl-2-pyrrolidinone were added 2.0 g (0.0050 mole) of 3-bromo-1,2,6-triphenyl-4(1H)-pyridinone, 2.7 g (0.020 mole) of sodium trifluoroacetate and 1.9 g (0.010 mole) of cuprous iodide. The reaction mixture was then heated at 160° C. for 5 hours in a nitrogen atmosphere. After allowing the reaction mixture to cool down, it was poured into water, followed by extraction with ethyl ether. The organic layer (the extract) was washed with 50 ml of a saturated aqueous solution of sodium hydrogen carbonate. After washing the organic layer further with water, it was dried over anhydrous sodium sulfate. Subsequent to removal of the sodium sulfate, the solvent was distilled off, and the residue was crystallized from a 1:3 mixed solvent of ethyl acetate and hexane to yield 0.4 g of 1,2,6-triphenyl-3-trifluoromethyl-4(1H)-pyridinone having a melting point of 222°–225° C.

EXAMPLE 29

Synthesis of 3-methyl-2,6-diphenyl-1-(3-propargyloxyphenyl)-4(1H)-pyridinone

To 50 ml of a suspension of 0.72 g (0.03 mole) of sodium hydride in DMSO, 3.5 g (0.01 mole) of 1-(3-hydroxyphenyl)-3-methyl-2,6-diphenyl-4(1H)-pyridinone was added, followed by further dropwise addition of 1.4 g (0.012 mole) of propargyl bromide. The reaction mixture was thereafter poured into ice water, followed by extraction with chloroform. After washing the organic layer (the extract) with water, it was dried over anhydrous magnesium sulfate. The solvent was distilled off, followed by recrystallization from a 2:1 mixed solvent of acetone and hexane to obtain 1.5 g of 3-methyl-2,6-diphenyl-1-(3-propargyloxyphenyl)-4-(1H)-pyridinone having a melting point of 166°–169° C.

EXAMPLE 30

Synthesis of 1-(3,5-dimethoxyphenyl)-2-(4-methoxyphenyl)-3-methyl-6-phenyl-4(1H)-pyridinone p-toluenesulfonate To 200 ml of chlorobenzene were added 3.1 g (0.01 mole) of 1-(4-methoxyphenyl)-2-methyl-5-phenyl-1,3,5-pentanetrione, 2.3 g (1.5 mole) of 3,5-dimethoxyaniline, 2.9 g (0.015 mole) of para-toluenesulfonic acid and 10 g of Molecular Sieves 5A, followed by refluxing the resulting mixture for 2 hours. After cooling the reaction mixture, solid matter was removed from the reaction mixture, followed by addition of 500 ml of chloroform thereto. The organic layer was washed first with 200 ml of 10% hydrochloric acid and then with water. The organic layer was then dried over anhydrous sodium sulfate. Subsequent to removal of the sodium sulfate by filtration, the solvent was distilled off and the residue was subjected to chromatography on a silica gel column (eluent: ethyl acetate). Upon washing the resultant crystals with ethyl acetate, 3.3 g of 1-(3,5-dimethoxyphenyl)-2-(4-methoxyphenyl)-3-methyl-6-phenyl-4(1H)-pyridinone p-toluenesulfonate having a melting point of 202°–204° C. was obtained.

EXAMPLE 31

Synthesis of 1-(2-fluorophenyl)-3-methyl-6-(3-methylphenyl)-2-phenyl-4(1H)-pyridinone To 30 ml of xylene were added 2.0 g (0.0068 mole) of 2-methyl-5-(3-methylphenyl)-1-phenyl-1,3,5-pentanetrione, 7.6 g (0.068 mole) of 2-fluoroaniline, 2.0 g (0.012 mole) of para-toluenesulfonic acid and 14.0 g of Molecular Sieves 5A, followed by refluxing the resulting mixture for 1 hour. After cooling the reaction mixture, solid matter was filtered off and the filtrate was mixed with 100 ml of chloroform and then washed successively with 50 ml of 10% hydrochloric acid, 50 ml of a 10% aqueous solution of sodium hyroxide and water. The filtrate was then dried over anhydrous sodium sulfate.

Subsequent to removal of the sodium sulfate, the solvent was distilled off and the residue was crystallized from a 1:3 mixed solvent of chloroform and hexane to give 1.3 g of 1-(2-fluorophenyl)-3-methyl-6-(3-methylphenyl)-2-phenyl-4-(1H)-pyridinone having a melting point of 211°–214° C.

EXAMPLE 32

Synthesis of 2-(2-chlorophenyl)-6-(2-fluorophenyl)-3-methyl-1-phenyl-4(1H)-pyridinone In 450 ml of xylene were suspended 15.3 g of 1-(2-chlorophenyl)-2-methyl-5-(2-fluoro-phenyl)-1,3,5-pentanetrione, 6.4 g of aniline, 6.6 g of para-toluenesulfonic acid and 85 g of Molecular Sieves 5A, followed by refluxing the resultant mixture for 8 hours. Xylene was distilled off from the reaction mixture and 300 ml of chloroform was added to the residue. The mixture obtained was filtered and the filtrate was washed first with 10% hydrochloric acid and then with a 10% aqueous solution of sodium hydroxide. After washing the chloroform phase further with water, the solution in chloroform was dried over anhydrous sodium sulfate. Subsequent to removal of the sodium sulfate, the solvent was distilled off and the residue was purified by column chromatography (eluent: ethyl acetate-n-hexane, 1:3) to afford crude crystals. The crystals were recrystallized from ethyl acetate, yielding 4.5 g of 2-(2-chlorophenyl)-6(2fluorophenyl)-3-methyl-1-phenyl-4(1H)-pyridinone having a melting point of 182°–183° C.

EXAMPLE 33

Synthesis of 2-(2,4-difluorophenyl)-6-(2-fluorophenyl)-1-(3,5-dimethoxyphenyl)-3-methyl-4(1H)-pyridinone In 3 l of toluene were dissolved 54.9 g (0.18 mol) of N-(3,5-dimethoxyphenyl)-1-(2,4-difluorophenyl)-propanimine and 27.5 g (0.14 mole) of ethyl (2-fluorophenyl) propionate, and the resultant solution was placed under a nitrogen atmosphere and then admixed with 23.8 g (0.18 mol) of aluminum chloride, followed by refluxing the resultant mixture for 16 hours. After cooling, the reaction mixture was poured into 2N sulfuric acid, followed by extraction with chloroform. After washing the organic layer with 5% aqueous sodium hydroxide, and water, it was dried over anhydrous sodium sulfate. Subsequent to removal of the sodium sulfate, the solvent was distilled off and the residue was subjected to chromatography on a silica gel column (eluent: ethyl acetate-N-hexane, 1:1). The crystals thus-obtained were recrystallized from ethyl acetate to afford 7.3 g of 2-(2,4-difluorophenyl)-6-(2-fluorophenyl)-1-(3,5-dimethoxyphenyl)-3-methyl-4(1H)-pyridinone having a melting point of 171°–173° C.

The new compounds of the formula (I) according to this invention may be formulated into a fungicidal composition by mixing with a liquid or solid carrier or vehicle which is conventionally used in the art. According to another aspect of this invention, therefore, there is provided a fungicidal composition for agricultural and horticultural utilities, which comprises a compound of the general formula (I) as defined hereinbefore or a salt thereof as the active ingredient, n combination with a carrier for the active ingredient.

Although the new compound of this invention may be applied alone, it may usually be admixed with a carrier, optionally together with surfactant, dispersant or auxiliary agent and then formulated in a known manner, for example, into a dust, a wettable powder, an emulsifiable concentrate, fine particles or granules.

As suitable examples of the carriers, may be mentioned solid carriers such as talc, bentonite, clay, kaolin, diatomaceous earth, white carbon, vermiculite, slaked lime, siliceous sand, ammonium sulfate and urea; and liquid carriers such as isopropyl alcohol, xylene, and cyclohexanone. Illustrative examples of the surfactant and dispersant may include salts of alcohol-sulfuric acid esters, alkylarylsulfonic acid salts, diarylmethanedisulfonic acid salts, ligninsulfonic acid salts, polyoxyethyleneglycol ethers, polyoxyethylenealkyl aryl ethers, polyoxyethylenesorbitan monoalkylates, and so on. Suitable examples of the adjuvants include carboxymethylcellulose, polyethylene glycol, gum arabi, etc. These preparations can be applied after diluting same to a suitable concentration of the active ingredient, or they can be applied directly.

The proportion of the active ingredient in the composition may be increased or decreased as needed. When formulated into a dust or granules, 0.1–20 wt. % of the active ingredient is preferred. For an emulsifiable concentrate or wettable powder, 5–80 wt. % of the active ingredient is preferred.

The rate of application of the fungicidally active compound of this invention may vary depending on the type of the active compound employed, the kind of the disease to be controlled, the nature of occurrence of the disease, the degree of damage, environmental conditions, the preparation form to be used, etc. When the composition of this invention is applied directly in the form of dust or granules, it is recommendable that the rate of application of the active ingredient is suitably chosen in a range of 10 to 500 g per 10 ares. When the composition of this invention in the form of an emulsifiable concentrate or a wettable powder is diluted with water before its application and then the liquid preparation obtained is applied, it is preferred that the concentration of the active ingredient in the diluted liquid preparation is suitably chosen in a range of 10 to 1000 ppm. Generally, however, the compound of this invention can be applied in an amount of from about 0.1 g to about 100 kg per hectare, preferably 1 g to 10 kg per hectare. When it is sprayed to leaves and stem of plants, it is usuallly diluted to a concentration of about 0.1 to 10,000 ppm, preferably 10 to 3,000 ppm.

The fungicidal composition of this invention are now illustrated with reference to the following Examples 34–37, wherein all designations of "%" are given in percent by weight.

EXAMPLE 34

(Dust)

Two percent of Compound 1, 5% of diatomaceous earth and 93% of clay were uniformly mixed and ground into a dust.

EXAMPLE 35 cl (Wettable Powder)

Fifty percent of Compound 7, 45% of diatomaceous earth, 2% of sodium dinaphthylmethanedisulfonate and 3% of dosium ligninsulfonate were uniformly mixed and ground into a wettable powder.

EXAMPLE 36 cl (Emulsifiable Concentrate)

Thirty percent of Compound 126, 20% of cyclohexanone, 11% of polyoxyethylene alkylaryl ether, 4% of calcium alkylbenzenesulfonate and 35% of methylnaphthalene were evenly dissolved together to prepare an emulsifiable concentrate.

EXAMPLE 37

(Granules)

Five percent of Compound 264, 2% of the sodium salt of the ester of lauryl alcohol and sulfuric acid, 5% of sodium ligninsulfonate, 2% of carboxymethylcellulose and 86% of clay were mixed together and ground uniformly. The mixture was added and kneaded with 20% of water. The resulting mixture was formed into granules of 14-32 mesh by means of an extrusion granulator and was then dried into granules.

The fungicidal compounds of this invention have excellent properties. They show broad antibacterial and antifungal spectra against pathogenic microorganisms of various, agricultural and horticultural diseases of plants, such as rice sheath blight (*Rhizoctonia solani*), rice blast (*Pyricularia oryzae*), cucumber downy mildew (*Pseudoperonospora cubensis*), cucumber powdery mildew (*Sphaerotheca fuliginea*), cucumber gray mold (*Botrytis cinerea*) and Alternaria sooty spot of Chinese mustard (*Alternaria brassicicola*). In particular, the compounds of this invention exhibit outstanding activity to control rice sheath blight (*Rhizoctonia solani*). Their fungicidal activities can appear in both the preventive treatment and curative treatment of the plant diseases and moreover are long-lasting. In addition, the new compounds of this invention are of high safety, due to their low toxicity to crops, warm-blooded animals, and a variety of fish and shellfish.

Effects of the fungicidal compounds of this invention are now illustrated by the following Tests.

TEST 1

(Test on the preventative effects for rice sheath blight, *Rhizoctonia solani*)

Rice seeds (variety: Kinmaze) were sown at a rate of 15 grains each in unglazed pots having a diameter of 7 cm. The seeds were allowed to grow for 4-5 weeks in a greenhouse. A wettable powder containing a test compound and formulated in accordance with the procedure of Example 35 was diluted with water to a concentration of 500 ppm of the active ingredient, and the aqueous preparation obtained was then sprayed at a rate of 10 ml per pot to the rice seedling at their 5 leaf stage. After dried in the air, the seedlings were inoculated at the basal parts with fungi, *Rhizoctonia solani* which had been cultured for 7 days in a rice hulls-wheat bran culture medium, and the inoculated rice plants were then kept in a moist room (28° C.). Five days later, the heights of lesions formed on rice leaf sheaths were measured individually. Control value (%) was then evaluated in accordance with the following equation.

$$\text{Control value (\%)} = \left(1 - \frac{\text{Height of lesion in treated plot}}{\text{Height of lesion in untreated plot}}\right) \times 100$$

Comparative Chemicals 1 and 2, the known compounds as identified hereinafter, were also tested in the same manner as above, for the comparision purpose.

Test results obtained are shown in Table 3a, Table 3b, Table 3c and Table 3d below.

TABLE 3a

| Compound No. tested | Control value (%) | Compound No. tested | Control value (%) | Compound No. tested | Control value (%) |
|---|---|---|---|---|---|
| 1 | 100 | 29 | 94 | 64 | 98 |
| 2 | 100 | 31 | 80 | 65 | 99 |
| 3 | 100 | 32 | 100 | 66 | 99 |
| 4 | 86 | 33 | 100 | 68 | 80 |
| 5 | 100 | 34 | 100 | 69 | 90 |
| 6 | 100 | 35 | 100 | 70 | 95 |
| 7 | 100 | 36 | 100 | 71 | 80 |
| 8 | 100 | 37 | 100 | 72 | 85 |
| 9 | 100 | 38 | 99 | 73 | 100 |
| 10 | 100 | 40 | 98 | 76 | 100 |
| 11 | 100 | 42 | 78 | 77 | 100 |
| 12 | 100 | 43 | 92 | 78 | 100 |
| 13 | 100 | 44 | 100 | 79 | 100 |
| 14 | 100 | 52 | 100 | 81 | 100 |
| 15 | 100 | 53 | 90 | 82 | 100 |
| 16 | 92 | 55 | 100 | 83 | 98 |
| 17 | 99 | 56 | 100 | 84 | 100 |
| 18 | 83 | 57 | 99 | 85 | 99 |
| 19 | 100 | 58 | 100 | 86 | 82 |
| 20 | 100 | 59 | 87 | 87 | 93 |
| 22 | 98 | 60 | 95 | 88 | 100 |
| 26 | 96 | 61 | 95 | 89 | 86 |
| 27 | 96 | 63 | 99 | 90 | 100 |
| 91 | 100 | 120 | 89 | 153 | 99 |
| 92 | 97 | 121 | 92 | 155 | 100 |
| 93 | 100 | 123 | 93 | 156 | 80 |
| 95 | 100 | 124 | 84 | 159 | 100 |
| 96 | 100 | 128 | 99 | 160 | 97 |
| 97 | 100 | 129 | 100 | 161 | 100 |
| 101 | 99 | 130 | 100 | 162 | 98 |
| 102 | 100 | 131 | 97 | 164 | 100 |
| 104 | 100 | 132 | 100 | 165 | 100 |
| 105 | 96 | 133 | 99 | 166 | 100 |
| 106 | 98 | 134 | 100 | 167 | 100 |
| 107 | 97 | 135 | 100 | 168 | 96 |
| 108 | 95 | 136 | 97 | 169 | 97 |
| 109 | 100 | 137 | 100 | 170 | 100 |
| 110 | 99 | 138 | 97 | 171 | 98 |
| 111 | 97 | 139 | 97 | 172 | 96 |
| 112 | 96 | 140 | 100 | 173 | 99 |
| 113 | 94 | 142 | 99 | 174 | 97 |
| 114 | 99 | 143 | 100 | 176 | 100 |
| 116 | 99 | 145 | 100 | 178 | 100 |
| 117 | 98 | 146 | 97 | 179 | 100 |
| 118 | 98 | 149 | 96 | 180 | 100 |
| 119 | 99 | 152 | 100 | 181 | 100 |
| 182 | 100 | 213 | 100 | 255 | 100 |
| 183 | 100 | 214 | 100 | 256 | 99 |
| 184 | 98 | 217 | 96 | 257 | 100 |
| 185 | 100 | 219 | 98 | 258 | 99 |
| 186 | 100 | 220 | 99 | 259 | 100 |
| 187 | 100 | 224 | 100 | 260 | 100 |
| 188 | 100 | 226 | 100 | 261 | 95 |
| 189 | 100 | 227 | 100 | 262 | 92 |
| 192 | 100 | 229 | 100 | 266 | 100 |
| 193 | 100 | 230 | 100 | 267 | 100 |
| 194 | 96 | 235 | 98 | 268 | 100 |
| 195 | 100 | 237 | 97 | 269 | 99 |
| 196 | 100 | 238 | 100 | 270 | 99 |
| 197 | 100 | 239 | 100 | 272 | 96 |
| 198 | 97 | 241 | 93 | 273 | 91 |
| 201 | 73 | 242 | 100 | 274 | 94 |
| 202 | 96 | 244 | 100 | 275 | 88 |
| 203 | 99 | 245 | 100 | 276 | 87 |
| 206 | 72 | 246 | 99 | 277 | 87 |
| 208 | 88 | 247 | 100 | 278 | 94 |
| 209 | 96 | 249 | 92 | 279 | 78 |
| 210 | 100 | 250 | 100 | 281 | 100 |
| 211 | 92 | 252 | 100 | 282 | 99 |
| 283 | 97 | 317 | 99 | 346 | 99 |
| 284 | 98 | 318 | 99 | 347 | 99 |
| 285 | 100 | 321 | 97 | 348 | 92 |
| 286 | 88 | 322 | 95 | 349 | 97 |
| 288 | 100 | 324 | 94 | 350 | 100 |
| 289 | 82 | 325 | 100 | 351 | 100 |
| 291 | 99 | 327 | 100 | 352 | 98 |
| 292 | 97 | 328 | 98 | 353 | 100 |
| 293 | 97 | 329 | 95 | 354 | 99 |

TABLE 3a-continued

| | | | | | |
|---|---|---|---|---|---|
| 296 | 100 | 331 | 78 | 355 | 99 |
| 298 | 98 | 333 | 81 | 356 | 99 |
| 299 | 98 | 334 | 97 | 357 | 99 |
| 300 | 93 | 335 | 100 | 358 | 97 |
| 301 | 100 | 336 | 100 | 359 | 100 |
| 302 | 80 | 337 | 100 | 360 | 100 |
| 303 | 100 | 338 | 100 | 361 | 100 |
| 305 | 99 | 339 | 100 | 362 | 98 |
| 309 | 100 | 340 | 100 | 363 | 100 |
| 310 | 100 | 341 | 100 | 364 | 100 |
| 311 | 96 | 342 | 99 | 365 | 100 |
| 313 | 93 | 343 | 99 | 366 | 95 |
| 314 | 87 | 344 | 99 | 367 | 100 |
| 316 | 93 | 345 | 100 | 368 | 100 |
| 369 | 100 | 392 | 100 | 415 | 100 |
| 370 | 97 | 393 | 99 | 416 | 100 |
| 371 | 100 | 394 | 98 | 417 | 99 |
| 372 | 96 | 395 | 100 | 418 | 100 |
| 373 | 100 | 396 | 100 | 419 | 95 |
| 374 | 100 | 397 | 100 | 420 | 100 |
| 375 | 96 | 398 | 100 | 471 | 100 |
| 376 | 100 | 399 | 99 | 472 | 100 |
| 377 | 98 | 400 | 100 | 473 | 99 |
| 378 | 100 | 401 | 100 | 474 | 97 |
| 379 | 100 | 402 | 98 | 475 | 100 |
| 380 | 100 | 403 | 97 | 476 | 100 |
| 381 | 100 | 404 | 98 | 477 | 100 |
| 382 | 100 | 405 | 100 | 478 | 100 |
| 383 | 100 | 406 | 100 | 479 | 100 |
| 384 | 100 | 407 | 99 | 480 | 100 |
| 385 | 100 | 408 | 100 | 481 | 100 |
| 386 | 100 | 409 | 100 | 482 | 99 |
| 387 | 99 | 410 | 97 | 483 | 100 |
| 388 | 100 | 411 | 97 | 484 | 100 |
| 389 | 100 | 412 | 100 | 485 | 96 |
| 390 | 99 | 413 | 97 | 486 | 98 |
| 391 | 92 | 414 | 87 | 487 | 99 |

| Compound No. tested | Control value (%) | Compound No. tested | Control value (%) |
|---|---|---|---|
| 488 | 90 | 542 | 96 |
| 489 | 100 | 543 | 90 |
| 490 | 100 | Comparative Chemical 1 | 0 |
| 491 | 100 | | |
| 492 | 100 | Comparative Chemical 2 | 13 |
| 493 | 100 | | |
| 494 | 100 | | |
| 495 | 97 | | |
| 511 | 100 | | |
| 514 | 100 | | |
| 515 | 100 | | |
| 516 | 100 | | |
| 522 | 98 | | |
| 525 | 96 | | |
| 527 | 77 | | |
| 529 | 91 | | |
| 530 | 90 | | |
| 531 | 80 | | |
| 532 | 88 | | |
| 534 | 70 | | |
| 535 | 97 | | |
| 538 | 98 | | |
| 541 | 70 | | |

TABLE 3b

| Compound No. tested | Control value (%) | Compound No. tested | Control value (%) |
|---|---|---|---|
| 544 | 100 | 568 | 100 |
| 545 | 100 | 569 | 100 |
| 546 | 100 | | |
| | | 570 | 100 |
| 547 | 100 | | |
| | | 571 | 100 |
| 548 | 100 | | |
| 549 | 100 | 572 | 100 |
| 550 | 100 | 573 | 100 |

TABLE 3b-continued

| Compound No. tested | Control value (%) | Compound No. tested | Control value (%) |
|---|---|---|---|
| 551 | 100 | | |
| | | 574 | 100 |
| 552 | 100 | | |
| | | 575 | 100 |
| 553 | 100 | | |
| 554 | 100 | | |
| 555 | 100 | Comparative Chemical 1 | 0 |
| 556 | 100 | | |
| 557 | 100 | Comparative Chemical 2 | 13 |
| 558 | 100 | | |
| 559 | 100 | | |
| 560 | 100 | | |
| 561 | 100 | | |
| 562 | 100 | | |
| 563 | 100 | | |
| 565 | 100 | | |
| 566 | 100 | | |

TABLE 3c

| Compound No. tested | Control value (%) | Compound No. tested | Control value (%) | Compound No. tested | Control value (%) |
|---|---|---|---|---|---|
| 581 | 100 | 602 | 100 | 626 | 100 |
| 582 | 100 | 604 | 100 | 627 | 100 |
| 583 | 100 | 605 | 100 | 628 | 100 |
| 584 | 100 | 606 | 100 | 629 | 100 |
| 585 | 100 | 607 | 100 | 630 | 100 |
| 586 | 100 | 608 | 100 | 631 | 100 |
| 587 | 100 | 609 | 100 | 632 | 100 |
| 588 | 100 | 610 | 100 | 633 | 100 |
| 589 | 98.5 | 611 | 100 | 634 | 100 |
| 590 | 100 | 612 | 100 | 635 | 100 |
| 591 | 100 | 613 | 100 | 636 | 100 |
| 592 | 100 | 614 | 100 | 637 | 100 |
| 593 | 100 | 615 | 100 | 638 | 100 |
| 594 | 100 | 616 | 100 | 639 | 100 |
| 595 | 100 | 617 | 100 | 640 | 100 |
| 596 | 100 | 618 | 100 | 641 | 100 |
| 597 | 100 | 621 | 100 | 642 | 100 |
| 598 | 97.8 | 622 | 100 | 643 | 100 |
| 599 | 100 | 623 | 100 | 644 | 100 |
| 600 | 100 | 624 | 100 | 645 | 100 |
| 601 | 100 | 625 | 100 | 646 | 100 |
| | | | | 647 | 100 |

TABLE 3d

| Compound No. tested | Control value (%) | Compound No. tested | Control value (%) | Compound No. tested | Control value (%) |
|---|---|---|---|---|---|
| 648 | 100 | 672 | 81.0 | 695 | 100 |
| 649 | 91.1 | 673 | 100 | 696 | 100 |
| 650 | 100 | 674 | 99.3 | 697 | 100 |
| 651 | 100 | 675 | 100 | 698 | 100 |
| 652 | 100 | 676 | 98.5 | 699 | 89.0 |
| 653 | 97.6 | 677 | 100 | 700 | 100 |
| 654 | 100 | 678 | 100 | 701 | 100 |
| 655 | 100 | 679 | 100 | 702 | 100 |
| 656 | 88.3 | 680 | 100 | 707 | 100 |
| 658 | 100 | 681 | 100 | 708 | 100 |
| 659 | 100 | 682 | 98.5 | 712 | 100 |
| 660 | 79.3 | 683 | 100 | 713 | 94.3 |
| 662 | 91.2 | 684 | 100 | 714 | 100 |
| | | | | 715 | 97.7 |
| 663 | 100 | 685 | 100 | 716 | 100 |
| 664 | 100 | 686 | 100 | 717 | 100 |
| 665 | 100 | 687 | 100 | 718 | 100 |
| 666 | 100 | 688 | 100 | 719 | 100 |
| 667 | 97.8 | 689 | 100 | 720 | 100 |
| 668 | 100 | 690 | 100 | 721 | 87.4 |
| 669 | 100 | 691 | 100 | 723 | 82.7 |

TABLE 3d-continued

| | | | | | |
|---|---|---|---|---|---|
| 670 | 100 | 692 | 100 | 725 | 100 |
| 671 | 83.9 | 693 | 100 | 726 | 100 |

| Compound No. tested | Control value (%) | Compound No. tested | Control value (%) |
|---|---|---|---|
| 727 | 100 | 757 | 100 |
| 728 | 100 | 758 | 100 |
| 729 | 100 | Comparative Chemical 1 | 0 |
| 730 | 100 | | |
| 731 | 100 | Comparative Chemical 2 | 15 |
| 732 | 100 | | |
| 733 | 100 | | |
| 734 | 100 | | |
| 735 | 100 | | |
| 736 | 100 | | |
| 737 | 88.2 | | |
| 738 | 100 | | |
| 739 | 100 | | |
| 740 | 100 | | |
| 741 | 100 | | |
| 742 | 100 | | |
| 743 | 100 | | |
| 744 | 100 | | |
| 745 | 100 | | |
| 746 | 100 | | |
| 747 | 100 | | |
| 755 | 100 | | |
| 756 | 94.9 | | |

Note:
In Tables 3a–3d,
Comparative Chemical 1:

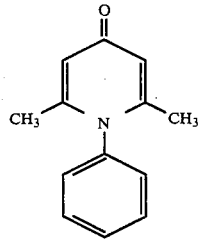

(Disclosed in Japanese Patent Application first publication "Kokai" No. 65871/81)
Comparative Chemical 2:

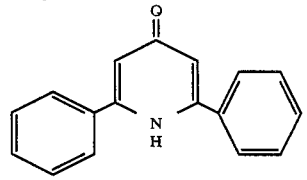

(Disclosed in Japanese Patent Application first publication "Kokai" No. 102504/80)

TEST 2

(Test on the preventive effects for rice blast, *Pyricularia oryzae*)

Unhulled rice seeds (variety: Aichi Asahi) were sown at a rate of 20 grains each in white porcelain pots having a diameter of 9 cm. The seeds were allowed to germinate and grow for 3-4 weeks in a greenhouse. A wettable powder containing a test compounds and formulated in accordance with the procedure of Example 35 was diluted with water to a concentration of 500 ppm of the active ingredient, and the aqueous preparation obtained was then sprayed at a rate of 10 ml per pot to the rice seedlings at their 4 leaf stage. After dried in the air, the seedlings were inoculated with a spore suspension of rice blast fungi, *Pyricularia oryzae* and then placed in a moist room at 25° C. On the fifth day after the inoculation, the number of lesions was counted to evaluate the control value.

$$\text{Control value (\%)} = \left(1 - \frac{\text{Number of lesions in treated plot}}{\text{Number of lesions in untreated plot}}\right) \times 100$$

Test results obtained are shown in Table 4a–4d. The same comparative chemicals as in Test 1 were also tested in the same manner as above, for the comparison purpose.

TABLE 4a

| Compound No. tested | Control value (%) | Compound No. tested | Control value (%) | Compound No. tested | Control value (%) |
|---|---|---|---|---|---|
| 1 | 100 | 82 | 93 | 125 | 83 |
| 2 | 94 | 83 | 91 | 129 | 100 |
| 6 | 80 | 84 | 83 | 130 | 93 |
| 8 | 93 | 89 | 85 | 133 | 84 |
| 9 | 78 | 93 | 100 | 135 | 100 |
| 13 | 86 | 95 | 92 | 136 | 82 |
| 16 | 100 | 97 | 93 | 137 | 94 |
| 38 | 90 | 102 | 100 | 145 | 100 |
| 52 | 85 | 104 | 85 | 150 | 89 |
| 60 | 92 | 106 | 79 | 151 | 93 |
| 61 | 89 | 107 | 91 | 153 | 85 |
| 65 | 100 | 108 | 83 | 160 | 94 |
| 66 | 74 | 109 | 93 | 164 | 93 |
| 67 | 83 | 110 | 100 | 165 | 81 |
| 68 | 100 | 111 | 90 | 168 | 84 |
| 71 | 84 | 112 | 90 | 170 | 100 |
| 74 | 90 | 113 | 92 | 173 | 100 |
| 76 | 93 | 114 | 88 | 174 | 100 |
| 77 | 100 | 117 | 89 | 176 | 100 |
| 78 | 100 | 123 | 90 | 177 | 100 |
| 79 | 100 | 124 | 89 | 179 | 100 |
| 182 | 82 | 260 | 100 | 348 | 92 |
| 183 | 82 | 261 | 94 | 349 | 100 |
| 186 | 100 | 266 | 73 | 351 | 100 |
| 187 | 84 | 272 | 100 | 353 | 90 |
| 188 | 80 | 277 | 73 | 354 | 82 |
| 194 | 100 | 279 | 81 | 355 | 100 |
| 198 | 92 | 288 | 100 | 356 | 100 |
| 211 | 100 | 295 | 81 | 357 | 100 |
| 213 | 91 | 305 | 90 | 358 | 93 |
| 219 | 83 | 310 | 80 | 359 | 100 |
| 226 | 100 | 318 | 90 | 360 | 100 |
| 227 | 100 | 328 | 90 | 361 | 100 |
| 229 | 91 | 335 | 80 | 362 | 100 |
| 235 | 94 | 337 | 100 | 364 | 91 |
| 244 | 100 | 338 | 88 | 365 | 100 |
| 245 | 100 | 339 | 85 | 367 | 93 |
| 246 | 100 | 340 | 100 | 370 | 100 |
| 247 | 100 | 341 | 84 | 371 | 89 |
| 252 | 82 | 342 | 100 | 373 | 84 |
| 254 | 81 | 344 | 100 | 374 | 100 |
| 255 | 100 | 345 | 100 | 376 | 92 |
| 257 | 89 | 346 | 100 | 377 | 88 |
| 259 | 89 | 347 | 85 | 379 | 94 |
| 380 | 100 | 417 | 100 | Comparative Chemical 1 | 0 |
| 381 | 100 | 418 | 100 | | |
| 382 | 100 | 419 | 92 | Comparative Chemical 2 | 0 |
| | | 471 | 89 | | |
| 383 | 100 | 472 | 100 | | |
| 385 | 94 | 473 | 84 | | |
| 386 | 93 | 474 | 82 | | |
| 387 | 87 | 475 | 92 | | |
| 388 | 100 | 476 | 90 | | |
| 390 | 100 | 479 | 81 | | |
| 392 | 100 | 481 | 90 | | |
| 393 | 100 | 489 | 88 | | |
| 394 | 100 | 490 | 98 | | |
| 395 | 100 | 491 | 94 | | |
| 396 | 100 | 493 | 100 | | |
| 397 | 100 | 494 | 100 | | |
| 398 | 100 | 495 | 100 | | |
| 400 | 100 | 511 | 97 | | |
| 401 | 86 | 514 | 92 | | |

TABLE 4a-continued

| Compound No. tested | Control value (%) | Compound No. tested | Control value (%) | Compound No. tested | Control value (%) |
|---|---|---|---|---|---|
| 408 | 100 | 525 | 100 | | |
| 409 | 100 | 526 | 81 | | |
| 415 | 90 | 542 | 91 | | |
| 416 | 100 | | | | |

TABLE 4b

| Compound No. tested | Control value (%) | Compound No. tested | Control value (%) |
|---|---|---|---|
| 544 | 100 | 565 | 97.5 |
| 545 | 100 | 566 | 99.5 |
| 546 | 100 | 569 | 86.9 |
| 547 | 98.9 | 572 | 94.5 |
| 548 | 100 | 573 | 100 |
| 549 | 100 | 574 | 100 |
| 550 | 96.6 | 575 | 98.5 |
| 551 | 97.1 | 576 | 100 |
| 552 | 97.1 | 577 | 98.5 |
| 553 | 98.3 | 578 | 100 |
| 554 | 97.1 | 579 | 100 |
| 555 | 100 | | |
| 556 | 100 | Comparative Chemical 1 | 0 |
| 557 | 100 | | |
| 558 | 99.4 | Comparative Chemical 2 | 0 |
| 559 | 100 | | |
| 560 | 95.7 | | |
| 561 | 100 | | |
| 562 | 97.5 | | |
| 563 | 97.5 | | |
| 564 | 98.5 | | |

TABLE 4c

| Compound No. tested | Control value (%) | Compound No. tested | Control value (%) | Compound No. tested | Control value (%) |
|---|---|---|---|---|---|
| 581 | 100 | 604 | 98.4 | 630 | 100 |
| 582 | 100 | 605 | 100 | 631 | 100 |
| 583 | 99.3 | 606 | 100 | 632 | 85.3 |
| 584 | 98.7 | 607 | 100 | 633 | 100 |
| 585 | 99.5 | 608 | 100 | 634 | 98.0 |
| 587 | 100 | 609 | 98.0 | 635 | 99.3 |
| 588 | 100 | 611 | 100 | 636 | 100 |
| 589 | 91.9 | 612 | 99.3 | 637 | 100 |
| 590 | 91.9 | 613 | 100 | 638 | 100 |
| 591 | 98.3 | 614 | 91.1 | 639 | 100 |
| 592 | 100 | 615 | 97.4 | 640 | 100 |
| 593 | 96.8 | 616 | 99.0 | 641 | 100 |
| | | 617 | 100 | | |
| 594 | 99.3 | 618 | 100 | 642 | 100 |
| 595 | 100 | 621 | 100 | 643 | 98.0 |
| 596 | 100 | 623 | 98.8 | 644 | 99.5 |
| 597 | 100 | 624 | 100 | 645 | 100 |
| 598 | 90.5 | 625 | 100 | 646 | 100 |
| 599 | 100 | 626 | 98.0 | 647 | 100 |
| 600 | 100 | 627 | 99.3 | | |
| 601 | 99.3 | 628 | 99.3 | | |
| 602 | 99.0 | 629 | 99.3 | | |

TABLE 4d

| Compound No. tested | Control value (%) | Compound No. tested | Control value (%) | Compound No. tested | Control value (%) |
|---|---|---|---|---|---|
| 648 | 88.1 | 677 | 100 | 702 | 100 |
| 650 | 100 | 678 | 99.4 | 712 | 95.8 |
| 651 | 97.1 | 679 | 98.3 | 713 | 100 |
| 652 | 91.3 | 680 | 92.5 | 714 | 90.9 |
| 653 | 95.7 | 681 | 87.6 | 716 | 75.8 |
| 654 | 96.3 | 682 | 75.8 | 717 | 100 |
| 655 | 95.7 | 683 | 90.0 | 718 | 97.4 |
| 657 | 71.6 | 684 | 75.3 | 725 | 92.4 |
| 658 | 91.1 | 685 | 91.8 | 726 | 81.8 |
| 659 | 98.6 | 686 | 95.9 | 727 | 95.0 |
| 660 | 99.4 | 687 | 88.8 | 728 | 81.0 |
| 661 | 77.9 | 688 | 72.9 | 730 | 88.0 |
| 663 | 100 | 689 | 74.7 | 731 | 95.0 |
| 664 | 77.5 | 693 | 98.5 | 732 | 97.6 |
| 665 | 100 | 694 | 76.8 | 733 | 100 |
| 666 | 98.3 | 695 | 78.1 | 734 | 100 |
| 667 | 89.6 | 696 | 96.9 | 735 | 100 |
| 668 | 94.8 | 697 | 95.9 | 736 | 78.3 |
| 669 | 96.5 | 698 | 96.6 | 737 | 68.0 |
| 670 | 97.1 | 700 | 94.3 | 738 | 100 |
| 673 | 93.1 | 701 | 96.6 | 739 | 100 |
| 740 | 79.5 | | | | |
| 741 | 95.8 | | | | |
| 742 | 95.2 | | | | |
| 743 | 100 | | | | |
| 744 | 96.4 | | | | |
| 745 | 88.5 | | | | |
| 747 | 100 | | | | |
| 755 | 92.5 | | | | |
| Comparative Chemical 1 | 0 | | | | |
| Comparative Chemical 2 | 0 | | | | |

TESTS 3

(Test on the preventive effects for cucumber downy mildew, *Pseudoperonospora cubensis*)

Cucumber seeds (variety: Sagami Hanjiro) were sown at a rate of 12 seeds each in PVC-made pots of 9 cm ×9 cm. The seeds were allowed to grow in a greenhouse for 7 days. A wettable powder containing a test compound and formulated in accordance with the procedure of Example 35 was diluted with water to concentration of 500 ppm of the active ingredient, and the aqueous preparation obtained was then applied at a rate of 10 ml per pot to the cucumber seedlings at their cotyledonous stage. After dried in the air, the seedlings were sprayed and inoculated with a spore suspension of cucumber downy mildew fungi, *Pseudoperonospora cubensis* and then placed in a moist room at 20°–22° C. On the seventh day after the inoculation, the extent of lesion was rated in accordance with the following standards and equation to estimate the degree of development of disease and the control value.

Extent of disease:
- Healthy: No lesion was observed.
- Slight: Leaf area infected < $\frac{1}{3}$ of the whole leaf area
- Medium: Leaf area infected: $\frac{1}{3}$ to $\frac{2}{3}$ of the whole leaf area
- Severe: Leaf area infected > $\frac{2}{3}$ of the whole leaf area Degree of development of disease (%) =
[{(number of healthy leaves × 0) + (number of slightly-infected leaves × 1) + (number of medium-infected leaves × 2) + (number of severely-infected leaves × 3)} ÷ 3N] × 100
where N denotes the total number of the leave under test.

$$\text{Control value (\%)} = \left(1 - \frac{\text{Degree of development of disease in treated plot}}{\text{Degree of development of disease in untreated plot}}\right) \times 100$$

Test Results ar shown in Table 5a–5d below. The same comparative chemicals as in Test 1 were also tested in the same procedure as above, for the comparison purpose.

TABLE 5a

| Compound No. tested | Control value (%) | Compound No. tested | Control value (%) | Compound No. tested | Control value (%) |
|---|---|---|---|---|---|
| 1 | 83 | 130 | 100 | 195 | 91 |
| 2 | 83 | 142 | 92 | 196 | 83 |
| 5 | 100 | 143 | 90 | 198 | 86 |
| 6 | 92 | 161 | 94 | 210 | 100 |
| 7 | 92 | 166 | 100 | 212 | 83 |
| 8 | 100 | 168 | 100 | 219 | 82 |
| 16 | 100 | 169 | 83 | 226 | 100 |
| 17 | 100 | 173 | 100 | 235 | 92 |
| 20 | 90 | 174 | 100 | 244 | 100 |
| 42 | 92 | 176 | 100 | 245 | 90 |
| 52 | 80 | 177 | 90 | 247 | 100 |
| 65 | 100 | 178 | 83 | 250 | 100 |
| 69 | 100 | 179 | 100 | 254 | 89 |
| 73 | 100 | 181 | 100 | 255 | 100 |
| 76 | 91 | 182 | 100 | 256 | 92 |
| 88 | 100 | 183 | 100 | 258 | 91 |
| 91 | 83 | 185 | 92 | 266 | 83 |
| 92 | 100 | 186 | 100 | 270 | 83 |
| 93 | 100 | 187 | 92 | 328 | 85 |
| 96 | 95 | 188 | 88 | 329 | 83 |
| 104 | 83 | 194 | 100 | 343 | 85 |
|  |  | 401 | 92 | Comparative Chemical 1 | 0 |
| 345 | 85 | 402 | 100 |  |  |
| 346 | 100 | 403 | 90 |  |  |
| 361 | 100 | 404 | 80 | Comparative Chemical 2 | 0 |
| 362 | 100 | 407 | 92 |  |  |
| 365 | 92 | 408 | 100 |  |  |
| 374 | 100 | 409 | 100 |  |  |
| 375 | 100 | 416 | 92 |  |  |
| 376 | 100 | 418 | 100 |  |  |
| 377 | 100 | 471 | 100 |  |  |
| 380 | 90 | 478 | 92 |  |  |
| 381 | 100 | 480 | 92 |  |  |
| 382 | 100 | 481 | 92 |  |  |
| 383 | 100 | 482 | 92 |  |  |
| 388 | 100 | 490 | 100 |  |  |
| 390 | 100 | 493 | 100 |  |  |
| 392 | 100 | 495 | 100 |  |  |
| 393 | 90 | 522 | 100 |  |  |
| 394 | 85 | 526 | 100 |  |  |
| 395 | 89 | 527 | 100 |  |  |
| 397 | 100 | 542 | 91 |  |  |
| 398 | 100 |  |  |  |  |
| 400 | 100 |  |  |  |  |

TABLE 5b

| Compound No. tested | Control value (%) |
|---|---|
| 547 | 100 |
| 548 | 83.3 |
| 549 | 100 |
| 550 | 100 |
| 551 | 100 |
| 553 | 100 |
| 555 | 90 |
| 557 | 100 |
| 558 | 100 |
| 566 | 90 |
| 573 | 100 |
| 575 | 100 |
| 576 | 100 |
| 577 | 100 |
| 578 | 100 |
| Comparative Chemical 1 | 0 |
| Comparative Chemical 2 | 0 |

TABLE 5c

| Compound No. tested | Control value (%) | Compound No. tested | Control value (%) | Compound No tested | Control value (%) |
|---|---|---|---|---|---|
| 581 | 100 | 611 | 100 | 640 | 91.7 |
| 582 | 91.7 | 613 | 100 | 641 | 100 |
| 583 | 100 | 615 | 75.0 | 642 | 100 |
| 584 | 100 | 616 | 100 | 645 | 100 |
| 585 | 83.8 | 618 | 100 | 646 | 100 |
| 587 | 100 | 621 | 100 | 647 | 100 |
| 588 | 100 | 623 | 100 |  |  |
| 590 | 91.7 | 624 | 100 |  |  |
| 591 | 100 | 625 | 100 |  |  |
| 592 | 100 | 627 | 100 |  |  |
| 595 | 100 | 628 | 100 |  |  |
| 596 | 100 | 630 | 100 |  |  |
| 597 | 100 | 631 | 100 |  |  |
| 600 | 100 | 632 | 100 |  |  |
| 601 | 100 | 633 | 100 |  |  |
| 602 | 100 | 634 | 100 |  |  |
| 604 | 100 | 635 | 100 |  |  |
| 605 | 100 | 636 | 100 |  |  |
| 606 | 100 | 637 | 100 |  |  |
| 607 | 100 | 638 | 91.7 |  |  |
| 609 | 91.7 | 639 | 100 |  |  |

TABLE 5d

| Compound No. tested | Control value (%) | Compound No. tested | Control value (%) | Compound No. tested | Control value (%) |
|---|---|---|---|---|---|
| 648 | 86.0 | 685 | 100 | 727 | 100 |
| 650 | 100 | 686 | 100 | 728 | 100 |
| 651 | 100 | 687 | 100 | 729 | 83.3 |
| 655 | 80.0 | 690 | 100 | 730 | 100 |
| 660 | 100 | 693 | 100 | 731 | 100 |
| 663 | 100 | 697 | 83.3 | 732 | 100 |
| 664 | 91.7 | 698 | 100 | 733 | 100 |
| 665 | 100 | 700 | 100 | 734 | 100 |
| 666 | 100 | 701 | 91.7 | 735 | 100 |
| 667 | 91.7 | 702 | 91.7 | 736 | 83.3 |
| 668 | 100 | 707 | 100 | 737 | 83.3 |
| 669 | 100 | 708 | 100 | 738 | 100 |
| 673 | 100 | 710 | 100 | 739 | 100 |
| 675 | 100 | 713 | 100 | 742 | 100 |
| 676 | 100 | 714 | 100 | 743 | 100 |
| 677 | 100 | 716 | 100 | 744 | 83.3 |
| 678 | 100 | 717 | 100 | 747 | 100 |
| 679 | 100 | 718 | 100 | 755 | 100 |
| 680 | 100 | 720 | 83.3 | 757 | 100 |
| 681 | 91.7 | 725 | 100 | 758 | 100 |
| 684 | 100 | 726 | 100 | Comparative Chemical 1 | 0 |
|  |  |  |  | Comparative Chemical 2 | 0 |

TEST 4

(Test on the preventive effects for cucumber gray mold, *Botrytis cinerea*)

Cucumber seeds (variety: Sagami Hanjiro) were sown at a rate of 12 seeds each in PVC-made pots of 9 cm ×9 cm. The seeds were allowed to grow for 7 days in a greenhouse. A wettable powder containing a test compound and formulated in accordance with the procedure of Example 35 was diluted with water to a concentration of 500 ppm of the active ingredient, and the aqueous preparation obtained was then sprayed at a rate of 10 ml per pot to the cucumber seedlings at their cotyledonous stage. After dried in the air, the seedlings were sprayed and inoculated with a suspension of homogenized hypha of cucumber gray fungi, *Botrytis cinerea* and then placed in a moist chamber at 20°–23° C. On the fourth day after the inoculation, the overall extent of development of disease in each pot was rated in accordance with the following standard.

Infection index
0: No lesion was observed.
1: Infected area of less than 25% of the total leaf area
2: Infected area of 26–50% of the total leaf area
3: Infected area of 51–75% of the total leaf area
4: Infected area of 76% or more of the total leaf area Results are shown in Table 6a–Table 6c below. The same comparative chemicals as in Test 1 were also tested in the same way as above, for the comparison purpose.

TABLE 6a

| Compound No. tested | Infection Index | Compound No. tested | Infection Index | Compound No tested | Infection Index |
|---|---|---|---|---|---|
| 8 | 0 | 284 | 1 | 387 | 1 |
| 15 | 1 | 288 | 1 | 388 | 0 |
| 76 | 0 | 305 | 1 | 392 | 0 |
| 88 | 0 | 335 | 1 | 393 | 0 |
| 135 | 0 | 336 | 0 | 394 | 0 |
| 159 | 1 | 337 | 1 | 396 | 0 |
| 160 | 1 | 338 | 1 | 397 | 0 |
| 174 | 1 | 340 | 1 | 410 | 1 |
| 176 | 0 | 351 | 0 | 412 | 1 |
| 177 | 1 | 353 | 1 | 471 | 1 |
| 178 | 1 | 356 | 0 | 472 | 1 |
| 179 | 0 | 357 | 1 | 481 | 1 |
| 188 | 1 | 361 | 0 | 490 | 1 |
| 193 | 1 | 362 | 0 | 493 | 0 |
| 194 | 0 | 365 | 0 | 495 | 1 |
| 226 | 1 | 367 | 0 | 525 | 1 |
| 244 | 0 | 374 | 0 | | |
| 245 | 0 | 381 | 0 | Comparative Chemical 1 | 4 |
| 246 | 1 | 382 | 1 | | |
| 247 | 0 | 383 | 0 | Comparative Chemical 2 | 4 |
| 255 | 1 | 385 | 0 | | |
| 260 | 1 | 386 | 0 | | |

TABLE 6b

| Compound No. tested | Infection Index |
|---|---|
| 545 | 0 |
| 547 | 0 |
| 548 | 0 |
| 549 | 0 |
| 551 | 0 |
| 552 | 0 |
| 557 | 0 |
| 558 | 0 |
| 559 | 1 |
| 561 | 1 |
| 565 | 0 |
| 573 | 0 |
| 574 | 0 |
| 575 | 0 |
| 576 | 0 |
| 577 | 0 |
| 578 | 0 |
| 579 | 0 |
| Comparative Chemical 1 | 0 |
| Comparative Chemical 2 | 1 |

TABLE 6c

| Compound No. tested | Infection Index | Compound No. tested | Infection Index | Compound No. tested | Infection Index |
|---|---|---|---|---|---|
| 581 | 0.0 | 611 | 0.0 | 640 | 0.0 |
| 582 | 0.0 | 612 | 0.0 | 641 | 1.0 |
| 583 | 0.0 | 613 | 0.0 | 642 | 0.0 |
| 585 | 0.0 | 621 | 1.0 | 644 | 0.0 |
| 587 | 0.0 | 622 | 0.0 | 645 | 0.0 |
| 588 | 0.0 | 623 | 0.0 | 646 | 0.0 |
| 589 | 1.0 | 624 | 0.5 | 647 | 0.0 |
| 590 | 0.0 | 625 | 0.0 | | |
| 591 | 1.0 | 626 | 1.0 | | |
| 592 | 0.0 | 627 | 0.0 | | |
| 593 | 0.0 | 628 | 0.0 | | |
| 595 | 0.0 | 629 | 0.0 | | |
| 596 | 0.0 | 630 | 0.0 | | |
| 597 | 0.0 | 631 | 0.0 | | |
| 599 | 0.0 | 632 | 0.0 | | |
| 600 | 0.0 | 633 | 0.0 | | |
| 601 | 0.0 | 634 | 0.0 | | |
| | | 635 | 0.0 | | |
| 605 | 0.0 | | | | |
| | | 636 | 0.0 | | |
| 606 | 0.0 | 637 | 0.0 | | |
| 607 | 0.0 | 638 | 1.0 | | |
| 608 | 1.0 | 639 | 0.5 | | |

TEST 5

(Test on the preventive effects for cucumber powdery mildew, *Sphaerotheca fuliginea*)

Cucumber seeds (variety: Sagami Hanjiro) were sown at a rate of 12 seeds each in PVC-made pots of 9 cm ×9 cm. The seeds were allowed to germinate and grow for 7 days in a greenhouse. A wettable powder containing a test compound and formulated in accordance with the procedure of Example 35 was diluted with water to a concentration of 500 ppm of the active ingredient, and the aqueous preparation obtained was then sprayed at a rate of 10 ml per pot to the cucumber seedlings at their cotyledonous stage. After dried in the air, the seedlings were inoculated with spores of cucumber powdery mildew fungi, *Sphaerotheca fuliginea* and then placed in a greenhouse at 25°–30° C. On the tenth day after the inoculation, the overall extent of development of disease in each pot was rated in accordance with the following standard.

Infection index
0: No lesion was observed.
1: Infected area of less than 25% of the total leaf area.
2: Infected area of 26–50% of the total leaf area
3: Infected area of 51–75% of the total leaf area
4: Infected area of 76% or more of the total leaf area.

Results are shown in Table 7a–Table 7c below. The same comparative chemicals as in Test 1 were also tested in the same way as above, for the comparison purpose.

TABLE 7a

| Compound No. tested | Infection Index | Compound No. tested | Infection Index | Compound No. tested | Infection Index |
|---|---|---|---|---|---|
| 1 | 1 | 245 | 0 | 383 | 1 |
| 2 | 1 | 247 | 0 | 385 | 0 |
| 5 | 1 | 255 | 0 | 388 | 0 |
| 8 | 0 | 288 | 1 | 392 | 0 |
| 16 | 1 | 305 | 1 | 393 | 0 |
| 93 | 1 | 316 | 1 | 394 | 0 |
| 96 | 1 | 335 | 1 | 397 | 0 |
| 104 | 1 | 336 | 0 | 400 | 0 |
| 130 | 1 | 337 | 0 | 471 | 1 |
| 135 | 1 | 338 | 1 | 472 | 0 |
| 160 | 1 | 340 | 0 | 490 | 0 |
| 173 | 1 | 351 | 0 | 493 | 1 |
| 174 | 0 | 356 | 1 | 495 | 1 |
| 176 | 1 | 359 | 1 | 511 | 0 |
| 179 | 0 | 361 | 0 | 542 | 1 |
| 181 | 1 | 362 | 1 | | |
| 182 | 1 | 365 | 0 | Comparative Chemical 1 | 3 |
| 183 | 1 | 374 | 1 | | |
| 186 | 1 | 376 | 1 | Comparative Chemical 2 | 4 |
| 226 | 0 | 380 | 0 | | |
| 241 | 1 | 381 | 0 | | |
| 244 | 1 | 382 | 1 | | |

TABLE 7b

| Compound No. tested | Infection Index |
|---|---|
| 545 | 0 |
| 546 | 0 |
| 547 | 0 |
| 548 | 0 |
| 549 | 0 |
| 551 | 0 |
| 553 | 0 |
| 557 | 0 |
| 558 | 0 |
| 559 | 0 |
| 561 | 0 |
| 566 | 0 |
| 573 | 0 |
| 574 | 0 |
| 575 | 0 |
| 576 | 0 |
| 577 | 0 |
| 578 | 0 |
| 579 | 0 |
| Comparative Chemical 1 | 3 |
| Comparative Chemical 2 | 4 |

TABLE 7c

| Compound No. tested | Infection Index | Compound No. tested | Infection Index | Compound No. tested | Infection Index |
|---|---|---|---|---|---|
| 581 | 0.0 | 611 | 0.0 | 640 | 0.0 |
| 582 | 0.0 | 612 | 0.0 | 641 | 0.0 |
| 583 | 0.0 | 613 | 0.0 | 642 | 0.0 |
| 584 | 1.0 | 616 | 0.0 | 645 | 0.0 |
| 585 | 0.0 | 618 | 0.0 | 646 | 0.0 |
| 587 | 0.0 | 622 | 1.0 | 647 | 0.0 |
| 588 | 0.0 | 623 | 0.0 | | |
| 590 | 0.0 | 624 | 1.0 | | |
| 591 | 0.0 | 625 | 0.0 | | |
| 592 | 0.0 | 627 | 0.0 | | |
| 593 | 0.0 | 628 | 0.0 | | |
| 595 | 0.0 | 629 | 0.0 | | |
| 596 | 0.0 | 630 | 0.0 | | |
| 597 | 0.0 | 631 | 0.0 | | |
| 599 | 0.0 | 632 | 0.0 | | |
| 600 | 0.0 | 633 | 0.0 | | |
| 601 | 0.0 | 634 | 0.0 | | |
| 602 | 0.0 | 635 | 0.0 | | |
| 604 | 0.0 | 636 | 0.0 | | |
| 605 | 0.0 | 637 | 0.0 | | |
| 606 | 0.0 | 638 | 0.0 | | |
| 607 | 0.0 | 639 | 0.0 | | |

TEST 6

(Test on the preventive effects for Alternaria sooty spot of Chinese mustard, *Alternaria brassicicola*)

Seeds of Chinese mustard were sown at a rate of 12 seeds each in PVC-made pots of 9 cm ×9 xm. The seeds were allowed to row for 7 days in a greenhouse. A wettable powder containing a test compound and formulated in accordance with the procedure of Example 35 was diluted with water to concentration of 500 ppm of the active ingredient, and the aqueous preparation obtained was then sprayed at a rate of 10 ml per pot to the seedlings of the Chinese mustard at their cotyledon stage. After dried in the air, the seedlings were sprayed and inoculated with a spore suspension of Alternaria sooty spot fungi, *Alternaria brassicicola* and then placed in a moist chamber at 30° C. On the third day after the inoculation, the average number of lesions per leaf was determined to estimate the control value in accordance with the following equation. Test Results of rating evaluated in accordance with the following evaluation standard are given in Table 8a–8c below.

$$\text{Control value (\%)} = \left(1 - \frac{\text{Average number of lesions in treated plot}}{\text{Average number of lesions in untreated plot}}\right) \times 100$$

Evaluation standard:
Class A: Control value > 90%
Class B: Control value = 80–90%
Class C: Control value = 50–79%
Class D: Control value < 50%

Again, the same comparative chemicals as those employed in Test 1 were also tested for the comparison purpose.

TABLE 8a

| Compound No. tested | Evaluation | Compound No. tested | Evaluation | Compound No. tested | Evaluation |
|---|---|---|---|---|---|
| 1 | A | 173 | B | 288 | B |
| 2 | A | 174 | A | 292 | B |
| 5 | B | 176 | A | 298 | B |
| 8 | A | 179 | B | 299 | B |
| 9 | B | 181 | B | 324 | B |
| 10 | B | 182 | B | 337 | A |
| 16 | A | 183 | B | 341 | B |
| 18 | B | 187 | A | 342 | B |
| 26 | B | 194 | A | 345 | B |
| 31 | B | 196 | B | 351 | B |
| 35 | B | 198 | B | 356 | A |
| 65 | B | 219 | B | 357 | A |
| 76 | A | 226 | A | 358 | A |
| 91 | A | 227 | A | 360 | A |
| 93 | A | 244 | A | 361 | A |
| 109 | B | 245 | A | 362 | A |
| 110 | B | 247 | A | 365 | A |
| 123 | B | 249 | B | 366 | B |
| 135 | B | 250 | A | 373 | B |
| 159 | B | 255 | A | 374 | A |
| 164 | B | 259 | B | 376 | A |
| 380 | B | 490 | A | | |
| 381 | A | 493 | B | | |
| 382 | B | 525 | B | | |
| 383 | A | | | | |
| 385 | B | Comparative | | | |

TABLE 8a-continued

| Compound No. tested | Evaluation | Compound No. tested | Evaluation | Compound No. tested | Evaluation |
|---|---|---|---|---|---|
| 387 | A | Chemical 1 | D | | |
| 388 | A | Comparative Chemical 2 | D | | |
| 390 | A | | | | |
| 392 | A | | | | |
| 393 | A | | | | |
| 394 | A | | | | |
| 395 | B | | | | |
| 396 | A | | | | |
| 397 | A | | | | |
| 398 | B | | | | |
| 400 | A | | | | |
| 408 | B | | | | |
| 409 | A | | | | |
| 417 | B | | | | |
| 472 | A | | | | |
| 474 | B | | | | |
| 484 | B | | | | |

TABLE 8b

| Compound No. tested | Evaluation |
|---|---|
| 545 | B |
| 547 | B |
| 548 | A |
| 549 | A |
| 550 | B |
| 551 | A |
| 553 | B |
| 555 | B |
| 556 | B |
| 557 | B |
| 558 | A |
| 559 | B |
| 560 | B |
| 561 | A |
| 665 | B |
| 566 | B |
| 573 | B |
| 574 | B |
| 575 | A |
| 576 | A |
| 577 | B |
| 578 | B |
| 579 | B |
| Comparative Chemical 1 | D |
| Comparative Chemical 2 | D |

TABLE 8c

| Compound No. tested | Evaluation | Compound No. tested | Evaluation | Compound No. tested | Evaluation |
|---|---|---|---|---|---|
| 581 | A | 609 | A | 635 | A |
| 582 | A | 610 | A | 636 | A |
| 583 | A | 611 | A | 637 | A |
| 585 | A | 612 | A | 638 | A |
| 586 | C | 613 | A | 639 | A |
| 587 | A | 614 | B | 640 | A |
| 588 | A | 615 | A | 641 | A |
| 590 | A | 616 | A | 642 | A |
| 591 | A | 618 | A | 643 | A |
| 592 | A | 621 | A | 644 | A |
| 593 | C | 622 | A | 645 | A |
| 595 | A | 623 | A | 646 | A |
| 596 | A | 624 | A | 647 | A |
| 597 | A | 625 | A | | |
| 599 | A | 626 | A | | |
| 600 | A | 627 | A | | |
| 601 | A | 628 | A | | |
| 602 | A | 629 | A | | |
| 604 | A | 630 | A | | |
| 605 | A | 631 | A | | |
| 606 | A | 632 | A | | |
| 607 | A | 633 | A | | |
| 608 | A | 634 | A | | |

TEST 7

(Test on the preventive effects for rice sheath blight at low rate application of test compounds)

Each 9 seedlings of rice plants (variety: Kinmaze) were transplanted in a white porcelain pot of 9 cm diameter containing paddy soils. The plants were allowed to grow to the 7–8 leaf stage in a greenhouse. A wettable powder containing a test compound formulated in accordance with the procedure of Example 35 was diluted in water to concentrations of the active ingredient as specified in the following Table 9. The aqueous preparation obtained was sprayed onto the rice plants at a rate of 10 ml per pot. After dried in the air, the each plant so treated was inoculated with an agar disk of the pathogenic fungus of rice sheath blight (*Rhizoctonia solani*) which has been cultured on a potato dextrose agar medium for 2 days, on the basal part of the sheath. The plants inoculated were kept in a moist chamber to allow the disease development at 28° C. Seven days later, the height of lesion formed on the sheath was measured.

Then, the control value (%) of the disease provided by the test compound was calculated according to the following equation.

$$\text{Control value (\%)} = \left(1 - \frac{\text{Average height of lesions in treated plot}}{\text{Average height of lesions in untreated plot}}\right) \times 100$$

The test was made in three replicates using 3 pots in each plot. The results obtained are summarized in Table 9 below.

TABLE 9

| Compound No. tested | Control value (%) Concentration of the active ingredient in the sprayed liquid preparation | | |
|---|---|---|---|
| | 1 ppm | 3 ppm | 10 ppm |
| 93 | 64.5 | 79.3 | 84.3 |
| 388 | 89.1 | 93.9 | 98.0 |
| 392 | 80.0 | 97.5 | 99.2 |
| 135 | 87.9 | 91.5 | 98.6 |
| 503 | 86.7 | 94.7 | 98.3 |
| 557 | 88.9 | 92.4 | 96.6 |
| 558 | 85.5 | 94.9 | 97.5 |
| 642 | 96.8 | 99.4 | 99.8 |
| 583 | 94.2 | 96.7 | 97.5 |
| 693 | 72.0 | 81.1 | 97.2 |
| 665 | 60.9 | 71.7 | 93.5 |
| 244 | 90.0 | 92.9 | 98.6 |
| 472 | 71.6 | 85.4 | 98.1 |
| 336 | 66.1 | 87.6 | 88.3 |
| 154 | 81.2 | 88.9 | 97.3 |
| 632 | 76.4 | 97.7 | 97.7 |
| 625 | 81.3 | 94.6 | 97.6 |
| 592 | 92.5 | 97.5 | 98.4 |
| 659 | 73.3 | 97.2 | 99.1 |

TABLE 9-continued

| Compound No. tested | Control value (%) Concentration of the active ingredient in the sprayed liquid preparation | | |
|---|---|---|---|
| | 1 ppm | 3 ppm | 10 ppm |
| Untreated | 0 | 0 | 0 |

Class A: Control value of greater than 90%, or Infection index of 0.
Class B: Control value of from 70% and up to 90%, or Infection index of 1.
Class C: Control value of greater than 50% and up to 70%, or Infection index of 2.
Class D: Control value of less than 50%, or Infection index of 3–4.

The results ar summarised in Table 10 below.

TABLE 10

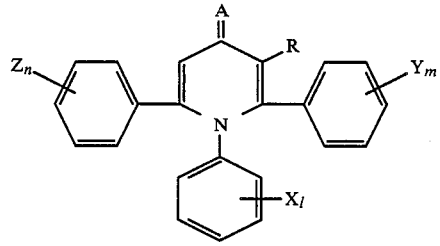

| | Substituents in tested compound | | | | | Evaluation of Control value | | | | | |
|---|---|---|---|---|---|---|---|---|---|---|---|
| | $X_l$ | $Y_m$ | $Z_n$ | A | R | Rice sheath blight | Rice blast | Cucumber downy mildew | Cucumber gray mold | Cucumber powdery mildew | Alternaria sooty spot |
| Compound No. tested | | | | | | | | | | | |
| 93 | 3,5-(OCH$_3$)$_2$ | H | H | O | CH$_3$ | A | A | A | D | B | A |
| 388 | 3,5-(OCH$_3$)$_2$ | 2-Cl | H | O | CH$_3$ | A | A | A | A | A | A |
| 392 | 3,5-(OCH$_3$)$_2$ | 4-OCH$_3$ | H | O | CH$_3$ | A | A | A | A | A | A |
| 135 | 2-Cl 5-OCH$_3$ | H | H | O | CH$_3$ | A | A | C | A | B | B |
| 503 | 2-Cl 5-OCH$_3$ | H | 2-F | O | CH$_3$ | A | A | A | A | A | A |
| 557 | 2-Cl 3,5-(OCH$_3$)$_2$ | H | 2-F | O | CH$_3$ | A | A | A | A | A | A |
| 558 | 3,5-(OCH$_3$)$_2$ | 2-F | 2-F | O | CH$_3$ | A | A | A | A | A | A |
| 642 | 3,5-(OCH$_3$)$_2$ | 2,4-F$_2$ | 2-F | O | CH$_3$ | A | A | A | A | A | A |
| 583 | H | 2-Cl | 2-F | O | CH$_3$ | A | A | A | A | A | A |
| 693 | 3,5-(OCH$_3$)$_2$ | 2-F | 2-F | O | Cl | A | A | A | A | A | A |
| 665 | 3,5-(OCH$_3$)$_2$ | 2-F | 2-F | S | CH$_3$ | A | A | A | A | A | A |
| 244 | H | 2,4-F$_2$ | H | O | CH$_3$ | A | A | A | A | B | A |
| 472 | 2-Cl | H | 2-F | O | CH$_3$ | A | A | C | B | A | A |
| 336 | 2-Cl | 2-Cl | H | O | CH$_3$ | A | B | C | A | A | B |
| 154 | 2-Cl 3,5-(OCH$_3$)$_2$ | H | H | O | CH$_3$ | A | A | A | A | A | A |
| 633 | 3,5-(OCH$_3$)$_2$ | 2-Cl | 2-F | O | CH$_3$ | A | A | A | A | A | A |
| 625 | 2-Cl 3,5-(OCH$_3$)$_2$ | 4-OCH$_3$ | 2-F | O | CH$_3$ | A | A | A | A | A | A |
| 592 | 2-Br 3,5-(OCH$_3$)$_2$ | H | 2-F | O | CH$_3$ | A | A | A | A | A | A |
| Comparative compound A | H | H | H | O | H | B | D | B | D | C | D |
| Comparative compound B | 2-Cl | H | H | O | H | A | D | D | D | D | B |
| Comparative compound C | 3-OCH$_3$ | H | H | O | H | A | D | B | D | D | C |
| Comparative compound D | H | H | H | O | CH$_3$ | A | D | D | D | D | D |
| Comparative compound E | 3-CH$_3$ | H | H | O | CH$_3$ | A | D | D | D | D | C |

In Table 10 above, when "H" is shown in the columns of "$X_l$", "$Y_m$" and/or "$Z_n$", this again means that the substituent X, Y and Z are absent, that is say, that the value of l, m and/or n is zero.

In the untreated plot, the average height of the sheath blight lesions amounted to 10.86 cm.

TEST 8 the procedures of Tests 1 to 6 were respectively repeated using some compounds of this invention as indicated in Table 10 shown below, as well as another, comparative compounds A to comparative compound E as indicated in Table 10. The control value (%) for the respective plant disease was evaluated in the same manner as in Tests 1, 2, 3 and 6, or the infection index was evaluated in the same manner as in Tests 4 and 5 above.

The test results obtained are rated in accordance with the following evaluation standards:

What is claimed is:

1. A 4(1H)-pyridinone derivative represented by the formula

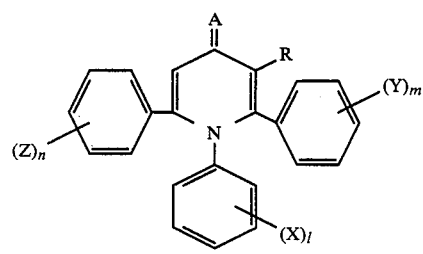

wherein X, Y and Z are the same or different and are independently a halogen atom, a nitro group, a cyano group, a hydroxy group, aldehyde group (—CHO), a lower alkyl group, a halogen-substituted lower alkyl group, a lower cyanoalkyl group, a lower hydroxyalkyl group, a lower alkoxyalkyl group, a lower alkoxy group, a halogen-substituted lower alkoxy group, a lower alkoxyalkoxy group, a lower alkenyl group, a lower alkenyloxy group, a lower alkynyl group, a lower alkynyloxy group, a lower alkanoyl group, a lower alkanoyloxy group, a phenyl group, a phenoxy group, a carbamoyl group, a lower alkylcarbamoyloxy group, a carboxyl or carboxylate group of the formula —COOR$^1$ where R$^1$ is a hydrogen atom or a lower alkyl group, or a substituted or unsubstituted amino group of the formula

where R$^2$ and R$^3$ are the same or different and are each a hydrogen atom, a lower alkyl group or a lower alkanoyl group; or X, Y and Z are independently a group of the formula —(O)$_p$—S—R$^4$ is a lower alkyl group and p is an integer of 0 to 3; or X, Y and Z are independently a trimethylene group or a methylene-dioxo group bonded to and bridging between the adjacent two carbon atoms of the same benzene ring to which X, Y and Z is linking so that X, Y and Z taken together with said two adjacent two carbon atoms of the same benzene ring forms a 5-membered ring, l, m and n are independently an integer of 0 to 5, R is a halogen atom, a cyano group, a lower alkyl group, a halogen-substituted lower alkyl group, a lower alkoxy group, a lower alkenyl group, a lower alkynyl group, a phenyl group, a benzyl group, a trimethylsilylethynyl group, a carboxyl or carboxylate group of the formula —COOR$^1$ where R$^1$ is as defined above, or a substituted methyl group of the formula —CH$_2$OR$^5$ where R$^5$ is a hydrogen atom, a lower alkyl group or a benzoyl group, A is an oxygen atom or a sulfur atom, provided that when R is methyl and A is an oxygen atom, l, m and n do not denote zero simultaneously; and provided that when R and X are each a methyl group, A is an oxygen atom and l is 1, m and n do not denote zero simultaneously, and a salt of the compound of the formula (I) above.

2. A compound as claimed in claim 1 in which R is a (C$_1$-C$_6$) alkyl group, a halogen atom, a cyano group or a carboxyl or carboxylate group of the formula —COOR$^1$ where R$^1$ is a hydrogen atom or a lower alkyl group.

3. A compound as claimed in claim 1, in which R is a (C$_1$-C$_4$) alkyl group, a chlorine atom or a bromine atom.

4. A compound as claimed in claim 1 in which X, Y and Z are the same or different and are independently a lower alkyl group, a lower alkoxy group, a halogen-substituted lower alkyl group, a lower alkoxy group, a halogen-substituted lower alkoxy group, a halogen group, nitro group, cyano group, a lower alkenyl group, a lower alkenyloxy group, a lower alkynyl group or a lower alkynyloxy group, or X, Y and Z are independently a trimethylene group or a methylene-dioxo group bonded to and bridging between the adjacent two carbon atoms of the same benzene ring to which X, Y or Z is linking so that X, Y or Z taken together with said two carbon atoms of the same benzene ring forms a 5-membered ring, l, m and n are independently an integer of 0 to 5, A is an oxygen atom or a sulfur atom.

5. A compound as claimed in claim 1 in which two or more groups are present for each of the groups X, Y and Z and they are the same or different from each other in their nature.

6. A compound as claimed in claim 1 in which the sum of l, m and n is equal to 2 or greater than 2.

7. A compound as claimed in claim 1 in which X is a halogen atom or a lower alkoxy group or a combination of halogen atom(s) and lower alkoxy group(s); Y is a halogen atom or a lower alkoxy group or a combination of halogen atom(s) and lower alkoxy group(s); and Z is a halogen atom or a lower alkoxy group or a combination of halogen atom(s) and lower alkoxy group(s).

8. A compound as claimed in claim 1 in which one, two or three groups for X is or are present therein and positioned at the 2-position, the 3-position, the 2- and 4-positions, the 3- and 5-positions or the 2-, 3- and 5-positions of the benzene ring to which the group(s) X is or are linking.

9. A compound as claimed in claim 1, which is represented by the formula

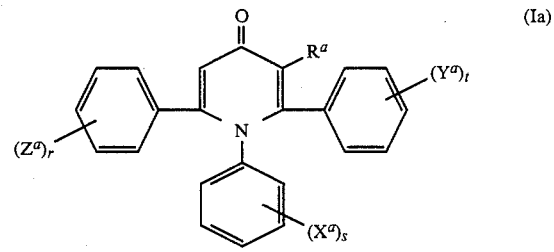

(Ia)

wherein X$^a$ is a halogen atom, a nitro group, a cyano group, a hydroxy group, a lower alkyl group, a halogen-substituted lower alkyl group, a lower cyanoalkyl group, a lower hydroxyalkyl group, a lower alkoxyalkyl group, a lower alkoxy group, a halogen-substituted lower alkoxy group, a lower alkoxyalkoxy group, a lower alkenyl group, a lower alkenyloxy group, a lower alkynyl group, a lower alkynyloxy group, a lower alkanoyl group, a lower alkanoyloxy group, a phenyl group, a phenoxy group, a carbamoyl group, a lower alkylcarbamoyloxy group, a carboxyl or carboxylate group of the formula —COOR$^1$ where R$^1$ is a hydrogen atom or a lower alkyl group, or a substituted or unsubstituted amino group of the formula

where R$^2$ and R$^3$ are the same or different and are each a hydrogen atom, a lower alkyl group or a lower alkanoyl group; or X$^a$ is a group of the formula —(O)$_p$—S—R$^4$ where R$^4$ is a lower alkyl group and p is an integer of 0 to 3; or X$^a$ is a trimethylene group or a methylene-dioxo group bonded to and bridging between the adjacent two carbon atoms of the same benzene ring to which $X^a$ is linking so that $X^a$ taken together with said two adjacent two carbon atoms of the benzene ring forms a 5-membered ring, $Y^a$ is a halogen atom, a nitro group, a cyano group, a hydroxy group, a lower alkyl group, a halogen-substituted lower alkyl group, a lower hydroxyalkyl group, an lower alkoxyalkyl group, a lower alkoxy group, a halogen-substituted lower alkoxy group, a lower alkoxyalkoxy group, a lower alkenyl group, a lower alkneyloxy group, a lower alkynyl group, a lower alkynyloxy group, a lower alkanoyl group, a lower alkanoyloxy group, a carbamoyl group, a lower alkylcarbamoyloxy group, a carboxyl or carboxylate group of the formula —COOR$^1$ where R$^1$ is a hydrogen atom or a lower alkyl group, or $Y^a$ is a group of the formula —(O)$_p$—S—R$^4$ where R$^4$ is a lower alkyl group and p is an integer of 0 to 3; or $Y^a$ is a trimethylene group or a methylene-dioxo group bonded to and bridging between the adjacent two carbon atoms of the same benzene ring to which $Y^a$ is linking so that $Y^a$ taken together with said two adjacent carbon atoms of the same benzene ring forms a 5-membered ring, $Z^a$ is a halogen atom, a nitro group, a cyano group, a hydroxyl group, aldehyde group (—CHO), a lower alkyl group, a halogen-substituted lower alkyl group, a lower hydroxyalkyl group, a lower alkoxyalkyl group, a lower alkoxy group, a halogen-substituted lower alkoxy group, a lower alkoxyalkoxy group, a lower alkenyl group, a lower alkenyloxy group, a lower alkynyl group, a lower alkynyloxy group, a lower alkanoyl group, a lower alkanoyloxy group, a carbamoyl group, a lower alkylcarbamoyloxy group, a carboxyl or carboxylate group of the formula —COOR$^1$ where R$^1$ is a hydrogen atom or a lower alkyl group, or $Z^a$ is a group of the formula —(O)$_p$—S—R$^4$ where R$^4$ is a lower alkyl group and p is an integer of 0 to 3; or $Z^a$ is a trimethylene group or a methylene-dioxo group bonded to and bridging between the adjacent two carbon atoms of the same benzene ring to which $Z^a$ is linking so that $Z^a$ taken together with said two adjacent two carbon atoms of the same benzene ring forms a 5-membered ring, s is an integer of zero, 1, 2 or 3; t is an integer of zero, 1 or 2; and r is an integer of zero, 1 or 2, R$^a$ is a halogen atom, a cyano group, a lower alkyl group, a halogen-substituted lower alkyl group, a lower alkoxy group, a lower alkenyl group, a lower alkynyl group, a phenyl group, a benzyl group, a trimethylsilyethynyl group, a carboxyl or carboxylate group of the formula —COOR$^1$ where R$^1$ is as defined above, or a substituted methyl group of the formula —CH$_2$OR$^5$ where R$^5$ is a hydrogen atom, a lower alkyl group or a benzoyl group, provided that when R$^a$ is methyl, s, t, and r do not denote zero simultaneously.

10. A compound as claimed in claim 1, which is represented by the formula

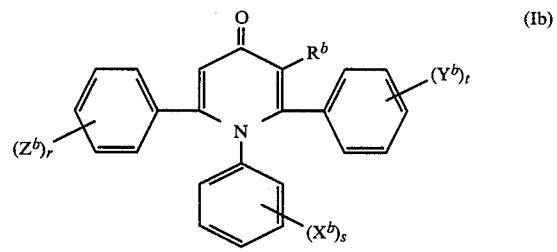

wherein $X^b$ is a halogen atom or a lower alkoxy group or a combination of halogen atom(s) and lower alkoxy group(s); $Y^b$ is a halogen atom, or a lower alkoxy group; and $Z^b$ is a halogen atom, s is an integer of zero, 1, 2 or 3; t is an integer of zero, 1 or 2; and r is an integer of zero, 1 or 2.

R$^b$ is a lower alkyl group or a halogen atom, provided that when R$^b$ is methyl, s, t and r do not denote zero simultaneously.

11. A compound as claimed in claim 1, which is represented by the formula

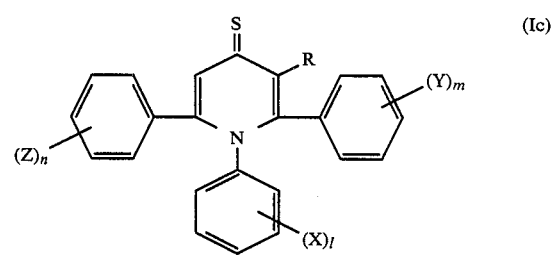

wherein X, Y and Z are the same or different and are independently a halogen atom, a lower alkoxy group, a lower alkenyl group, a lower alkenyloxy group, a lower alkynyl group or a lower alkynyloxy group, l, m and n are independently an integer of 0 to 5, R is a lower alkyl group or a halogen-substituted lower alkyl group.

12. A compound as claimed in claim 1, which is represented by the formula

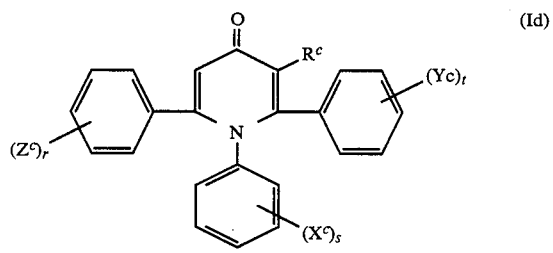

wherein $X^c$ is a lower alkyl group; $Y^c$ is a halogen atom, a lower alkyl group, or a lower alkoxy group; and $Z^c$ is a halogen atom, s is an integer of zero, 1, 2 or 3; t is an integer of zero, 1 or 2; and r is an integer of zero, 1 or 2, R$^c$ is a lower alkyl group or a halogen atom, provided that when R$^c$ is methyl, s, t and r do not denote zero simultaneously, and provided that t and r do not denote zero simultaneously.

13. A compound as claimed in claim 1 or claim 9, which is selected from a compound of the formula:

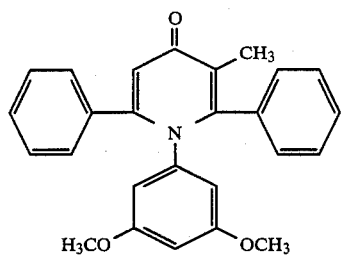
a compound of the formula:
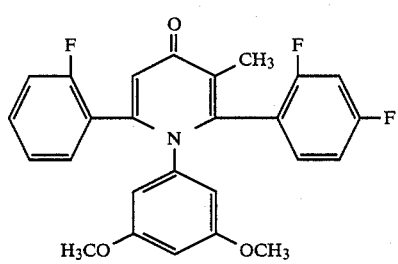
a compound of the formula:
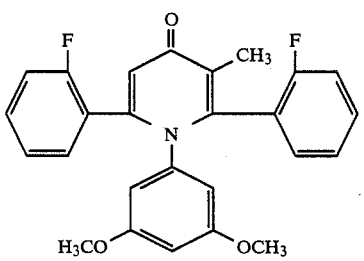
a compound of the formula:
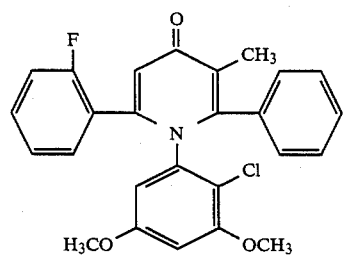
a compound of the formula:
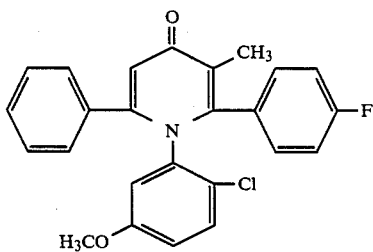
a compound of the formula:
-continued
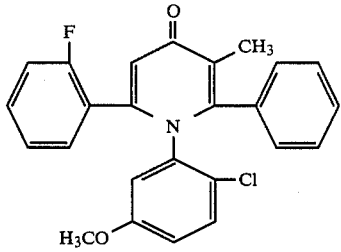
a compound of the formula:
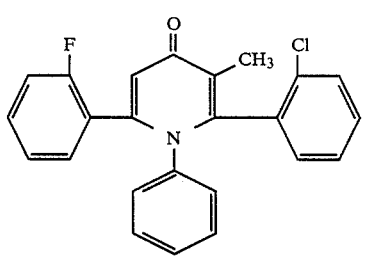
a compound of the formula:
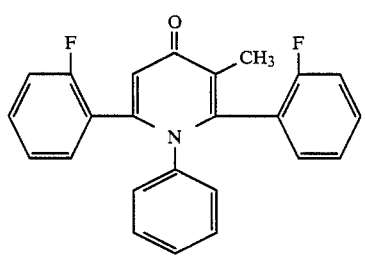
a compound of the formula:
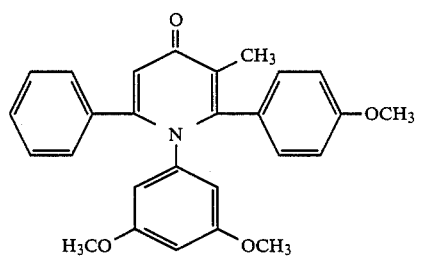
a compound of the formula:
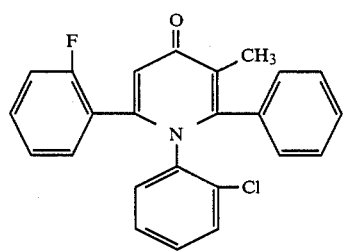
a compound of the formula -continued
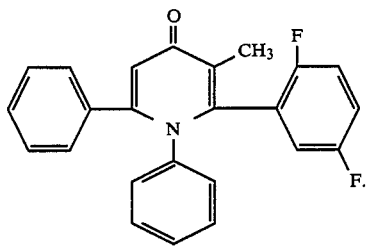
14. A compound as claimed in claim 1, selected from the group consisting of
a compound of the formula
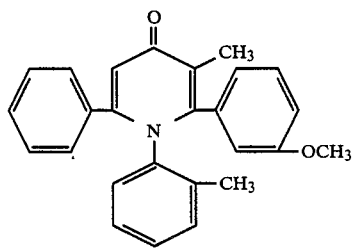
a compound of the formula
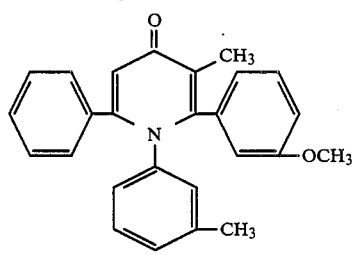
a compound of the formula
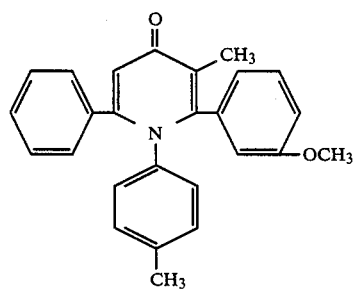
a compound of the formula
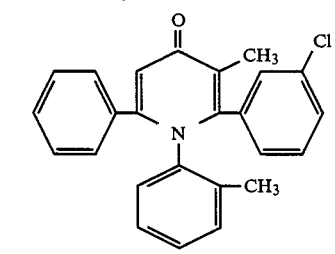
a compound of the formula
-continued
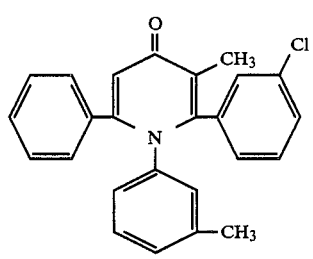
a compound of the formula
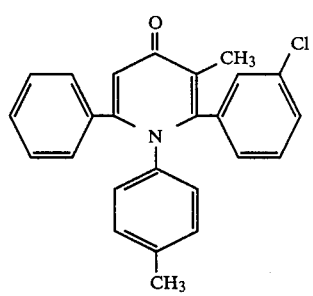
a compound of the formula
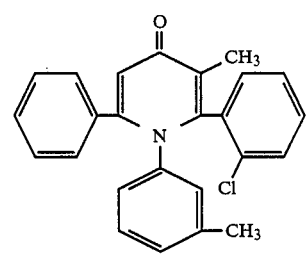
a compound of the formula
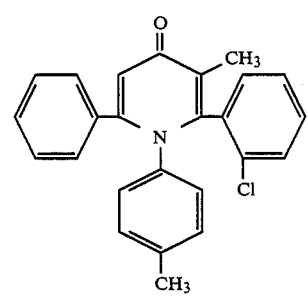
a compound of the formula
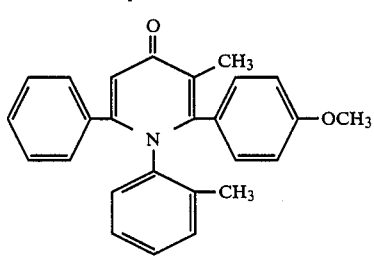
a compound of the formula -continued
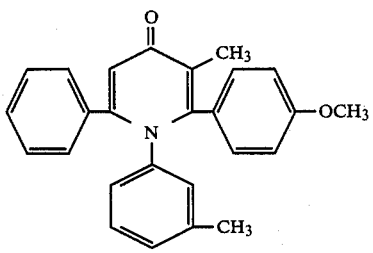
a compound of the formula
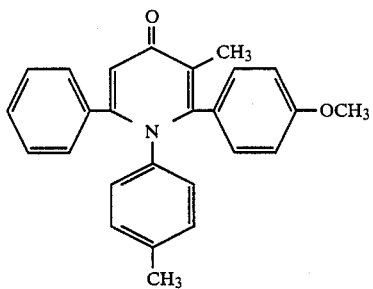
a compound of the formula
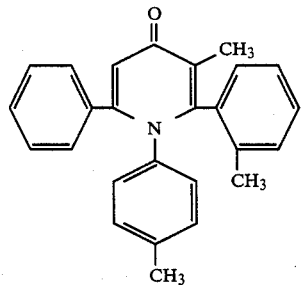
a.compound of the formula
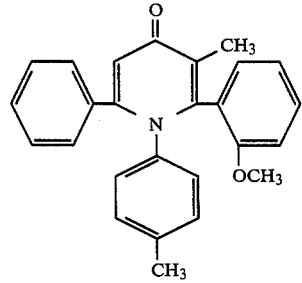
a compound of the formula
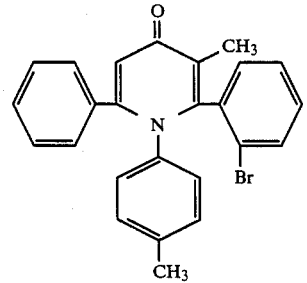
a compound of the formula
-continued
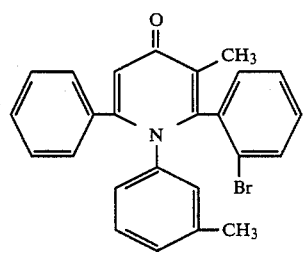
a compound of the formula
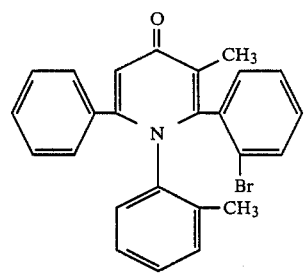
a compound of the formula
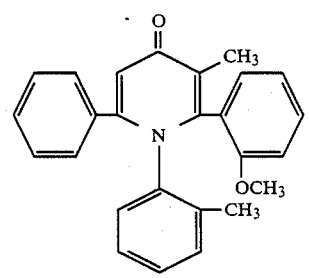
a compound of the formula
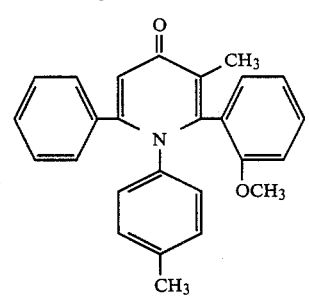
a compound of the formula
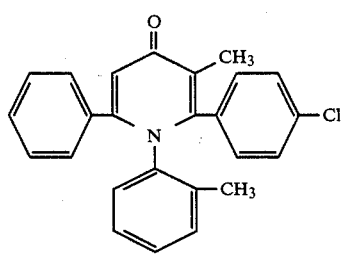
a compound of the formula -continued

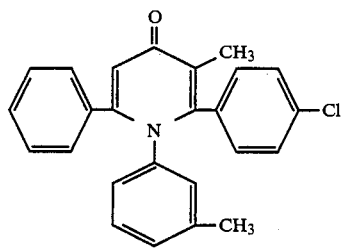

a compound of the formula

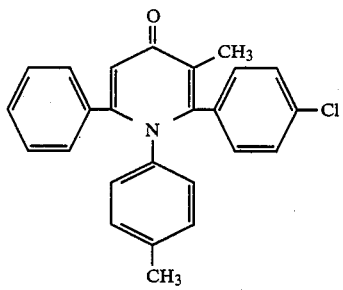

a compound of the formula

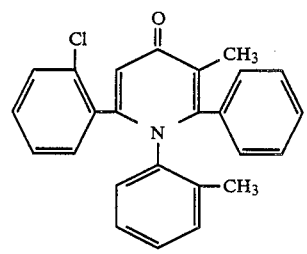

a compound of the formula

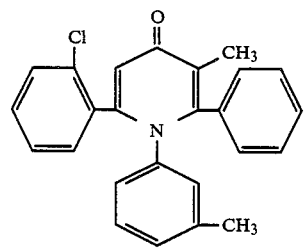

a compound of the formula

-continued

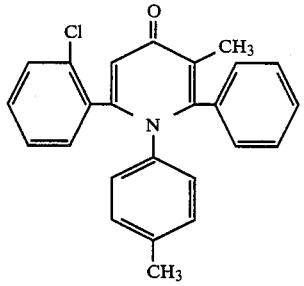

a compound of the formula

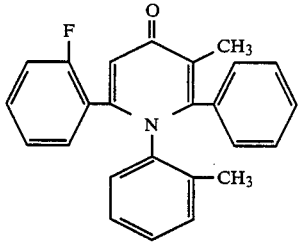

a compound of the formula

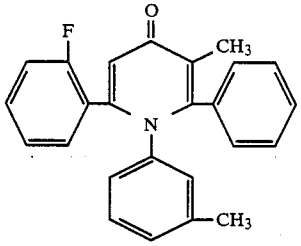

a compound of the formula

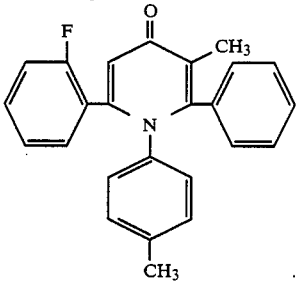

15. A fungicidal composition for agricultural and horticultural utilities, which comprises a compound of the formula (I) as defined in claim 1 or a salt thereof as the active ingredient, in combination with a carrier for the active ingredient.

* * * * *

UNITED STATES PATENT AND TRADEMARK OFFICE
CERTIFICATE OF CORRECTION

PATENT NO. : 4,871,751

DATED : Oct. 3, 1989

INVENTOR(S) : Norihisa Yonekura, et al

It is certified that error appears in the above-identified patent and that said Letters Patent is hereby corrected as shown below:

On the title page, item [73]:

The first Assignee is incorrectly recorded "Kumai Chemical Industry Co., Ltd." should be:

--Kumiai Chemical Industry Co., Ltd.--

Signed and Sealed this

Eighth Day of January, 1991

Attest:

HARRY F. MANBECK, JR.

Attesting Officer     Commissioner of Patents and Trademarks